United States Patent
Gielen-Haertwig et al.

(10) Patent No.: US 8,343,987 B2
(45) Date of Patent: *Jan. 1, 2013

(54) HETEROCYCLIC DERIVATIVES

(75) Inventors: Heike Gielen-Haertwig, Monheim (DE); Barbara Albrecht, Wülfrath (DE); Jörg Keldenich, Wuppertal (DE); Volkhart Li, Velbert (DE); Josef Pernerstorfer, Hofheim (DE); Karl-Heinz Schlemmer, Wuppertal (DE); Leila Telan, Düsseldorf (DE)

(73) Assignee: Bayer Intellectual Property GmbH, Monheim (DE)

( * ) Notice: Subject to any disclaimer, the term of this patent is extended or adjusted under 35 U.S.C. 154(b) by 318 days.

This patent is subject to a terminal disclaimer.

(21) Appl. No.: 12/633,723

(22) Filed: Dec. 8, 2009

(65) Prior Publication Data

US 2010/0184788 A1    Jul. 22, 2010

Related U.S. Application Data

(63) Continuation of application No. 10/590,786, filed as application No. PCT/EP2005/001487 on Feb. 15, 2005, now Pat. No. 7,893,073.

(30) Foreign Application Priority Data

Feb. 26, 2004   (EP) ................................. 04004315

(51) Int. Cl.
   *C07D 403/04*   (2006.01)
   *A61K 31/506*   (2006.01)
(52) U.S. Cl. ........................................ 514/274; 544/315
(58) Field of Classification Search .................. 544/315; 514/274
   See application file for complete search history.

(56) References Cited

U.S. PATENT DOCUMENTS

| 5,532,366 | A | 7/1996 | Edwards et al. |
| 7,199,136 | B2 | 4/2007 | Gielen-Haertwig et al. |
| 7,687,510 | B2 | 3/2010 | Gielen-Haertwig et al. |
| 7,893,073 | B2 * | 2/2011 | Gielen-Haertwig et al. . 514/274 |
| 2008/0045541 | A1 | 2/2008 | Gielen-Haertwig et al. |

FOREIGN PATENT DOCUMENTS

| WO | 2005037799 A1 | 4/2005 |
| WO | 2005082864    | 9/2005 |

OTHER PUBLICATIONS

Ulrich, Chapter 4: Crystallization, Kirk-Othmer Encyclopeida of Chemical Technology, Aug. 2002.
Roghanian, et al., "Inflammatory Lung Secretions Inhibit Dendritic Cell Maturation and Function via Neutrophil Elastase," Am. J. of Respiratory and Critical Care Medicine, 174:1189-1109 (2006).
Lewandowski, et al., "A Combinatorial Approach to Recognition of Chirality: Preparation of Highly Enantioselective Aryl-Dihdropyrimidine Selectors for Chiral HPLC," J. Comb. Chem, pp. 105-112 (1999).
Vippagunta, et al., "Crystalline Solids," Advanced Drug Delivery Reviews, 48:3-26 (2001).
Pending U.S. Appl. No. 10/590,770, filed Jun. 18, 2007. Published as US2008-0064704.
Pending U.S. Appl. No. 10/589,907, filed Jun. 29, 2007. Published as US2008-0045541.

* cited by examiner

*Primary Examiner* — Deepak Rao

(74) *Attorney, Agent, or Firm* — Karen B. King; Thomas C. Blankinship

(57) ABSTRACT

The invention relates to novel heterocyclic derivatives of the general formula (I), processes for their preparation, and their use in medicaments, especially for the treatment of chronic obstructive pulmonary diseases, acute coronary syndrome, acute myocardial infarction, and heart failure development.

15 Claims, No Drawings

HETEROCYCLIC DERIVATIVES

This application is a continuation of U.S. Ser. No. 10/590,786 filed Jul. 20, 2007 now U.S. Pat. No. 7,893,073, which is a 371 of PCT/EP05/01487 filed Feb. 15, 2005.

The present invention relates to novel heterocyclic derivatives, processes for their preparation, and their use in medicaments, especially for the treatment of chronic obstructive pulmonary diseases, acute coronary syndrome, acute myocardial infarction and heart failure development.

The fibrous protein elastin, which comprises an appreciable percentage of all protein content in some tissues, such as the arteries, some ligaments, the lungs and the heart, can be hydrolysed or otherwise destroyed by a select group of enzymes classified as elastases. Human leukocyte elastase (HLE, EC 3.4.21.37), also known as human neutrophil elastase (HNE), is a glycosylated, strongly basic serine protease and is found in the azurophilic granules of human polymorphonuclear leukocytes (PMN). HNE is released from activated PMN and has been implicated causally in the pathogenesis of acute and chronic inflammatory diseases. HNE is capable of degrading a wide range of matrix proteins including elastin and collagen, and in addition to these actions on connective tissue HNE has a broad range of inflammatory actions including upregulation of IL-8 gene expression, oedema formation, mucus gland hyperplasia and mucus hypersecretion. It also acts as a mediator of tissue injury by hydrolysing collagen structures, e.g. in the heart after acute myocardial infarction or during the development of heart failure, thus damaging endothelial cells, promoting extravasation of neutrophils adhering to the endothelium and influencing the adhesion process itself.

Pulmonary diseases where HNE is believed to play a role include lung fibrosis, pneumonia, acute respiratory distress syndrome (ARDS), pulmonary emphysema, including smoking-induced emphysema, chronic obstructive pulmonary diseases (COPD) and cystic fibrosis. In cardiovascular diseases, HNE is involved in the enhanced generation of ischaemic tissue injury followed by myocardial dysfunction after acute myocardial infarction and in the remodelling processes occurring during the development of heart failure. HNE has also been causally implicated in rheumatoid arthritis, atherosclerosis, brain trauma, cancer and related conditions in which neutrophil participation is involved.

Thus, inhibitors of HLE activity can be potentially useful in the treatment of a number of inflammatory diseases, especially of chronic obstructive pulmonary diseases [R. A. Stockley, Neutrophils and protease/antiprotease imbalance, Am. J. Respir. Crit. Care 160, S49-S52 (1999)]. Inhibitors of HLE activity can also be potentially useful in the treatment of acute myocardial syndrome, unstable angina pectoris, acute myocardial infarction and coronary artery bypass grafts (CABG) [C. P. Tiefenbacher et al., Inhibition of elastase improves myocardial function after repetitive ischaemia and myocardial infarction in the rat heart, Eur. J. Physiol. 433, S563-S570 (1997); Dinerman et al., Increased neutrophil elastase release in unstable angina pectoris and acute myocardial infarction, J. Am. Coil. Cardiol. 15, 1559-1563 (1990)], of the development of heart failure [S. J. Gilbert et al., Increased expression of promatrix metalloproteinase-9 and neutrophil elastase in canine dilated cardiomyopathy, Cardiov. Res. 34, S377-S383 (1997)] and of atherosclerosis [Dollery et al., Neutrophil elastase in human atherosclerotic plaque, Circulation 107, 2829-2836 (2003)].

The synthesis of 5-ethoxycarbonyl-1-phenyl-6-methyl-4-(3-nitrophenyl)-3,4-dihydropyrimidin-2(1H)-one is described in J. Heterocyclic Chem. 38, 1051 (2001). A pharmacological activity of this compound is not mentioned.

The present invention relates to compounds of the general formula (I)

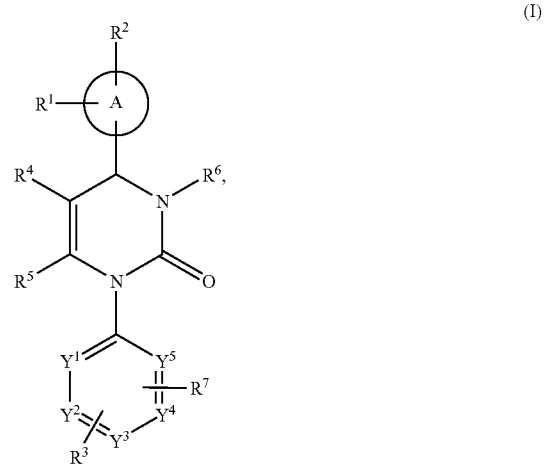

wherein
A represents an aryl or heteroaryl ring,
$R^1$, $R^2$ and $R^3$ independently from each other represent hydrogen, halogen, nitro, cyano, $C_1$-$C_6$-alkyl, hydroxy or $C_1$-$C_6$-alkoxy, wherein $C_1$-$C_6$-alkyl and $C_1$-$C_6$-alkoxy can be further substituted with one to three identical or different radicals selected from the group consisting of halogen, hydroxy and $C_1$-$C_4$-alkoxy,
$R^4$ represents trifluoromethylcarbonyl, $C_1$-$C_6$-alkylcarbonyl, $C_1$-$C_6$-alkoxycarbonyl, $C_2$-$C_6$-alkenoxycarbonyl, hydroxycaxbonyl, aminocarbonyl, mono- or di-$C_1$-$C_4$-alkylaminocarbonyl, $C_6$-$C_{10}$-arylaminocaxbonyl, arylcarbonyl, heteroarylcarbonyl, heterocyclylcarbonyl, heteroaryl, heterocyclyl or cyano, wherein $C_1$-$C_6$-alkylcarbonyl, $C_1$-$C_6$-alkoxy-carbonyl, mono- and di-$C_1$-$C_4$-alkylaminocarbonyl can be further substituted with one to three identical or different radicals selected from the group consisting of $C_3$-$C_8$-cycloalkyl, hydroxy, $C_1$-$C_4$-alkoxy, $C_1$-$C_4$-alkoxycarbonyl, hydroxycarbonyl, aminocarbonyl, mono- and di-$C_1$-$C_4$-alkylaminocarbonyl, $C_1$-$C_4$-alkylcarbonylamino, N—($C_1$-$C_4$-alkylcarbonyl)-N—($C_1$-$C_4$-alkyl)amino, cyano, amino, mono- and di-$C_1$-$C_4$-alkylamino, heteroaryl, heterocyclyl and tri-($C_1$-$C_6$-alkyl)-silyl, and wherein heteroarylcarbonyl, heterocyclylcarbonyl, heteroaryl and heterocyclyl can be further substituted with $C_1$-$C_4$-alkyl,
$R^5$ represents $C_1$-$C_4$-alkyl, which can be substituted with one to three identical or different radicals selected from the group consisting of halogen, hydroxy, $C_1$-$C_6$-alkoxy, $C_2$-$C_6$-alkenoxy, $C_1$-$C_6$-alkylthio, amino, mono- and di-$C_1$-$C_6$-alkylamino, arylamino, hydroxycarbonyl, $C_1$-$C_6$-alkoxycarbonyl and the radical —O—$C_1$-$C_4$-alkyl-O—$C_1$-$C_4$-alkyl, or
$R^5$ represents amino,
$R^6$ represents
  a group of the formula -T-U wherein
    T represents a $C_1$-$C_6$-alkanediyl or $C_2$-$C_6$-alkenediyl group
    and
    U represents
      $C_6$-$C_{10}$-aryl or 5- or 6-membered heteroaryl each of which is substituted by one, two or three radicals independently selected from the group consisting of halogen, $C_1$-$C_6$-alkyl, 5- or 6-membered heteroaryl and a group of the formula —V—W wherein V represents a bond or a $C_1$-$C_6$-alkanediyl or $C_2$-$C_6$-alkenediyl group both of which can be further substituted by $C_3$-$C_8$-cycloalkyl, and W represents $C_1$-$C_6$-alkoxycarbonyl or hydroxycarbonyl, a group of the formula —C(=O)—NR$^a$—SO$_2$—R$^b$ wherein R$^a$ represents hydrogen or $C_1$-$C_6$-alkyl, and R$^b$ represents $C_1$-$C_6$-alkyl which can be substituted by trifluoromethyl, or R$^b$ represents $C_6$-$C_{10}$-aryl which can be substituted by $C_1$-$C_6$-alkyl, halogen, cyano, nitro or trifluoromethyl, a group of the formula —C(=O)—NR$^c$R$^d$ wherein R$^c$ represents hydrogen or $C_1$-$C_6$-alkyl, and R$^d$ represents $C_6$-$C_{10}$-aryl which can be substituted by $C_1$-$C_6$-alkoxycarbonyl or hydroxycarbonyl, a group of the formula —C(=O)—NR$^e$—OR$^f$ wherein R$^w$ and R$^f$ independently from each other represent hydrogen or $C_1$-$C_6$-alkyl, or $C_6$-$C_{10}$-arylalkoxy which, in the aryl part, can be substituted by halogen, $C_1$-$C_6$-alkyl, $C_1$-$C_6$-alkoxycarbonyl or hydroxycarbonyl, or R$^6$ represents $C_3$-$C_8$-cycloalkyl which can be substituted by up to three radicals independently selected from the group consisting of $C_1$-$C_6$-alkyl, hydroxy, oxo, $C_1$-$C_6$-alkoxycarbonyl and hydroxycarbonyl, $C_2$-$C_6$-alkenyl which can be substituted by $C_1$-$C_6$-alkoxycarbonyl or hydroxycarbonyl, $C_1$-$C_6$-alkyl or $C_1$-$C_6$-alkylcarbonyl which are substituted by $C_1$-$C_6$-alkoxycarbonylamino, $C_1$-$C_6$-alkoxycarbonyl which is substituted by phenyl-$C_1$-$C_6$-alkoxycarbonyl which for its part, in the phenyl moiety, can be further substituted by halogen, $C_1$-$C_6$-alkyl, $C_1$-$C_6$-alkoxycarbonyl or hydroxycarbonyl, or a group of the formula —SO$_2$—R$^g$ wherein R$^g$ represents $C_1$-$C_6$-alkyl which can be substituted by trifluoromethyl, or R$^g$ represents $C_6$-$C_{10}$-aryl which can be substituted by $C_1$-$C_6$-alkyl, halogen, cyano, nitro, trifluoromethyl, $C_1$-$C_6$-alkoxycarbonyl or hydroxycarbonyl, R$^7$ represents halogen, nitro, cyano, $C_1$-$C_6$-alkyl, hydroxy or $C_1$-$C_6$-alkoxy, wherein $C_1$-$C_6$-alkyl and $C_1$-$C_6$-alkoxy can be further substituted with one to three identical or different radicals selected from the group consisting of halogen, hydroxy and $C_1$-$C_4$-alkoxy, and $Y^1, Y^2, Y^3, Y^4$ and $Y^5$ independently from each other represent CH or N, wherein the ring contains either 0, 1 or 2 nitrogen atoms.

The compounds according to this invention can also be present in the form of their salts, hydrates and/or solvates.

Physiologically acceptable salts are preferred in the context of the present invention.

Physiologically acceptable salts according to the invention are non-toxic salts which in general are accessible by reaction of the compounds (I) with an inorganic or organic base or acid conventionally used for this purpose. Non-limiting examples of pharmaceutically acceptable salts of compounds (I) include the alkali metal salts, e.g. lithium, potassium and sodium salts, the alkaline earth metal salts such as magnesium and calcium salts, the quaternary ammonium salts such as, for example, triethyl ammonium salts, acetates, benzene sulphonates, benzoates, dicarbonates, disulphates, ditartrates, borates, bromides, carbonates, chlorides, citrates, dihydrochlorides, fumarates, gluconates, glutamates, hexyl resorcinates, hydrobromides, hydrochlorides, hydroxynaphthoates, iodides, isothionates, lactates, laurates, malates, maleates, mandelates, mesylates, methylbromides, methylnitrates, methylsulphates, nitrates, oleates, oxalates, palmitates, pantothenates, phosphates, diphosphates, polygalacturonates, salicylates, stearates, sulphates, succinates, tartrates, tosylates, valerates, and other salts used for medicinal purposes.

Hydrates of the compounds of the invention or their salts are stoichiometric compositions of the compounds with water, such as for example hemi-, mono-, or dihydrates.

Solvates of the compounds of the invention or their salts are stoichiometric compositions of the compounds with solvents.

The present invention includes both the individual enantiomers or diastereomers and the corresponding racemates or diastereomeric mixtures of the compounds according to the invention and their respective salts. In addition, all possible tautomeric forms of the compounds described above are included according to the present invention. The diastereomeric mixtures can be separated into the individual isomers by chromatographic processes. The racemates can be resolved into the respective enantiomers either by chromatographic processes on chiral phases or by resolution.

In the context of the present invention, the substituents, if not stated otherwise, in general have the following meaning:

Alkyl in general represents a straight-chain or branched saturated hydrocarbon radical having 1 to 6, preferably 1 to 4 carbon atoms. Non-limiting examples include methyl, ethyl, n-propyl, isopropyl, n-butyl, isobutyl, sec.-butyl, tert.-butyl, pentyl, isopentyl, hexyl, isohexyl. The same applies to radicals such as alkoxy, alkylamino, alkylthio, alkylcarbonyl, alkoxycarbonyl, alkoxy-carbonylamino and the like.

Alkanediyl in general represents a straight-chain or branched divalent alkane radical having 1 to 6, preferably 1 to 4 carbon atoms. Non-limiting examples include 1,2-ethylene, 1,3-propylene, propane-1,2-diyl, propane-2,2-diyl, 1,4-butylene, butane-1,3-diyl, butane-2,4-diyl, pentane-2,4-diyl, 2-methyl-pentane-2,4-diyl.

Alkenediyl in general represents a straight-chain or branched divalent alkene radical having 2 to 6, preferably 2 to 4 carbon atoms, and up to three double bonds. Non-limiting examples include ethene-1,2-diyl, ethene-1,1-diyl, propene-1,1-diyl, propene-1,2-diyl, propene-1,3-diyl, propene-3,3-diyl, propene-2,3-diyl, but-2-ene-1,4-diyl, 1,3-butadiene-1,4-diyl, pent-2-ene-1,4-diyl, hex-2-ene-1,4-diyl.

Alkoxy illustratively and preferably represents methoxy, ethoxy, n-propoxy, isopropoxy, tert.-butoxy, n-pentoxy and n-hexoxy.

Arylalkoxy and phenylalkoxy in general represent a straight-chain or branched alkoxy radical which is substituted with an aryl or a phenyl group, respectively. Non-limiting examples include benzyloxy, naphthylmethoxy, 1-phenylethoxy, 2-phenylethoxy, 2-naphthylethoxy, 3-phenylpropoxy, 4-phenylbutoxy. The same applies to the radical phenylalkoxycarbonyl.

Alkenoxy illustratively and preferably represents allyloxy, but-2-en-1-oxy, pent-3-en-1-oxy and hex-2-en-1-oxy.

Alkylcarbonyl in general represents a straight-chain or branched hydrocarbon radical having 1 to 6, preferably 1 to 4 carbon atoms which has a carbonyl function at the position of attachment. Non-limiting examples include formyl, acetyl, n-propionyl, n-butyryl, isobutyryl, pivaloyl, n-hexanoyl.

Alkylcarbonylamino in general represents a straight-chain or branched hydrocarbon radical having 1 to 6, preferably 1 to 4 carbon atoms which has a carbonylamino (—CO—NH—) function at the position of attachment and which is bonded to the carbonyl group. Non-limiting examples include formylamino, acetylamino, n-propionylamino, n-butyrylamino, isobutyrylamino, pivaloylamino, n-hexanoylamino. Alkoxycarbonyl illustratively and preferably represents methoxycarbonyl, ethoxycarbonyl, n-propoxycarbonyl, isopropoxycarbonyl, tert.-butoxycarbonyl, n-pentoxycarbonyl and n-hexoxycarbonyl.

Alkenoxycarbonyl illustratively and preferably represents allyloxycarbonyl, but-2-en-1-oxycarbonyl, pent-3-en-1-oxycarbonyl and hex-2-en-1-oxycarbonyl.

Alkylamino represents an alkylamino radical having one or two (independently selected) alkyl substituents, illustratively and preferably representing methylamino, ethylamino, n-propylamino, isopropylamino, tert.-butylamino, n-pentylamino, n-hexylamino, N,N-dimethylamino, N,N-diethylamino, N-ethyl-N-methylamino, N-methyl-N-n-propylamino, N-isopropyl-N-n-propylamino, N-tert.-butyl-N-methylamino, N-ethyl-N-n-pentylamino and N-n-hexyl-N-methylamino.

Alkylaminocarbonyl represents an alkylaminocarbonyl radical having one or two (independently selected) alkyl substituents, illustratively and preferably representing methylaminocarbonyl, ethylaminocarbonyl, n-propylaminocarbonyl, isopropylaminocarbonyl, tert.-butylaminocarbonyl, n-pentyl-aminocarbonyl, n-hexylaminocarbonyl, N,N-dimethylaminocarbonyl, N,N-diethylasninocarbonyl, N-ethyl-N-methylaminocarbonyl, N-methyl-N-n-propylaminocarbonyl, N-isopropyl-N-n-propylamino-carbonyl, N-tert.-butyl-N-methylaminocarbonyl, N-ethyl-N-n-pentylaminocarbonyl and N-n-hexyl-N-methylaminocarbonyl.

Alkylsulfonyl in general represents a straight-chain or branched hydrocarbon radical having 1 to 6, preferably 1 to 4 carbon atoms which has a sulfonyl function at the position of attachment. Non-limiting examples include methylsulfonyl, ethylsulfonyl, n-propylsulfonyl, isopropylsulfonyl, n-butylsulfonyl, tert.-butylsulfonyl.

Cycloalkyl in general represents a cyclic saturated hydrocarbon radical having 3 to 8, preferably 3 to 6 carbon atoms. Non-limiting examples include cyclopropyl, cyclobutyl, cyclopentyl, cyclohexyl and cycloheptyl. The same applies to radicals such as cycloalkylcarbonyl.

Aryl in general represents a mono- to tricyclic aromatic carbocyclic radical having 6 to 14, preferably 6 to 10 carbon atoms, illustratively and preferably representing phenyl, naphthyl and phenanthrenyl. The same applies to radicals such as arylcarbonyl, arylalkoxy and arylaminocarbonyl.

Arylcarbonyl illustratively and preferably represents benzoyl and naphthoyl.

Arylaminocarbonyl illustratively and preferably represents phenylaminocarbonyl and naphthylaminocarbonyl.

Heteroaryl per se and in heteroarylcarbonyl in general represents an aromatic mono- or bicyclic radical having 5 to 10 and preferably 5 or 6 ring atoms, and up to 5 and preferably up to 4 hetero-atoms selected from the group consisting of S, O and N, illustratively and preferably representing thienyl, furyl, pyrrolyl, thiazolyl, oxazolyl, isothiazolyl, isoxazolyl, imidazolyl, oxadiazolyl, thiadiazolyl, pyridyl, pyrimidyl, pyridazinyl, indolyl, indazolyl, benzofuranyl, benzothienyl, benzothiazolyl, quinolinyl, isoquinolinyl.

Heteroarylcarbonyl illustratively and preferably represents thienylcarbonyl, furylcarbonyl, pyrrolyl-carbonyl, thiazolyl-carbonyl, oxazolylcarbonyl, isothiazolylcarbonyl, isoxazolylcarbonyl, imidazolylcarbonyl, pyridylcarbonyl, pyrimidylcarbonyl, pyridazinylcarbonyl, indolylcarbonyl, indazolyl-carbonyl, benzofuranylcarbonyl, benzothienylcarbonyl, quinolinylcarbonyl, isoquinolinylcarbonyl.

Heterocyclyl per se and in heterocyclylcarbonyl in general represents a mono- or polycyclic, preferably mono- or bicyclic, non-aromatic heterocyclic radical having 4 to 10 and preferably 5 to 8 ring atoms, and up to 3 and preferably up to 2 heteroatoms and/or hetero-groups selected from the group consisting of N, O, S, SO and $SO_2$. The heterocyclyl radicals can be saturated or partially unsaturated. Preference is given to 5- to 8-membered monocyclic saturated heterocyclyl radicals having up to two heteroatoms selected from the group consisting of O, N and S; such as illustratively and preferably tetrahydrofuran-2-yl, pyrrolidin-1-yl, pyrrolidin-2-yl, pyrrolidin-3-yl, pyrrolinyl, piperidinyl, piperazinyl, morpholinyl, thiomorpholinyl, perhydroazepinyl.

Heterocyclylcarbonyl illustratively and preferably represents tetrahydrofuran-2-carbonyl, pyrrolidine-1-carbonyl, pyrrolidine-2-carbonyl, pyrrolidine-3-carbonyl, pyrrolinecarbonyl, piperidine-carbonyl, morpholinecarbonyl, perhydroazepinecarbonyl.

Halogen represents fluorine, chlorine, bromine and iodine.

When stated, that $Y^1$, $Y^2$, $Y^3$, $Y^4$ and $Y^5$ represent CH or N. CH shall also stand for a ring carbon atom, which is substituted with a substituent $R^3$ or $R^7$.

A * symbol next to a bond denotes the point of attachment in the molecule.

In another preferred embodiment, the present invention relates to compounds of general formula (I), wherein A represents an aryl or heteroaryl ring, $R^1$, $R^2$ and $R^3$ independently from each other represent hydrogen, halogen, nitro, cyano, $C_1$-$C_6$-alkyl, hydroxy or $C_1$-$C_6$-alkoxy, wherein $C_1$-$C_6$-alkyl and $C_1$-$C_6$-alkoxy can be further substituted with one to three identical or different radicals selected from the group consisting of halogen, hydroxy and $C_1$-$C_4$-alkoxy, $R^4$ represents $C_1$-$C_6$-alkylcarbonyl, $C_1$-$C_6$-alkoxycarbonyl, $C_2$-$C_6$-alkenoxycarbonyl, hydroxy-carbonyl, aminocarbonyl, mono- or di-$C_1$-$C_4$-alkylaminocarbonyl, $C_6$-$C_{10}$-arylamino-carbonyl, heteroarylcarbonyl, heterocyclylcarbonyl, heteroaryl, heterocyclyl or cyano, wherein $C_1$-$C_6$-alkylcarbonyl, $C_1$-$C_6$-alkoxycarbonyl, mono- and di-$C_1$-$C_4$-alkylaminocarbonyl can be further substituted with one to three identical or different radicals selected from the group consisting of $C_3$-$C_8$-cycloalkyl, hydroxy, $C_1$-$C_4$-alkoxy, $C_1$-$C_4$-alkoxycarbonyl, hydroxycarbonyl, aminocarbonyl, mono- and di-$C_1$-$C_4$-alkylaminocarbonyl, $C_1$-$C_4$-alkylcarbonylamino, amino, mono- and di-$C_1$-$C_4$-alkylamino, heteroaryl, heterocyclyl and tri-($C_1$-$C_6$-alkyl)-silyl, $R^5$ represents $C_1$-$C_4$-alkyl, which can be substituted with one to three identical or different radicals selected from the group consisting of halogen, hydroxy, $C_1$-$C_6$-alkoxy, $C_2$-$C_6$-alkenoxy, $C_1$-$C_6$-alkylthio, amino, mono- and di-$C_1$-$C_6$-alkylamino, arylamino, hydroxycarbonyl, $C_1$-$C_6$-alkoxycarbonyl and the radical —O—$C_1$-$C_4$-alkyl-O—$C_1$-$C_4$-alkyl, $R^6$ represents
  a group of the formula -T-U wherein
  T represents a $C_1$-$C_4$-alkanediyl or $C_2$-$C_4$-alkenediyl group
  and
  U represents
    $C_6$-$C_{10}$-aryl or 5- or 6-membered heteroaryl each of which is substituted by one, two or three radicals independently selected from the group consisting of halogen, $C_1$-$C_6$-alkyl, 5- or 6-membered heteroaryl and a group of the formula —V—W wherein V represents a bond, a $C_2$-$C_6$-alkenediyl group or a $C_1$-$C_6$-alkanediyl group the latter of which can be further substituted by $C_3$-$C_8$-cycloalkyl, and W represents $C_1$-$C_6$-alkoxycarbonyl or hydroxycarbonyl, a group of the formula —C(=O)—NH—SO$_2$—R$^b$ wherein R$^b$ represents C$_1$-C$_6$-alkyl which can be substituted by trifluoromethyl, or R$^b$ represents C$_6$-C$_{10}$-aryl which can be substituted by C$_1$-C$_6$-alkyl, halogen, cyano, nitro or trifluoromethyl, or a group of the formula —C(=O)NHR$^d$ wherein R$^d$ represents C$_6$-C$_{10}$-aryl which can be substituted by C$_1$-C$_6$-alkoxycarbonyl or hydroxycarbonyl, or R$^6$ represents C$_3$-C$_8$-cycloalkyl which can be substituted by up to three radicals independently selected from the group consisting of C$_1$-C$_6$-alkyl, hydroxy, oxo, C$_1$-C$_6$-alkoxycarbonyl and hydroxycarbonyl, or C$_2$-C$_6$-alkenyl which can be substituted by C$_1$-C$_6$-alkoxycarbonyl or hydroxycarbonyl, R$^7$ represents halogen, nitro, cyano, C$_1$-C$_6$-alkyl, hydroxy or C$_1$-C$_6$-alkoxy, wherein C$_1$-C$_6$-alkyl and C$_1$-C$_6$-alkoxy can be further substituted with one to three identical or different radicals selected from the group consisting of halogen, hydroxy and C$_1$-C$_4$-alkoxy, and Y$^1$, Y$^2$, Y$^3$, Y$^4$ and Y$^5$ independently from each other represent CH or N, wherein the ring contains either 0, 1 or 2 nitrogen atoms.

In another particularly preferred embodiment, the present invention relates to compounds of general formula (I), wherein A represents a phenyl, naphthyl or pyridyl ring, R$^1$, R$^2$ and R$^3$ independently from each other represent hydrogen, fluoro, chloro, bromo, nitro, cyano, methyl, ethyl, trifluoromethyl or trifluoromethoxy, R$^4$ represents C$_1$-C$_6$-alkylcarbonyl, C$_1$-C$_6$-alkoxycarbonyl, allyloxycarbonyl, hydroxycarbonyl, aminocarbonyl, mono-C$_1$-C$_4$-alkylaminocarbonyl, furylcarbonyl, pyridylcarbonyl or cyano, wherein C$_1$-C$_6$-alkylcarbonyl, C$_1$-C$_6$-alkoxycarbonyl and mono-C$_1$-C$_4$-alkylaminocarbonyl can be substituted with one to three identical or different radicals selected from the group consisting of C$_3$-C$_6$-cycloalkyl, hydroxy, C$_1$-C$_4$-alkoxy, C$_1$-C$_4$-alkoxycarbonyl, hydroxy-carbonyl, amino, mono- and di-C$_1$-C$_4$-alkylamino, R$^5$ represents methyl or ethyl, R$^6$ represents a group of the formula -T-U wherein T represents a C$_1$-C$_4$-alkanediyl group and U represents phenyl, furyl, thienyl, oxazolyl, thiazolyl or pyridyl each of which is substituted by one or two radicals independently selected from the group consisting of fluoro, chloro, bromo, C$_1$-C$_4$-alkyl, thienyl, pyridyl and a group of the formula —V—W wherein V represents a bond or a C$_1$-C$_4$-alkanediyl or C$_2$-C$_4$-alkenediyl group, and W represents C$_1$-C$_4$alkoxycarbonyl or hydroxycarbonyl, a group of the formula —C(=O)—NH—SO$_2$—R$^b$ wherein R$^b$ represents C$_1$-C$_4$-alkyl which can be substituted by trifluoromethyl, or R$^b$ represents phenyl which can be substituted by C$_1$-C$_4$-alkyl, fluoro, chloro, bromo, cyano, nitro or trifluoromethyl, or a group of the formula —C(=O)—NHR$^d$ wherein R$^d$ represents phenyl which can be substituted by C$_1$-C$_4$-alkoxycarbonyl or hydroxycarbonyl, or R$^6$ represents C$_3$-C$_6$-cycloalkyl which can be substituted by up to two radicals independently selected from the group consisting of C$_1$-C$_4$-alkyl, hydroxy, oxo, C$_1$-C$_4$-alkoxycarbonyl and hydroxycarbonyl, or C$_2$-C$_4$-alkenyl which is substituted by C$_1$-C$_4$-alkoxycarbonyl or hydroxycarbonyl, R$^7$ represents halogen, nitro, cyano, trifluoromethyl, trifluoromethoxy, methyl or ethyl, and Y$^1$, Y$^2$, Y$^3$, Y$^4$ and Y$^1$ each represent CH.

In another very particularly preferred embodiment, the present invention relates to compounds of general formula (I), wherein A represents a phenyl or a pyridyl ring, R$^1$ and R$^3$ each represent hydrogen, R$^2$ represents fluoro, chloro, bromo, nitro or cyano, R$^4$ represents cyano, hydroxycarbonyl, furylcarbonyl, pyridylcarbonyl, C$_1$-C$_4$-alkylcarbonyl or C$_1$-C$_4$-alkoxycarbonyl, wherein C$_1$-C$_4$-alkylcarbonyl and C$_1$-C$_4$-alkoxycarbonyl can be substituted with a radical selected from the group consisting of hydroxy, C$_1$-C$_4$-alkoxy, C$_1$-C$_4$alkoxycarbonyl, hydroxycarbonyl, mono- and di-C$_1$-C$_4$-alkylamino, R$^5$ represents methyl, R$^6$ represents a group of the formula -T-U wherein T represents a —CH$_2$— group and U represents phenyl, furyl or oxazolyl each of which is substituted by one or two radicals independently selected from the group consisting of fluoro, chloro, bromo, C$_1$-C$_4$-alkyl and a group of the formula —V—W wherein V represents a bond, a —CH$_2$-group or a —CH=CH— group, and W represents C$_1$-C$_4$-alkoxycarbonyl or hydroxy-carbonyl, a group of the formula —C(=O)—NH—SO$_2$—R$^b$ wherein R$^b$ represents C$_1$-C$_4$-alkyl which can be substituted by trifluoromethyl, or R$^b$ represents phenyl which can be substituted by C$_1$-C$_4$-alkyl, fluoro, chloro, bromo, cyano, nitro or trifluoromethyl, Or a group of the formula —C(=O)—NHR$^d$ wherein R$^d$ represents phenyl which can be substituted by C$_1$-C$_4$-alkoxycarbonyl or hydroxycarbonyl, Or R$^6$ represents —C$_3$-C$_6$-cycloalkyl which can be substituted by up to two radicals independently selected from the group consisting of C$_1$-C$_4$-alkyl, hydroxy, oxo, C$_1$-C$_4$-alkoxycarbonyl and hydroxycarbonyl, or a —CH=CH— group which is substituted by C$_1$-C$_4$-alkoxycarbonyl or hydroxycarbonyl, R$^7$ represents trifluoromethyl or nitro, and Y$^2$, Y$^3$, Y$^4$ and Y$^1$ each represent CH.

In another likewise preferred embodiment, the present invention relates to compounds according to general formula (I), wherein A is phenyl or pyridyl.

In another likewise preferred embodiment, the present invention relates to compounds according to general formula (I), wherein R$^1$ is hydrogen.

In another likewise preferred embodiment, the present invention relates to compounds according to general formula (I), wherein R$^2$ is cyano, especially wherein A is phenyl or pyridyl and $R^2$ is cyano located in para-position relative to the central dihydropyrimidinone ring.

In another likewise preferred embodiment, the present invention relates to compounds according to general formula (I), wherein $R^3$ is hydrogen.

In another likewise preferred embodiment, the present invention relates to compounds according to general formula (I), wherein $R^4$ is $C_1$-$C_4$-alkoxycarbonyl optionally substituted by hydroxy, especially 2-hydroxyethoxycarbonyl, or wherein $R^4$ is $C_1$-$C_4$-alkylcarbonyl, especially acetyl, or wherein $R^4$ is hydroxycarbonyl or cyano.

In another likewise preferred embodiment, the present invention relates to compounds according to general formula (I), wherein $R^5$ is methyl.

In another likewise preferred embodiment, the present invention relates to compounds according to general formula (I), wherein $R^7$ is trifluoromethyl or nitro, especially wherein $R^7$ is trifluoromethyl located in meta-position relative to the central dihydropyrimidinone ring.

In another likewise particularly preferred embodiment, the present invention relates to compounds of general formula (IA)

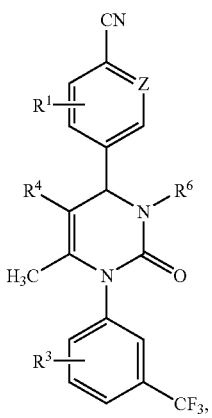

(IA)

wherein

Z represents CH or N, and $R^1$, $R^3$, $R^4$ and $R^6$ have the meaning indicated above.

In another embodiment, the present invention relates to a process for synthesizing the compounds of general formula (I) or (IA), respectively.

The compounds of general formula (I) or (IA), respectively, can be synthesized by condensing compounds of general formula (II)

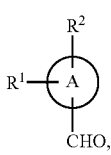

(II)

wherein A, $R^1$ and $R^2$ have the meaning indicated above, with compounds of general formula (III)

(III)

wherein $R^4$ and $R^5$ have the meaning indicated above, and compounds of general formula (IV)

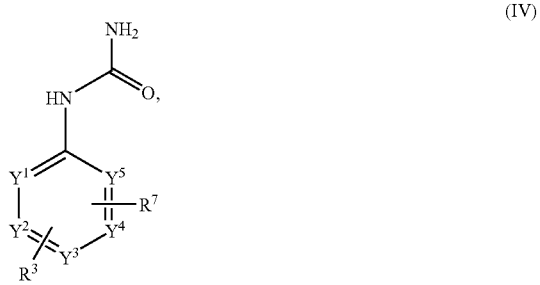

(IV)

wherein $R^3$, $R^7$, and $Y^1$ to $Y^5$ have the meaning indicated above, in the presence of an acid either in a three-component/one-step reaction or sequentially to give compounds of general formula (IB)

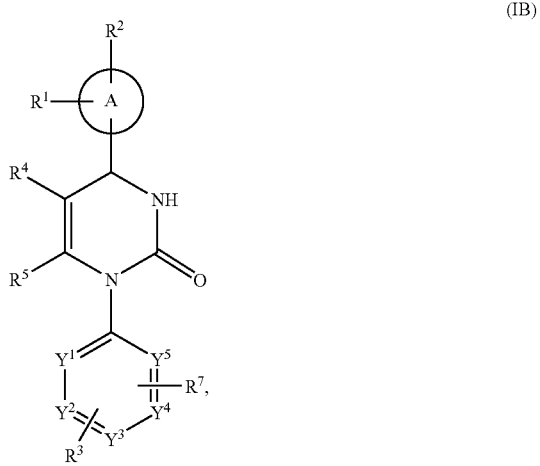

(IB)

wherein A, $R^1$ to $R^5$, $R^7$, and $Y^1$ to $Y^5$ have the meaning indicated above, followed by reaction of the compounds of general formula (IB) with compounds of general formula (V)

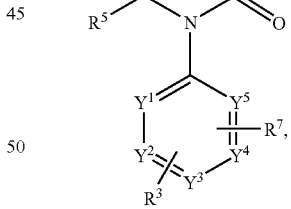

$R^6$—X (V), wherein $R^6$ has the meaning indicated above, and

X represents a leaving group, such as halogen, tosylate, mesylate or sulfate, in the presence of a base.

The compounds of general formula (IB), wherein $R^4$ represents cyano and $R^5$ represents amino, can alternatively be prepared by condensing compounds of general formula (II)

with compounds of general formula (IV) and the compound of formula (VI)

NC—CH$_2$—CN  (VI)

in the presence of an acid either in a three-component/one-step reaction or sequentially.

Suitable solvents for the process (II)+(III)/(VI)+(IV)→(IB) are generally customary organic solvents which do not change under the reaction conditions. These include ethers such as diethyl ether, diisopropyl ether, methyl t-butyl ether, 1,2-dimethoxyethane, dioxan or tetrahydrofuran, ethyl acetate, acetone, acetonitrile, dimethylsulfoxide, dimethylformamide, or alcohols such as methanol, ethanol, n-propanol, isopropanol, n-butanol or t-butanol, or hydrocarbons such as pentane, hexane, cyclohexane, benzene, toluene or xylene, or halogeno-hydrocarbons such as di-chloromethane, dichloroethane, trichloromethane or chlorobenzene. It is also possible to use mixtures of the above-mentioned solvents. Preferred for the process is tetrahydrofuran or dioxan.

Suitable acids for the process (II)+(III)/(VI)+(IV)→(IB) are generally inorganic or organic acids or acid, anhydrides. These preferably include carboxylic acids, such as, for example, acetic acid or trifluoroacetic acid, sulfonic acids, such as, for example, methanesulfonic acid or p-toluenesulfonic acid, hydrochloric acid or phosphoric or phosphonic acids or anhydrides, such as polyphosphoric acid or propanephosphonic acid anhydride. Preference is given to polyphosphoric acid ethyl ester. The acid is employed in an amount from 0.25 mol to 100 mol, relative to 1 mol of the compound of the general formula (II).

The process is in general carried out in a temperature range from +20° C. to +150° C., preferably from +60° C. to +100° C.

The process is generally carried out at normal pressure. However, it is also possible to carry it out at elevated pressure or at reduced pressure (for example in a range from 0.5 to 5 bar).

Suitable solvents for the process (IB)+(V)→(I) are generally customary organic solvents which do not change under the reaction conditions. These include ethers such as diethyl ether, diisopropyl ether, 1,2-dimethoxyethane, dioxan or tetrahydrofuran, ethyl acetate, acetone, acetonitrile, dimethylsulfoxide, dimethylformamide, or hydrocarbons such as pentane, hexane, cyclohexane, benzene, toluene or xylene, or halogeno-hydrocarbons such as dichloromethane, dichloroethane, trichloromethane or chlorobenzene. It is also possible to use mixtures of the above-mentioned solvents. Preferred for the process is tetrahydrofuran or dimethylformamide.

Suitable bases for the process (IB)+(V)→(I) are generally inorganic or organic bases. These preferably include alkali carbonates such as sodium or potassium carbonate or hydrogencarbonate, cyclic amines such as, for example, N-methylmorpholine, N-methylpiperidine, pyridine or 4-N,N-dimethylaminopyridine, or ($C_1$-$C_4$)-trialkylamines such as, for example, triethylamine or diisopropylethylamine, or alkali hydrides such as sodium or potassium hydride. Preference is given to potassium carbonate or sodium hydride. The base is employed in an amount from 0.1 mol to 10 mol, preferably from 1 mol to 3 mol, relative to 1 mol of the compound of general formula (IV).

The process is in general carried out in a temperature range from 0° C. to +150° C., preferably from +20° C. to +80° C., especially at room temperature.

The process is generally carried out at normal pressure. However, it is also possible to carry it out at elevated pressure or at reduced pressure (for example in a range from 0.5 to 5 bar).

The compounds of the general formulas (I), (III), (IV), (V) and (VI) are known per se, or they can be prepared by customary methods.

The compounds of the present invention can also be prepared, if appropriate, by functional group transformations of individual substituents, especially those listed under $R^4$ and $R^6$, of the compounds of general formula (I) obtained by the process mentioned above. These transformations are carried out using standard synthetic methods, e.g. by esterification, ester cleavage/hydrolysis, amide formation, catalytic hydrogenation, alkylation and/or aryl coupling reactions. The above-mentioned process can be illustrated by the following scheme:

Scheme

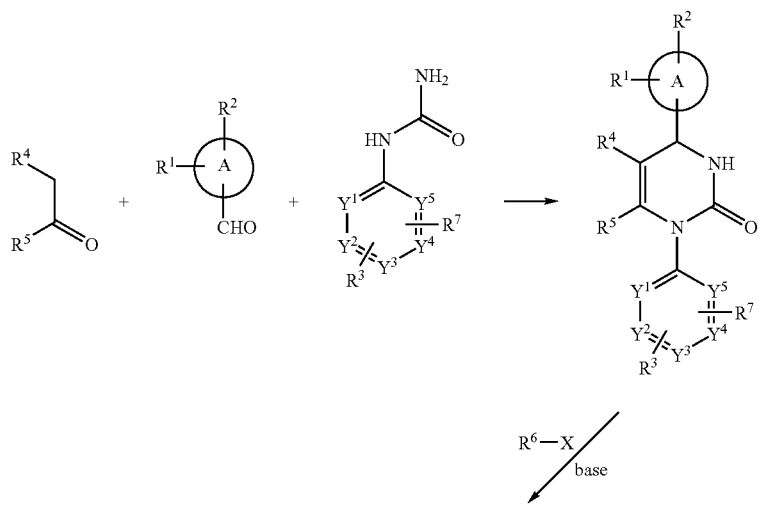

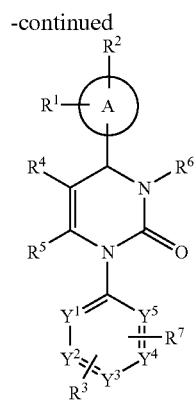

The compounds according to the invention exhibit an unforeseeable, useful pharmacological and pharmacokinetic activity spectrum. They are therefore suitable for use as medicaments for the treatment and/or prophylaxis of disorders in humans and animals.

Surprisingly, the compounds of the present invention show human neutrophil elastase (HNE) inhibitory activity and are therefore suitable for the preparation of medicaments for the treatment of diseases associated with HNE activity. They may thus provide an effective treatment of acute and chronic inflammatory processes, such as rheumatoid arthritis, atherosclerosis, and especially of acute and chronic pulmonary diseases, such as lung fibrosis, cystic fibrosis, pneumonia, acute respiratory distress syndrome (ARDS), in particular pulmonary emphysema, including smoking-induced emphysema, and chronic obstructive pulmonary diseases (COPD), chronic bronchitis and bronchiectasis. The compounds of the present invention may further provide an effective treatment for cardiovascular ischaemic diseases such as acute coronary syndrome, acute myocardial infarction, unstable and stable angina pectoris, coronary artery bypass grafts (CABG) and heart failure development, for atherosclerosis, mitral valvular disease, atrial septal defects, percutaneous transluminal coronary angioplasty (PTCA), inflammation after open heart surgery and for pulmonary hypertension. They may also prove useful for an effective treatment of rheumatoid arthritis, acute inflammatory arthritis, cancer, acute pancreatitis, ulcerative colitis, periodontal disease, Chury-Strauss syndrome, acute and chronic atopic dermatitis, psoriasis, systemic lupus erythematosus, bullous pemphigus, sepsis, alcoholic hepatitis, liver fibrosis, Behcet's disease, allergic fungal sinusitis, allergic sinusitis, Crohn's disease, Kawasaki disease, glomerulonephritis, acute pyelonephritis, colorectal diseases, chronic suppurative otitis media, chronic venous leg ulcers, inflammatory bowel disease, bacterial and viral infections, brain trauma, stroke and other conditions in which neutrophil participation is involved.

The present invention further provides medicaments containing at least one compound according to the invention, preferably together with one or more pharmacologically safe excipient or carrier substances, and also their use for the above-mentioned purposes.

The active component can act systemically and/or locally. For this purpose, it can be applied in a suitable manner, for example orally, parenterally, pulmonally, nasally, sublingually, lingually, buccally, rectally, transdermally, conjunctivally, optically or as an implant.

For these application routes, the active component can be administered in suitable application forms.

Useful oral application forms include application forms which release the active component rapidly and/or in modified form, such as for example tablets (non-coated and coated tablets, for example with an enteric coating), capsules, sugar-coated tablets, granules, pellets, powders, emulsions, suspensions, solutions and aerosols.

Parenteral application can be carried out with avoidance of an absorption step (intravenously, intraarterially, intracardially, intraspinally or intralumbarly) or with inclusion of an absorption (intramuscularly, subcutaneously, intracutaneously, percutaneously or intraperitoneally). Useful parenteral application forms include injection and infusion preparations in the form of solutions, suspensions, emulsions, lyophilisates and sterile powders.

Forms suitable for other application routes include for example inhalatory pharmaceutical forms (including powder inhalers, nebulizers), nasal drops/solutions, sprays; tablets or capsules to be administered lingually, sublingually or buccally, suppositories, ear and eye preparations, vaginal capsules, aqueous suspensions (lotions, shake mixtures), lipophilic suspensions, ointments, creams, milk, pastes, dusting powders or implants.

The active components can be converted into the recited application forms in a manner known per se. This is carried out using inert non-toxic, pharmaceutically suitable excipients. These include inter alia carriers (for example microcrystalline cellulose), solvents (for example liquid poly-ethylene glycols), emulsifiers (for example sodium dodecyl sulphate), dispersing agents (for example polyvinylpyrrolidone), synthetic and natural biopolymers (for example albumin), stabilizers (for example antioxidants such as ascorbic acid), colorants (for example inorganic pigments such as iron oxides) or taste and/or odor corrigents.

For human use, in the case of oral administration, it is recommendable to administer doses of from 0.001 to 50 mg/kg, preferably of 0.01 mg/kg to 20 mg/kg. In the case of parenteral administration, such as, for example, intravenously or via mucous membranes nasally, buccally or inhalationally, it is recommendable to use doses of 0.001 mg/kg to 0.5 mg/kg.

In spite of this, it can be necessary in certain circumstances to depart from the amounts mentioned, namely as a function of body weight, application route, individual behaviour towards the active component, manner of preparation and time or interval at which application takes place. It can for instance be sufficient in some cases to use less than the aforementioned minimum amount, while in other cases the upper limit mentioned will have to be exceeded. In the case of the application of larger amounts, it can be advisable to divide them into a plurality of individual doses spread through the day.

The percentages in the tests and examples which follows are, unless otherwise stated, by weight; parts are by weight. Solvent ratios, dilution ratios and concentrations reported for liquid/liquid solutions are each based on the volume.

A. Evaluation of Physiological Activity

The potential of the compounds of the invention to inhibit neutrophil elastase activity may be demonstrated, for example, using the following assays:

I. In Vitro Enzyme Assays of Human Neutrophil Elastase (HNE)

Assay Contents:
assay buffer: 0.1 M HEPES-NaOH buffer pH 7.4, 0.5 M NaCl, 0.1% (w/v) bovine serum albumin;
suitable concentration (see below) of HNE (18 U/mg lyophil., #20927.01, SERVA Electrophoresis GmbH, Heidelberg, Germany) in assay buffer;
suitable concentration (see below) of substrate in assay buffer;
suitable concentration of test compounds diluted with assay buffer from a 10 mM stock solution in DMSO.

Example I-A

In Vitro Inhibition of HNE Using a Fluorogenic Peptide Substrate (Continuous Read-Out Signal, 384 MTP Assay Format)

In this protocol, the elastase substrate MeOSuc-Ala-Ala-Pro-Val-AMC (#324740, Calbiochem-Novabiochem Corporation, Merck KGaA, Darmstadt, Germany) is used.

The test solution is prepared by mixing 10 µl of test compound dilution, 20 µl of HNE enzyme dilution (final concentration 8-0.4 µU/ml, routinely 2.1 µU/ml) and 20 µl of substrate dilution (final concentration 1 mM-1 µM, routinely 20 µM), respectively. The solution is incubated for 0-2 hrs at 37° C. (routinely one hour). The fluorescence of the liberated AMC due to the enzymatic reaction is measured at 37° C. (TECAN spectra fluor plus plate reader). The rate of increase of the fluorescence (ex. 395 nm, em. 460 nm) is proportional to elastase activity. $IC_{50}$ values are determined by RFU-versus-[I] plots. $K_m$ and $K_m$(app.) values are determined by Lineweaver-Burk plots and converted to $K_i$ values by Dixon plots.

The preparation examples (and also some intermediates) have $IC_{50}$ values within the range of 5 nM-5 µM in this assay. Representative data are given in Table 1:

TABLE 1

| Example No. | $IC_{50}$ [nM] |
|---|---|
| 19A | 70 |
| 21A | 60 |
| 24A | 9 |
| 29A | 20 |
| 31A | 10 |
| 1 | 30 |
| 19 | 20 |
| 22 | 8 |
| 24 | 10 |
| 39 | 120 |
| 44 | 30 |

TABLE 1-continued

| Example No. | $IC_{50}$ [nM] |
|---|---|
| 55 | 20 |
| 61 | 130 |
| 67 | 70 |
| 74 | 10 |

Example I-B

In Vitro Inhibition of HNE Using a Fluorogenic, Unsoluble Elastin Substrate (Discontinuous Read-Out Signal, 96 Mtp Assay Format)

In this protocol the elastase substrate elastin-fluorescein (#100620, ICN Biomedicals GmbH, Eschwege, Germany) is used. The test solution is prepared by mixing 3 µl of test compound dilution, 77 µl of HNE enzyme dilution (final concentration 0.22 U/ml-2.2 mU/ml, routinely 21.7 µU/ml) and 80 µl substrate suspension (final concentration 2 mg/ml). The suspension is incubated for 0-16 hrs at 37° C. (routinely four hours) under slightly shaking conditions. To stop the enzymatic reaction, 160 µl of 0.1 M acetic acid are added to the test solution (final concentration 50 mM). The polymeric elastin-fluorescein is pulled down by centrifugation (Eppendorf 5804 centrifuge, 3.000 rpm, 10 min). The supernatant is transferred into a new MTP and the fluorescence of the liberated peptide fluorescein due to the enzymatic reaction is measured (BMG Fluostar plate reader). The rate of fluorescence (ex. 490 nm, em. 520 nm) is proportional to elastase activity. $IC_{50}$ values are determined by RFU-versus-[I] plots.

II. In Vitro Human Neutrophil Assays

Example II-A

In Vitro PMN Elastolysis Assay

This assay is used to determine the elastolytic potential of human polymorphonuclear cells (PMNs) and assess the proportion of degradation due to neutrophil elastase [cf. Z. W. She et al., Am. J. Respir. Cell. Mol. Biol. 9386-392 (1993)]. Tritiated elastin, in suspension, is coated on to a 96 well plate at 10 µg per well. Test and reference [ZD-0892 (J. Med. Chem. 40, 1876-1885, 3173-3181 (1997), WO 95/21855) and α1 protease inhibitor (α1PI)] compounds are added to the wells at the appropriate concentrations. Human PMNs are separated from peripheral venous blood of healthy donors and resuspended in culture media. The neutrophils are added to the coated wells at concentrations ranging between $1\times10^6$ to $1\times10^6$ cells per well. Porcine pancreatic elastase (1.3 µM) is used as a positive control for the assay, and α1PI (1.2 µM) is used as the positive inhibitor of neutrophil elastase. The cellular control is PMNs without compound at each appropriate cell density. The cells plus compounds are incubated in a humidified incubator at 37° C. for 4 hours. The plates are centrifuged to allow the harvest of cell supernatant only. The supernatant is transferred in 75 µl volumes to corresponding wells of a 96 well Lumaplate™ (solid scintillant containing plates). The plates are dried until no liquid is visible in the wells and read in a beta counter for 3 minutes per well.

Elastolysis of the $^3$H-elastin results in an increase in counts in the supernatant. An inhibition of this elastolysis shows a decrease, from the cellular control, of tritium in the supernatant. α1PI gave 83.46±3.97% (mean±s.e.m.) inhibition at 1.2 µM (n=3 different donors at $3.6\times10^5$ cells per well). $IC_{50}$ values were obtained for the reference compound ZD-0892 of 45.50±7.75 nM (mean±s.e.m.) (n=2 different donors at 3.6× $10^5$ cells per well).

Given that ZD-0892 is a selective inhibitor of PMN elastase along with the data from α1PI inhibition, these results indicate that the majority of elastin degradation by PMNs is due to the release of neutrophil elastase, and not to another elastolytic enzyme such as matrix metalloproteases (MMPs). The compounds of this invention are evaluated for their inhibitory activity in this HNE-dependent model of neutrophil elastolysis.

Example II-B

In Vitro Inhibition of Membrane Bound Elastase

Measurement of the inhibition of elastase bound to neutrophil membranes is performed using a human neutrophil assay. Neutrophils are stimulated with LPS at 37° C. for 35 min and then spun at 1600 rpm. Subsequently, the membrane bound elastase is fixed to the neutrophils with 3% paraformaldehyde and 0.25% glutaraldehyde for 3 min at 4° C. The neutrophils are then spun, and vehicle and the compound under evaluation are added, followed by addition of the substrate MeO-Suc-Ala-Ala-Pro-Val-AMC (#324740, Calbiochem-Novabiochem Corporation, Merck KGaA, Darmstadt, Germany) at 200 A. Following a 25 min incubation at 37° C., the reaction is terminated with PMSF (phenylmethanesulfonyl fluoride), and the fluorescence is read at ex: 400 nm and em: 505 nm. $IC_{50}$ values are determined by interpolation from plots of relative fluorescence vs. inhibitor concentration.

III. In Vivo Models

Example III-A

In Vivo Model of Acute Lung Injury in the Rat

Instillation of human neutrophil elastase (HNE) into rat lung causes acute lung damage. The extent of this injury can be assessed by measuring lung haemorrhage.

Rats are anaesthetised with Hypnorm/Hypnovel/water and instilled with HNE or saline delivered by microsprayer into the lungs. Test compounds are administered by intravenous injection, by oral gavage or by inhalation at set times prior to the administration of HNE. Sixty minutes after the administration of elastase animals are killed by an anaesthetic overdose (sodium pentobarbitone) and the lungs lavaged with 2 ml heparinised phosphate buffered saline (PBS). Bronchoalveolar lavage (BAL) volume is recorded and the samples kept on ice. Each BAL sample is centrifuged at 900 r.p.m. for 10 minutes at 4-10° C. The supernatant is discarded and the cell pellet resuspended in PBS and the sample spun down again. The supernatant is again discarded and the cell pellet resuspended in 1 ml 0.1% cetyltrimethyl-ammonium bromide (CTAB)/PBS to lyse the cells. Samples are frozen until blood content is assayed. Prior to the haemorrhage assay the samples are defrosted and mixed. 100 µl of each sample are placed into a separate well of a 96 well flat-bottomed plate. All samples are tested in duplicate. 100 III 0.1% CTAB/PBS is included as a blank. The absorbance of the well contents is measured at 415 nm using a spectrophotometer. A standard curve is constructed by measuring the OD at 415 nm of different concentrations of blood in 0.1% CTAB/PBS. Blood content values are calculated by comparison to the standard curve (included in each plate) and normalised for the volume of BAL fluid retrieved.

The compounds of this invention are evaluated intravenously, orally or by inhalation for their inhibitory activity in this model of HNE-induced haemorrhage in the rat.

Example III-B

In Vivo Model of Acute Myocardial Infarction in the Rat

Elastase inhibitors are tested in a rat thread infarct model. Male Wistar rats (weighing>300 g) receive 10 mg/kg aspirin 30 min prior to surgery. They are anaesthetized by isofluran and ventilated (120-130 strokes/min, 200-250 µl stroke volume; MiniVent Type 845, Hugo Sachs Elektronik, Germany) during the whole surgery. Following a left thoracotomy at the fourth intercostal space, the pericardium is opened and the heart briefly exteriorized. A thread is turned around the left coronary artery (LAD) without occluding the artery. The thread is passed under the skin to the neck of the animal. The thorax is closed and the animal is allowed to recover for 4 days. At the fifth day, rats are anaesthetized with ether for 3 min, and the thread is tied and the LAD occluded under ECG control. Test compounds are administered before or after LAD occlusion per os, intraperitoneally or intravenously (bolus or permanent infusion). After 1 hr occlusion, the thread is reopened to allow reperfusion. Hearts are excised, and infarct sizes are determined 48 hours later by staining of the re-occluded hearts with Evans blue, followed by TTC (triphenyltetrazolium chloride) staining of 2 mm heart sections. Normoxic (not occluded tissue) areas stain blue, ischemic (occluded but surviving tissue) areas stain red and necrotic (occluded dead tissue) areas remain white. Each tissue section is scanned and infarct sizes are determined by computer planimetry.

B. Examples

Abbreviations:

| | |
|---|---|
| aq. | aqueous |
| c | concentration |
| conc. | concentrated |
| DMF | N,N-dimethylformamide |
| DMSO | dimethylsulfoxide |
| EI | electron impact ionization (for MS) |
| ESI | electro-spray ionization (for MS) |
| h | hour(s) |
| HPLC | high pressure liquid chromatography |
| LC-MS | liquid chromatography coupled with mass spectroscopy |
| min | minute(s) |
| Mp. | melting point |
| MS | mass spectroscopy |
| NMR | nuclear magnetic resonance spectroscopy |
| of th. | of theoretical (yield) |
| RP | reverse phase (for HPLC) |
| $R_t$ | retention time (for HPLC) |
| THF | tetrahydrofuran |

General Methods:

All reactions are carried out under an argon atmosphere unless otherwise noted. Solvents are used as purchased from Aldrich without further purification. "Silica gel" or "Silica" refers to Silica gel 60 (0.040 mm-0.063 mm) from Merck KGaA company. Melting points are obtained with a Buchi 512 or similar melting point device and are uncorrected.

Compounds purified by preparative HPLC are purified over a RP18 column with acetonitrile and water as the eluent, using a 1:9 to 9:1 gradient.

LC-MS/HPLC Methods:

HPLC Method 1

Instrument: HP 1100 with DAD detection; column: Kromasil R$^P$-18, 60 mm×2 mm, 3.5 μm; eluent A: 5 ml HClO$_4$/l water, eluent B: acetonitrile; gradient: 0 min 2% B→0.5 min 2% B→4.5 min 90% B→9 min 90% B; flow: 0.75 ml/min; oven: 30° C.; UV detection: 210 nm.

HPLC Method 2

Instrument: HP 1100 with DAD detection; column: Kromasil R$^P$-18, 60 mm×2 mm, 3.5 μm; eluent A: 5 ml HClO$_4$/l water, eluent B: acetonitrile; gradient: 0 min 2% B→0.5 min 2% B→4.5 min 90% B→6.5 min 90% B; flow: 0.75 ml/min; oven: 30° C.; UV detection: 210 nm.

LC-MS Method 3

Instrument: Micromass Quattro LCZ with HPLC Agilent Series 1100; column: Phenomenex Synergi 2μ Hydro-R$^P$-Mercury 20 mm×4 mm; eluent A: 1 l water+0.5 ml 50% formic acid, eluent B: 1 l acetonitrile+0.5 ml 50% formic acid; gradient: 0.0 min 90% A→2.5 min 30% A→3.0 min 5% A→4.5 min 5% A; flow: 0.0 min 1 nm in/3.0 min/4.5 min 2 ml/min; oven: 50° C.; UV detection: 208-400 nm:

HPLC Method 4

Instrument: HP 1100 with DAD detection; column: Kromasil R$^P$-18, 60 mm×2 mm, 3.5 μm; eluent A: 5 ml HClO$_4$/l water, eluent B: acetonitrile; gradient: 0 min 2% B→0.5 min 2% B→4.5 min 90% B→6.5 min 90% B; flow: 0.75 ml/min; temperature: 30° C.; UV detection: 210 nm.

LC-MS Method 5

Instrument MS: Micromass ZQ; Instrument HPLC: HP 1100 Series; LWV DAD; column: Phenomenex Synergi 2μ Hydro-RP Mercury 20 mm×4 mm; eluent A: 1 l water+0.5 ml 50% formic acid, eluent B: 1 l acetonitrile+0.5 ml 50% formic acid; gradient: 0.0 min 90% A→2.5 min 30% A→3.0 min 5% A→4.5 min 5% A; flow: 0.0 min 1 ml/min→42.5 min/3.0 min/4.5 min 2 ml/min; oven: 50° C.; UV detection: 210 nm.

LC-MS Method 6

Instrument MS: Micromass ZQ; Instrument HPLC: Waters Alliance 2795; column: Phenomenex Synergi 2μ Hydro-RP Mercury 20 mm×4 mm; eluent A: 1 l water+0.5 ml 50% formic acid, eluent B: 1 l acetonitrile+0.5 ml 50% formic acid; gradient: 0.0 min 90% A→2.5 min 30% A→3.0 min 5% A→4.5 min 5% A; flow: 0.0 min 1 ml/min→2.5 min/3.0 min/4.5 min 2 ml/min; oven: 50° C.; UV detection: 210 nm LC-MS Method 7

Instrument: Micromass Platform LCZ with HPLC Agilent Series 1100; column: Phenomenex Synergi 2μ Hydro-RP Mercury 20 mm×4 mm; eluent A: 1 l water+0.5 ml 50% formic acid, eluent B: 1 l acetonitrile+0.5 ml 50% formic acid; gradient: 0.0 min 90% A→2.5 min 30% A→3.0 min 5% A→4.5 min 5% A; flow: 0.0 min 1 ml/min→2.5 min/3.0 min/4.5 min 2 ml/min; oven: 50 C; UV detection: 210 nm Starting Materials and Intermediates Example 1A 5-Methyl-2-pyridinecarbonitrile

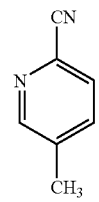

36 g (209 mmol) 2-bromo-5-methylpyridine and 37.5 g (418 mmol) copper cyanide are refluxed for two hours in 500 ml dimethylformamide. After cooling down to 50° C., 10% aqueous ammonia solution (500 ml) is added with stirring. The product is extracted with dichloromethane, the organic phase is dried over magnesium sulfate, and the solvent is removed in vacuo The product is purified by column chromatography (silica, eluent: cyclohexane/ethyl acetate 9:1).

Yield: 18 g (73% of th.)

$^1$H-NMR (300 MHz, CDCl$_3$): Δ=2.4 (s, 3H), 7.6 (m, 2H), 8.6 (s, 1H) ppm.

Example 2A 5-(Hydroxymethyl)-2-pyridinecarbonitrile

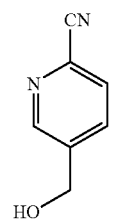

The compound of Example 1A (13 g, 110 mmol) is dissolved in 400 ml tetrachloromethane, and 29.4 g (165 mmol) N-bromosuccinimide and 0.4 g (1.6 mmol) dibenzoylperoxide are added. The reaction mixture is refluxed for three hours, cooled down to room temperature and filtered. The solution is washed with aqueous sodium thiosulfate, dried over magnesium sulfate, and the solvent is removed in vacuo. The residue is dissolved in 200 ml dioxane and 200 ml water, calcium carbonate (44 g, 440 mmol) is added, and the mixture is stirred at reflux for 2 hours. After cooling down to room temperature, the mixture is filtered, and dichloromethane is added. After phase separation, the organic phase is dried over magnesium sulfate, and the solvent is removed in vacuo. The product is purified by chromatography (silica, eluent: cyclohexane/ethyl acetate 2:1).

Yield: 5.2 g (35% of th.)

$^1$H-NMR (300 MHz, DMSO-d$_6$): Δ=4.7 (d, 2H), 5.6 (t, 1H), 8.0 (m, 2H), 8.7 (s, 1H) ppm.

Example 3A

5-Formyl-2-pyridinecarbonitrile

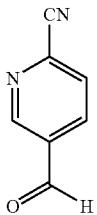

1.04 g (8.2 mmol) oxalylchloride are dissolved in 8 ml dichloromethane. At −78° C., 1.28 g (16.4 mmol) dimethyl-sulfoxide are added dropwise. The solution is stirred at −78° C. for 20 minutes, then 1 g (7.46 mmol) of the compound of Example 2A, dissolved in 7 ml dichloromethane, is added, and stirring at −78° C. is continued for another 2 hours. 3.4 g (33.6 mmol) triethylamine are then added dropwise, and after warming up to room temperature, the mixture is purified by column chromatography (silica, eluent: cyclohexane to cyclohexane/ethyl acetate 2:1).

Yield: 0.76 g (77% of th.)
Mp.: 80-82° C.
HPLC (method 4): $R_t$=2.13 min
MS (ESIpos): m/z=133 (M+H)$^+$
$^1$H-NMR (400 MHz, DMSO-d$_6$): Δ=10.18 (s, 1H), 9.21 (m, 1H), 8.49 (m, 1H), 8.27 (m, 1H) ppm.

Example 4A

Ethyl 4-(4-cyanophenyl)-6-methyl-2-oxo-1-[3-(trifluoromethyl)phenyl]-1,2,3-,4-tetrahydro-5-pyrimidinecarboxylate

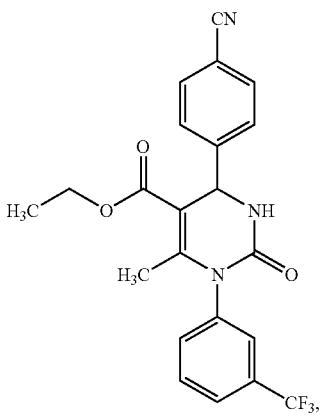

7.0 g (34.29 mmol) N-[3-(trifluoromethyl)phenyl]urea, 8.99 g (68.58 mmol) 4-cyanobenzaldehyde, 8.92 g (68.58 mmol) ethyl 3-oxobutanoate and 20 g polyphosphoric acid ethyl ester are suspended in 250 ml of tetrahydrofuran. The mixture is stirred at reflux for 18 hours. After cooling down to room temperature, the solvent is removed in vacuo and the residue is purified by column chromatography on silica with cyclohexane/ethyl acetate as eluent.

Yield: 13.4 g (91% of th.)
$^1$H-NMR (200 MHz, DMSO-d$_6$): Δ=1.1 (t, 3H), 2.0 (s, 3H), 4.0 (q, 2H), 5.4 (d, 1H), 7.6 (m, 3H), 7.7 (m, 3H), 7.9 (m, 2H), 8.4 (d, 1H) ppm.

Example 5A

Allyl 4-(4-cyanophenyl)-6-methyl-2-oxo-1-[3-(trifluoromethyl)phenyl]-1,2,3-,4-tetrahydro-pyrimidine-5-carboxylate

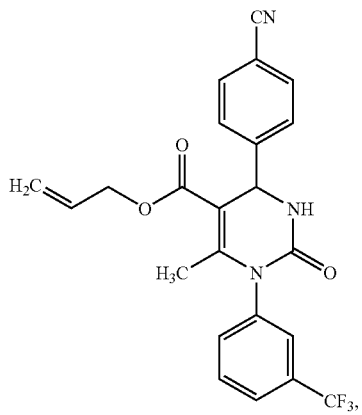

45.0 g ethyl polyphosphate are dissolved in 150 ml dioxane, 15.0 g (73.5 mmol) N-[3-(trifluoro-methyl)phenyl]urea, 19.3 g (147 mmol) 4-cyanobenzaldehyde and 20.9 g (147 mmol) allyl acetoacetate are added, and the mixture is stirred under reflux overnight. Volatiles are evaporated in vacuo, the remainder is dissolved in ethyl acetate and sequentially washed with saturated sodium hydrogencarbonate, sodium hydrogensulfite and sodium chloride solution. The organic phase is dried over magnesium sulfate, filtered and evaporated to dryness in vacuo. The crude product is purified by column chromatography over silica gel (eluent: cyclohexane/ethyl acetate).

Yield: 18.4 g (50% of th.)
$^1$H-NMR (400 MHz, DMSO-d$_6$): Δ=2.08 (s, 3H), 4.55 (d, 2H), 5.05-5.18 (m, 2H), 5.41 (d, 1H), 5.82 (dddd, 1H), 7.54-7.92 (m, 8H), 8.41 (d, 1H) ppm.

Example 6A

Allyl(4R)-4-(4-cyanophenyl)-6-methyl-2-oxo-1-[3-(trifluoromethyl)phenyl]-1-,2,3,4-tetrahydro-pyrimidine-5-carboxylate

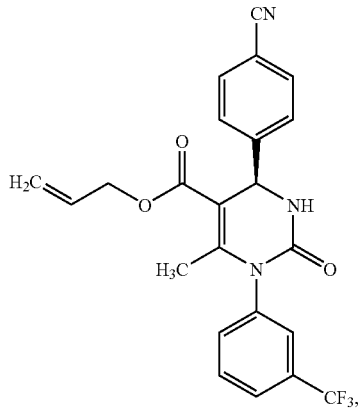

The enantiomers of Example 5A are separated by preparative HPLC on a chiral phase [chiral silica selector based on monomer N-methacryloyl-L-leucine-1-menthylamide, cf. EP-A-379 917; 250 mm×20 mm; eluent: ethyl acetate→methanol→ethyl acetate; flow 50 ml/min; temperature 24° C.; detection 280 nm].

¹H-NMR (400 MHz, DMSO-d₆): Δ=2.08 (s, 3H), 4.55 (d, 2H), 5.05-5.18 (m, 2H), 5.41 (d, 1H), 5.82 (dddd, 1H), 7.54-7.92 (m, 8H), 8.41 (d, 1H) ppm.

[α]²⁰=+25.9° (λ=589 nm, methanol, c=540 mg/100 ml).

Example 7A

4-{5-Acetyl-6-methyl-2-oxo-1-[3-(trifluoromethyl)phenyl]-1,2,3,4-tetrahydro-o-4-pyrimidinyl}-benzonitrile

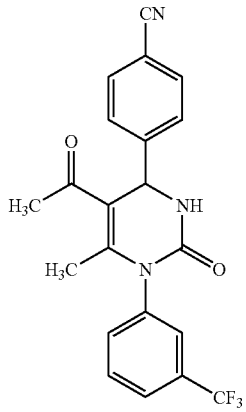 [SMILES: CC(=O)C1=C(C)N(c2cccc(C(F)(F)F)c2)C(=O)NC1c1ccc(C#N)cc1]

30 g (147 mmol) N-[3-(trifluoromethyl)phenyl]urea, 19.3 g (147 mmol) 4-cyanobenzaldehyde and 14.7 g (147 mmol) 2,4-pentanedione are suspended in 300 ml of tetrahydrofuran, and 90 g poly-phosphoric acid ethyl ester are added. The mixture is stirred at reflux for 4 hours. After cooling down to room temperature, the solvent is removed in vacuo, the remainder is dissolved in ethyl acetate and sequentially washed with saturated sodium hydrogencarbonate and sodium chloride solution. The organic phase is dried over magnesium sulfate, filtered and evaporated to dryness in vacuo. The crude product is purified by column chromatography over silica gel (eluent: cyclo-hexane/ethyl acetate).

Yield: 16.8 g (29% of th.)

¹H-NMR (200 MHz, DMSO-d₆): Δ=2.0 (s, 3H), 2.2 (s, 3H), 5.5 (d, 1H), 7.5 (m, 1H), 7.6 (m, 3H), 7.7 (m, 1H), 7.8 (m, 1H), 7.9 (m, 2H), 8.5 (d, 1H) ppm.

Example 8A (4R)-4-{5-Acetyl-6-methyl-2-oxo-1-[3-(trifluoromethyl)phenyl]-1,2,3,4-tetrahydro-4-pyrimidinyl}-benzonitrile

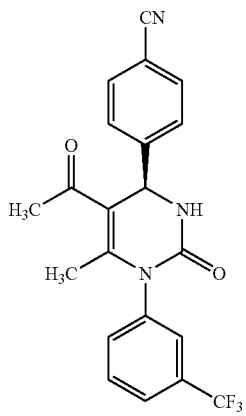 [SMILES: CC(=O)C1=C(C)N(c2cccc(C(F)(F)F)c2)C(=O)N[C@@H]1c1ccc(C#N)cc1]

The enantiomers of Example 7A are separated by preparative HPLC on a chiral phase [chiral silica gel selector based on monomer N-methacryloyl-L-leucine-1-menthylamide, cf. EP-A-379 917; 250 mm×20 mm; eluent: ethyl acetate→methanol→ethyl acetate; flow 25 ml/min; temperature 23° C.; detection 254 nm].

¹H-NMR (200 MHz, DMSO-d₆): Δ=2.0 (s, 3H), 2.2 (s, 3H), 5.5 (d, 1H), 7.5 (m, 1H), 7.6 (m, 3H), 7.7 (m, 1H), 7.8 (m, 1H), 7.9 (m, 2H), 8.5 (d, 1H) ppm.

[α]²⁰=+45.9° (2=589 nm, methanol, c=530 mg/100 ml).

Example 9A 4-(4-Cyanophenyl)-6-methyl-2-oxo-1-[3-(trifluoromethyl)phenyl]-1,2,3,4-tetrahydro-5-pyrimidinecarboxylic acid

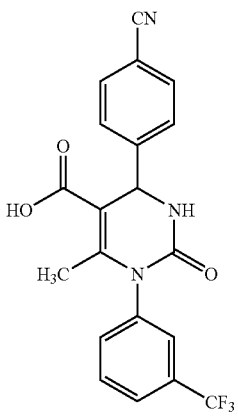

Method A:

3 g (7 mmol) of Example 4A are dissolved in a mixture of 50 ml water and 100 ml 5% potassium hydroxide in ethanol. The reaction mixture is stirred at room temperature for 18 hours. The solvent is removed in vacuo, and the residue is purified by column chromatography on silica with dichloromethane/methanol as eluent.

Yield: 1.27 g (45% of th.)

¹H-NMR (300 MHz, DMSO-d₆): Δ=2.0 (s, 3H), 5.4 (d, 1H), 7.6 (m, 1H), 7.6 (m, 2H), 7.7 (m, 2H), 7.8 (m, 1H), 7.9 (m, 2H), 8.3 (d, 1H), 12.5 (s, 1H) ppm.

Method B:

3.00 g (6.80 mmol) of Example 5A and 888 mg (10.2 mmol) morpholine are dissolved under argon in 30 ml tetrahydrofuran at room temperature. 392 mg (0.34 mmol) tetrakis(triphenylphosphine)-palladium(0) are added, and the mixture is reacted for 15 min at room temperature. The solvent is evaporated in vacuo, the remainder is dissolved in ethyl acetate and washed sequentially with 2 N hydrochloric acid, water and saturated sodium chloride solution. The organic phase is dried over magnesium sulfate and evaporated to dryness. The crude product is purified by preparative RP-HPLC with a water/acetonitrile gradient.

Yield: 1.51 g (52% of th.)

¹H-NMR: see above.

Example 10A (4R)-4-(4-Cyanophenyl)-6-methyl-2-oxo-1-[3-(trifluoromethyl)phenyl]-1,2,3,-4-tetrahydro-5-pyrimidinecarboxylic acid

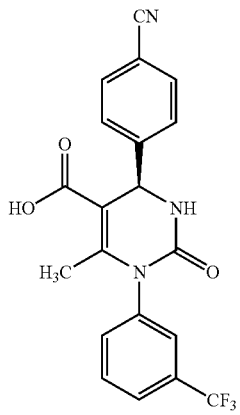 [SMILES: CC1=C(C(=O)O)[C@@H](c2ccc(C#N)cc2)NC(=O)N1c1cccc(C(F)(F)F)c1]

In analogy to Example 9A (method B), this compound is prepared from Example 6A.

Yield: 87% of th.

Example 11A 4-(4-Cyanophenyl)-6-methyl-2-oxo-1-[3-(trifluoromethyl)phenyl]-1,2,3,4-tetrahydro-5-pyrimidine-carboxamide

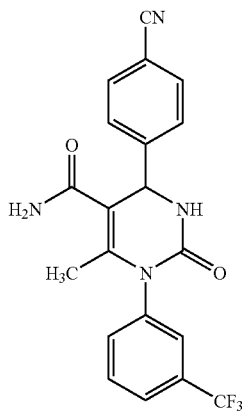

200 mg (0.5 mmol) of Example 9A are dissolved in 5 ml tetrahydrofuran, and 6 mg (0.05 mmol) 4-N,N-dimethylaminopyridine, 77 mg (0.6 mmol) N,N-diisopropylethylamine and 115 mg (0.6 mmol) benzotriazol-1-yloxy-tris(pyrrolidino)phosphonium hexafluorophosphate are added. The reaction mixture is stirred at room temperature for 15 minutes, then 5 ml (2.5 mmol) ammonia (as 0.5 M solution in dioxane) are added. The reaction mixture is stirred at room temperature for 1 hour, then water and ethyl acetate are added. The organic phase is dried over sodium sulfate and evaporated to dryness in vacuo. The crude product is further purified by preparative HPLC.

Yield: 55 mg (28% of th.)

$^1$H-NMR (200 MHz, DMSO-$d_6$): $\Delta$=1.8 (s, 3H), 5.4 (d, 1H), 7.2 (br. s, 1H), 7.4 (br. s, 1H), 7.6 (m, 5H), 7.7 (m, 1H), 7.9 (m, 2H), 8.1 (d, 1H) ppm.

Example 12A

5-{5-Acetyl-6-methyl-2-oxo-1-[3-(trifluoromethyl)phenyl]-1,2,3,4-tetrahydro-o-4-pyrimidinyl}-2-pyridinecarbonitrile

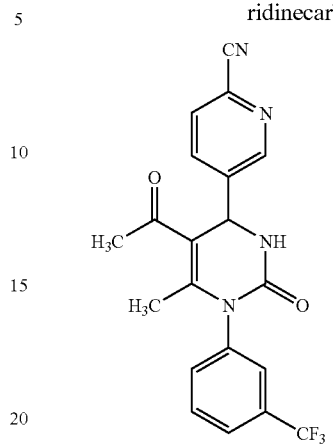

To a stirred solution of Example 3A (75 mg, 0.57 mmol) in tetrahydrofuran (5 ml) is given 2,4-pentandione (57 mg, 0.57 mmol), N-[3-(trifluoromethyl)phenyl]urea (116 mg, 0.57 mmol) and polyphosphoric acid ethyl ester (200 mg) [freshly prepared according to the procedure of Cava et al., J. Org. Chem. 34, 2665 (1969)]. The reaction mixture is refluxed for 24 hours after which time the solution is diluted with DMSO (2 ml) and purified by preparative HPLC.

Yield: 101 mg (44% of th.)

$^1$H-NMR (200 MHz, DMSO-$d_6$): $\Delta$=2.02 (s, 3H), 2.24 (s, 3H), 5.54 (d, 1H), 7.52-7.90 (m, 4H), 8.08 (d, 2H), 8.50 (d, 1H), 8.81 (s, 1H) ppm.

Example 13A (4R)-5-{5-Acetyl-6-methyl-2-oxo-1-[3-(trifluoromethyl)phenyl]-1,2,3,4-tetrahydro-4-pyrimidinyl}-2-pyridinecarbonitrile

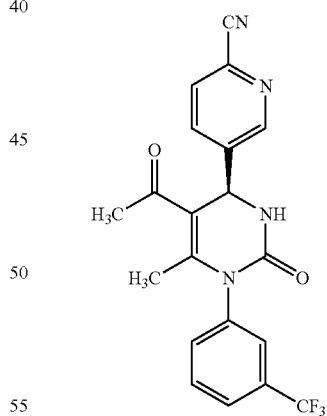

The enantiomers of Example 12A are separated by preparative HPLC on a chiral phase [chiral silica gel selector based on monomer N-methacryloyl-L-leucine-1-menthylamide, cf. EP-A-379 917; 250 mm×20 mm; eluent: ethyl acetate→methanol→ethyl acetate; flow 25 ml/min; temperature 23° C.; detection 254 nm].

$^1$H-NMR (300 MHz, CDCl$_3$): $\Delta$=2.06 (s, 3H), 2.35 (s, 3H), 5.69 (d, 1H), 6.02 (d, 1H), 7.29-7.50 (m, 2H), 7.57-7.75 (m, 3H), 7.83 (dd, 1H), 8.74 (d, 1H) ppm.

MS (ESIpos): m/z=401 (M+H)$^+$ $[\alpha]^{20}_D$=+25.1° ($\lambda$=589 nm, methanol, c=505 mg/100 ml).

Example 14A 4-(4-Cyanophenyl)-6-methyl-2-oxo-1-[3-(trifluoromethyl)phenyl]-1,2,3,4-tetrahydropyrimidine-5-carbonitrile

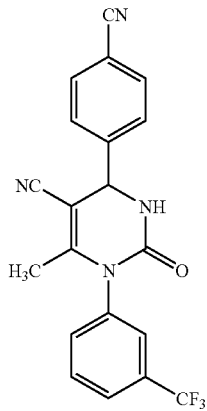

0.609 g (1.52 mmol) of Example 11A are dissolved in 60 ml tetrahydrofuran and 1.24 g (12.93 mmol) (methoxycarbonylsulfamoyl)-triethylammonium-N-betaine are added. The reaction mixture is stirred at room temperature for 1 hour, the solvent is removed in vacuo and the residue is purified by column chromatography on silica with dichloromethane/methanol mixtures as eluent.

Yield: 249 mg (43% of th.)

$^1$H-NMR (300 MHz, DMSO-$d_6$): Δ=1.8 (s, 3H), 5.4 (d, 1H), 7.7 (m, 4H), 7.8 (m, 2H), 8.0 (m, 2H), 8.4 (d, 1H) ppm.

Example 15A (4R)-4-(4-Cyanophenyl)-6-methyl-2-oxo-1-[3-(trifluoromethyl)phenyl]-1,2,3,-4-tetrahydro-pyrimidine-5-carbonitrile

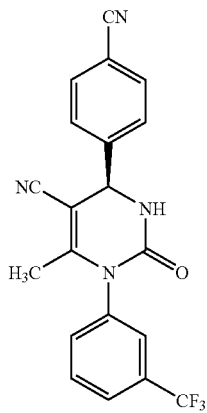

The enantiomers of Example 14A are separated by preparative HPLC on a chiral phase [chiral silica gel selector based on monomer N-methacryloyl-L-leucine-1-menthylamide, cf. EP-A-379 917; 250 mm×20 mm; eluent: ethyl acetate→methanol→ethyl acetate; flow 25 m/min; temperature 23° C.; detection 254 nm].

$^1$H-NMR (300 MHz, DMSO-$d_6$): Δ=1.8 (s, 3H), 5.4 (d, 1H), 7.7 (m, 4H), 7.8 (m, 2H), 8.0 (m, 2H), 8.4 (d, 1H) ppm.

$[α]^2$0=−179° (λ=589 nm, methanol, c=530 mg/100 ml).

Example 16A

Allyl 4-(6-cyanopyridin-3-yl)-6-methyl-2-oxo-1-[3-(trifluoromethyl)phenyl]-1-1,2,3,4-tetrahydro-pyrimidine-5-carboxylate

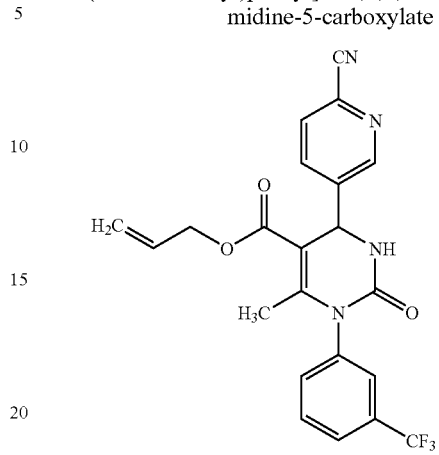

To a stirred solution of Example 3A (29.3 g, 70.4 mmol) in tetrahydrofuran (450 ml) is given allyl 3-oxobutanoate (10.0 g, 70.4 mmol), N-[3-(trifluoromethyl)phenyl]urea (14.4 g, 70.4 mmol) and polyphosphoric acid ethyl ester (33 mg) [freshly prepared according to the procedure of Cava et al., J. Org. Chem. 34, 2665 (1969)]. The reaction mixture is refluxed for 24 hours after which time the solvent is removed in vacuo, and the residue is purified by column chromatography (silica, eluent: cyclohexane/ethyl acetate mixtures).

Yield: 21.1 g (68% of th.)

$^1$H-NMR (300 MHz, DMSO-$d_6$): Δ=2.1 (s, 3H), 4.5 (d, 2H), 5.1 (m, 2H), 5.5 (d, 1H), 5.8 (m, 1H), 7.6 (m, 2H), 7.8 (m, 2H), 8.1 (m, 2H), 8.4 (d, 1H), 8.8 (m, 1H) ppm.

Example 17A 4-(6-Cyanopyridin-3-yl)-6-methyl-2-oxo-1-[3-(trifluoromethyl)phenyl]-1,2,3-,4-tetrahydro-pyrimidine-5-carboxylic acid

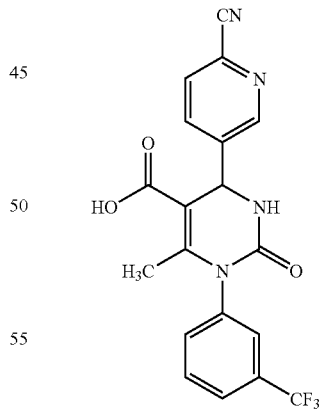

To a stirred solution (under argon) of Example 16A (21.1 g, 47.7 mmol) in tetrahydrofuran (200 ml) is given morpholine (6.2 g, 71.6 mmol) and tetrakis(triphenylphosphino)palladium(0) (0.55 g, 0.48 mmol). The reaction mixture is stirred at room temperature for one hour after which time hydrochloric acid is added (pH 3-4). The solvent is removed in vacuo and the residue is purified by column chromatography (silica, eluent: dichloromethane/methanol mixtures).

Yield: 15.5 g (91% of th.)

$^1$H-NMR (300 MHz, DMSO-d$_6$): Δ=2.1 (s, 3H), 5.4 (d, 1H), 7.6 (m, 1H), 7.7 (m, 1H), 7.8 (m, 2H), 8.1 (m, 2H), 8.3 (d, 1H), 8.8 (m, 1H) ppm.

Example 18A 4-(6-Cyanopyridin-3-yl)-6-methyl-2-oxo-1-[3-(trifluoromethyl)phenyl]-1,2,3-,4-tetrahydro-pyrimidine-5-carboxamide

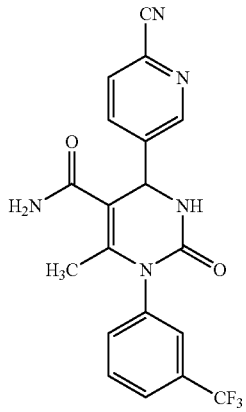

15.5 g (38.5 mmol) of Example 17A are dissolved in 100 ml tetrahydrofuran, and 471 mg (3.85 mmol) 4-N,N-dimethylaminopyridine, 5.98 g (46.2 mmol) N,N-diisopropylethylamine and 8.86 g (46.2 mmol) benzotriazol-1-yloxy-tris(pyrrolidino)phosphonium hexafluorophosphate are added. The reaction mixture is stirred at room temperature for 15 minutes, then 193 ml (96.3 mmol) ammonia (as 0.5 M solution in dioxane) are added. The reaction mixture is stirred at room temperature for 1 hour, then water and ethyl acetate are added. The organic phase is dried over sodium sulfate and evaporated to dryness in vacuo. The crude product is crystallized from dichloromethane/methanol or purified by column chromatography (silica, eluent: dichloromethane/methanol mixtures).

Yield: 7.1 g (46% of th.)

$^1$H-NMR (400 MHz, DMSO-d$_6$): Δ=1.8 (s, 3H), 5.5 (br. s, 1H), 7.1 (br. s, 1H), 7.4 (br. s, 1H), 7.6 (m, 1H), 7.7 (m, 2H), 7.8 (m, 1H), 8.1 (m, 3H), 8.8 (s, 1H) ppm.

Example 19A 4-(6-Cyanopyridin-3-yl)-6-methyl-2-oxo-1-[3-(trifluoromethyl)phenyl]-1,2,3-,4-tetrahydro-pyrimidine-5-carbonitrile

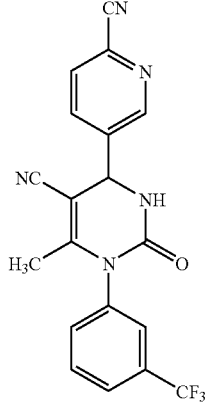

6.51 g (16.2 mmol) of Example 18A are dissolved in 260 ml tetrahydrofuran and 3.12 g (32.44 mmol) (methoxycarbonylsulfamoyl)-triethylammonium-N-betaine are added. The reaction mixture is stirred at room temperature for 2 hours, the solvent is removed in vacuo and the residue is purified by column chromatography on silica with dichloromethane/methanol mixtures as eluent.

Yield: 5.23 g (84% of th.)

$^1$H-NMR (300 MHz, DMSO-d$_6$): Δ=1.8 (s, 3H), 5.5 (s, 1H), 7.7 (m, 2H), 7.8 (m, 1H), 7.9 (m, 1H), 8.2 (m, 1H), 8.3 (m, 1H), 8.4 (m, 1H), 8.9 (m, 1H) ppm.

Example 20A

4-{5-(2-Furoyl)-6-methyl-2-oxo-1-[3-(trifluoromethyl)phenyl]-1,2,3,4-tetra-hydropyrimidin-4-yl}-benzonitrile

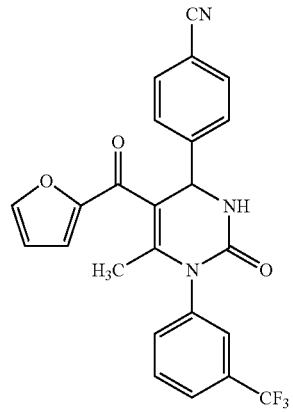 [SMILES: CC1=C(C(=O)c2ccco2)C(c2ccc(C#N)cc2)NC(=O)N1c1cccc(C(F)(F)F)c1]

The title compound is prepared according to the procedure described for Example 4A, with the exception that the title compound is purified by preparative HPLC(RP18 column; eluent: acetonitrile/water 10:90→90:10).

Yield: 287 mg (18.4% of th.)

HPLC (method 1): R$_t$=4.51 min, λ$_{max}$=234 nm

MS (ESIpos): m/z=452 (M+H)$^+$ $^1$H-NMR (300 MHz, DMSO-d$_6$): Δ=8.31 (d, 1H), 7.96 (s, 1H), 7.88-7.53 (m, 8H), 7.37 (d, 1H), 6.71-6.66 (m, 1H), 5.50-5.44 (m, 1H), 1.56 (s, 3H) ppm.

Example 21A

4-{6-Methyl-2-oxo-5-(pyridin-3-ylcarbonyl)-1-[3-(trifluoromethyl)phenyl]-1-,2,3,4-tetrahydro-pyrimidin-4-yl}benzonitrile

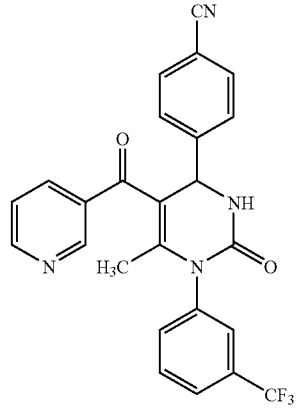 [SMILES: CC1=C(C(=O)c2cccnc2)C(c2ccc(C#N)cc2)NC(=O)N1c1cccc(C(F)(F)F)c1]

The title compound is prepared according to the procedure described for Example 4A, with the exception that the title compound is purified by preparative HPLC(RP18 column; eluent: acetonitrile/0.1% aq. formic acid 10:90-90:10).

Yield: 804 mg (19% of th.)

HPLC (method 1): $R_t$=4.05 min, $\lambda_{max}$=194 nm

MS (ESIpos): m/z=463 (M+H)⁺

¹H-NMR (300 MHz, CDCl₃): Δ=8.79 (m, 1H), 8.73 (m, 1H), 7.92 (m, 1H), 7.70-7.20 (m, 9H), 5.80 (m, 1H), 5.70 (m, 1H), 1.52 (s, 3H) ppm.

Example 22A

Methyl [5-acetyl-6-(4-cyanophenyl)-4-methyl-2-oxo-3-[3-(trifluoromethyl)phenyl]-3,6-dihydropyrimidin-1(2H)-yl]acetate

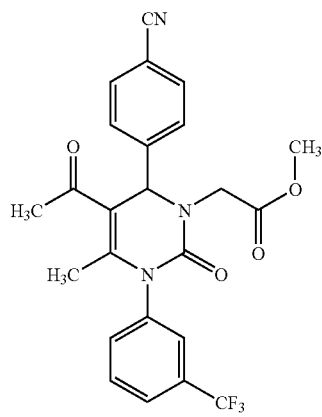 [SMILES: COC(=O)CN1C(=O)N(c2cccc(C(F)(F)F)c2)C(C)=C(C(C)=O)C1c1ccc(C#N)cc1]

2.90 g (7.26 mmol) of Example 7A are dissolved in 30 ml dimethylformamide, 2.01 g (14.5 mmol) potassium carbonate and 1.67 g (10.9 mmol) methyl bromoacetate are added, and the suspension is stirred at 100° C. for 3 hours. The mixture is partitioned between ethyl acetate and water, the combined organic extracts are dried over magnesium sulfate and evaporated in vacuo. The crude product is purified by column chromatography over silica gel (eluent: cyclohexane/ethyl acetate 1:1).

Yield: 2.37 g (69% of th.)

¹H-NMR (300 MHz, DMSO-d₆): Δ=2.00 (s, 3H), 2.22 (s, 3H), 3.55 (s, 3H), 4.01 (d, 1H), 4.23 (d, 1H), 5.73 (s, 1H), 7.56-7.92 (m, 8H) ppm.

Example 23A

Allyl 3-(2-tert.-butoxy-2-oxoethyl)-4-(4-cyanophenyl)-6-methyl-2-oxo-1-[3-(trifluoromethyl)-phenyl]-1,2,3,4-tetrahydropyrimidine-5-carboxylate

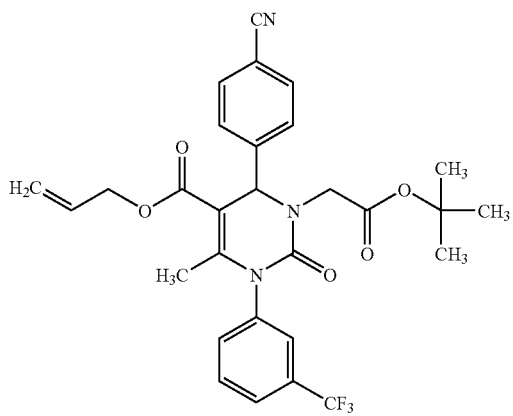 [SMILES: C=CCOC(=O)C1=C(C)N(c2cccc(C(F)(F)F)c2)C(=O)N(CC(=O)OC(C)(C)C)C1c1ccc(C#N)cc1]

1000 mg (2.27 mmol) of Example 5A are dissolved in 10 ml dimethylformamide, 344 mg (2.49 mmol) potassium carbonate and 486 mg (2.49 mmol) tert.-butyl bromoacetate are added, and the suspension is stirred at room temperature overnight. The mixture is partitioned between ethyl acetate and aqueous potassium dihydrogenphosphate/disodium hydrogenphosphate buffer (pH 7), the combined organic extracts are washed with water and aqueous sodium chloride solution, dried over magnesium sulfate, and evaporated in vacuo. The crude product is purified by column chromatography over silica gel (eluent: cyclohexane/ethyl acetate 3:1).

Yield: 985 mg (78% of th.)

¹H-NMR (200 MHz, DMSO-d₆): Δ=1.29 (s, 9H), 2.08 (s, 3H), 3.88 (d, 1H), 4.09 (d, 1H), 4.52 (d, 2H), 5.09-5.15 (m, 2H), 5.60 (s, 1H), 5.71-5.92 (m, 1H), 7.60-7.93 (m, 8H) ppm.

In analogy to the procedure for Example 23A, the following compound is prepared:

| Example No. | Structure | Starting materials | Yield [%] | $R_t$ [min] (method) | Mass [M + H]⁺ |
|---|---|---|---|---|---|
| A. 24A | 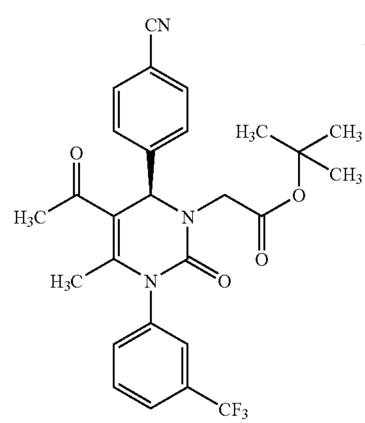 | Example 8A; tert.-butyl bromoacetate | 79 | 5.14 (2) | 514 |

Example 25A

[5-Acetyl-6-(4-cyanophenyl)-4-methyl-2-oxo-3-[3-(trifluoromethyl)phenyl]-3-,6-dihydropyrimidin-1(2H)-yl]acetic acid

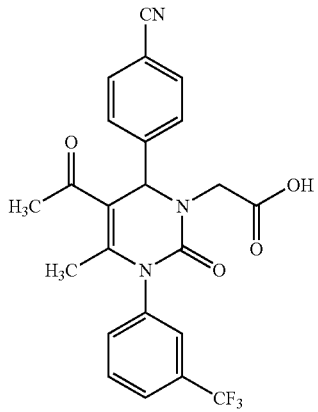 [SMILES: CC(=O)C1=C(C)N(c2cccc(C(F)(F)F)c2)C(=O)N(CC(=O)O)C1c1ccc(C#N)cc1]

2.30 g (4.88 mmol) of Example 22A are dissolved in 20 ml tetrahydrofuran, 3.70 ml (7.32 mmol) lithium hydroxide (2 N solution in water) are added, and the reaction mixture is stirred at room temperature for 2 hours. The mixture is partitioned between ethyl acetate and 2 N hydrochloric acid, the organic phase is dried over magnesium sulfate and evaporated to dryness in vacuo. The crude product is purified by RP-HPLC with a water/acetonitrile gradient.

Yield: 1.66 g (74% of th.)

$^1$H-NMR (400 MHz, DMSO-$d_6$): Δ=2.00 (s, 3H), 2.22 (s, 3H), 3.83 (d, 1H), 4.17 (d, 1H), 5.71 (s, 1H), 7.60 (d, 1H), 7.63-7.76 (m, 4H), 7.82 (d, 1H), 7.87 (d, 2H), 12.70 (br. s, 1H) ppm.

Example 26A

[5-[(Allyloxy)carbonyl]-6-(4-cyanophenyl)-4-methyl-2-oxo-3-[3-(trifluoromethyl)phenyl]-3,6-dihydropyrimidin-1(2H)-yl]acetic acid

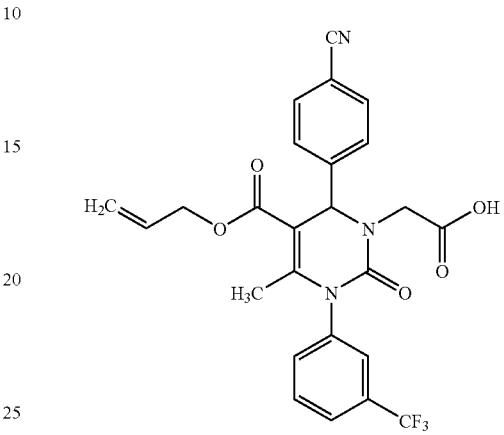

150 mg (0.27 mmol) of Example 23A are dissolved in 2 ml trifluoroacetic acid/dichloromethane (1:1) and stirred at room temperature for 2 h. The reaction mixture is evaporated to dryness in vacuo and the crude product is purified by RP-HPLC with a water/acetonitrile gradient.

Yield: 112 mg (83% of th.)

$^1$H-NMR (300 MHz, DMSO-$d_6$): Δ=2.06 (s, 3H), 3.76 (d, 1H), 4.11 (d, 1H), 4.55 (ddd, 2H), 5.12 (ddt, 1H), 5.17 (ddt, 1H), 5.62 (s, 1H), 5.82 (ddt, 1H), 7.60-7.90 (m, 8H) ppm.

In analogy to the procedure for Example 26A, the following compound is prepared:

| Example No. | Structure | Starting material | Yield [%] | $R_t$ [min] (method) | Mass [M + H]$^+$ |
|---|---|---|---|---|---|
| B. 27A | (structure shown) | Example 24A | 94 | 4.42 (2) | 458 |

Example 28A tert.-Butyl [6-(4-cyanophenyl)-5-(2-furoyl)-4-methyl-2-oxo-3-[3-(trifluoromethyl)phen-yl]-3,6-dihydropyrimidin-1(2H)-yl]acetate

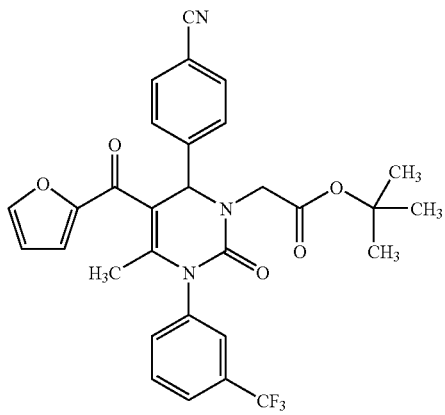 [SMILES: CC1=C(C(=O)c2ccco2)C(c2ccc(C#N)cc2)N(CC(=O)OC(C)(C)C)C(=O)N1c1cccc(C(F)(F)F)c1]

A stirred suspension of 4-{5-(2-furoyl)-6-methyl-2-oxo-1-[3-(trifluoromethyl)phenyl]-1,2,3,4-tetr-a-hydropyrimidin-4-yl}benzonitrile (Example 20A) (150 mg, 0.33 mmol) and potassium carbonate (83 mg, 0.60 mmol) in dimethylformamide (5 ml) is treated with tert.-butyl bromoacetate (71 mg, 0.36 mmol), then stirred at room temperature overnight (16 h). The reaction solution is then diluted with methanol (7 ml) and purified directly by preparative HPLC(RP18 column; eluent: acetonitrile/water 10:90→90:10).

Yield: 138 mg (73% of th.)
HPLC (method 1): $R_t$=5.07 min, $\lambda_{max}$=234 nm
MS (ESIpos): m/z=566 (M+H)$^+$
$^1$H-NMR (300 MHz, CDCl$_3$): Δ=7.76-7.36 (m, 9H), 7.22 (m, 1H), 6.57-6.51 (m, 1H), 5.73 (s, 1H), 4.57 (d, 1H), 3.42 (d, 1H), 1.60 (s, 3H), 1.46 (s, 9H) ppm.

Example 29A

[6-(4-Cyanophenyl)-5-(2-furoyl)-4-methyl-2-oxo-3-[3-(trifluoromethyl)pheny-l]-3,6-dihydropyrimidin-1(2H)-yl]acetic acid

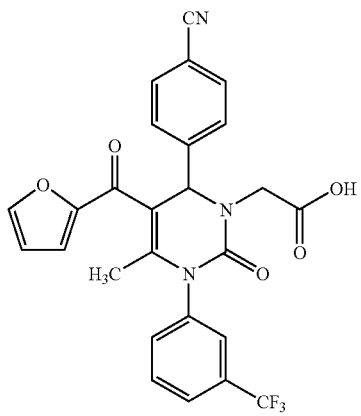 [SMILES: CC1=C(C(=O)c2ccco2)C(c2ccc(C#N)cc2)N(CC(=O)O)C(=O)N1c1cccc(C(F)(F)F)c1]

The title compound is prepared from Example 28A according to the procedure described for Example 26A.
Yield: 35 mg (39% of th.)
LC-MS (method 5): $R_t$=2.37 min
MS (ESIpos): m/z=510 (M+H)$^+$ $^1$H-NMR (300 MHz, DMSO-d$_6$): Δ=12.0 (br. s, 1H), 7.99-7.92 (m, 1H), 7.88-7.58 (m, 7H), 7.51-7.40 (m, 2H), 6.72-6.65 (m, 1H), 5.88 (s, 1H), 4.19 (d, 1H), 2.93 (d, 1H), 1.55 (s, 3H) ppm.

Example 30A tert.-Butyl [6-(4-cyanophenyl)-4-methyl-2-oxo-5-(pyridin-3-ylcarbonyl)-3-[3-(trifluoromethyl)-phenyl]-3,6-dihydropyrimidin-1(2H)-yl]acetate

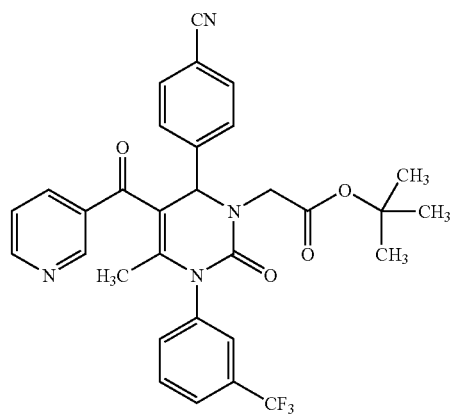 [SMILES: CC1=C(C(=O)c2cccnc2)C(c2ccc(C#N)cc2)N(CC(=O)OC(C)(C)C)C(=O)N1c1cccc(C(F)(F)F)c1]

The title compound is prepared from Example 21A according to the procedure described for Example 28A.
Yield: 111 mg (52.6% of th.)
LC-MS (method 3): $R_t$=2.76 min
MS (ESIpos): m/z=577 (M+H)$^+$
$^1$H-NMR (300 MHz, CDCl$_3$): Δ=8.83 (d, 1H), 8.75 (m, 1H), 8.01 (m, 1H), 7.80-7.30 (m, 9H), 5.66 (s, 1H), 4.63 (d, 1H), 3.42 (d, 1H), 1.51 (s, 3H), 1.47 (s, 9H) ppm.

Example 31A

[6-(4-Cyanophenyl)-4-methyl-2-oxo-5-(pyridin-3-ylcarbonyl)-3-[3-(trifluoro-methyl)phenyl]-3,6-dihydropyrimidin-1(2H)-yl]acetic acid

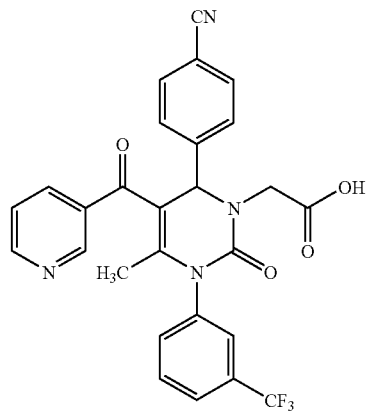 [SMILES: CC1=C(C(=O)c2cccnc2)C(c2ccc(C#N)cc2)N(CC(=O)O)C(=O)N1c1cccc(C(F)(F)F)c1]

The title compound is prepared from Example 30A according to the procedure described for Example 26A.
Yield: 22 mg (33% of th.)
LC-MS (method 5): $R_t$=2.20 min
MS (ESIpos): m/z=521 (M+H)$^+$ $^1$H-NMR (300 MHz, DMSO-d$_6$): Δ=12.7 (br. s, 1H), 8.85 (d, 1H), 8.73 (m, 1H), 8.05 (m, 1H), 7.90-7.63 (m, 8H), 7.54-7.46 (m, 1H), 5.71 (s, 1H), 4.23 (d, 1H), 3.76 (d, 1H), 1.45 (s, 3H) ppm.

Example 32A

2-[(tert.-Butoxycarbonyl)amino]ethyl methanesulfonate

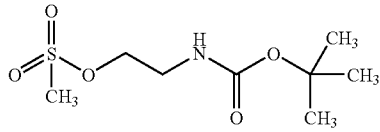

1 g (6.2 mmol) tert.-butyl (2-hydroxyethyl)carbamate and 0.75 g (7.44 mmol) triethylamine are dissolved in 250 ml dichloromethane and the solution is cooled to 0° C. 0.78 g (6.82 mmol) methanesulfonyl chloride are added slowly. The reaction mixture is stirred at 0° C. for one hour, then water is added, and the aqueous phase is extracted three times with ethyl acetate. The combined organic phases are dried over sodium sulfate, evaporated to dryness in vacuo, and the crude product is purified by column chromatography (silica, eluent: cyclohexane/ethyl acetate 5:1→2:1).

Yield: 1.3 g (87% of th.)

$^1$H-NMR (300 MHz, DMSO-d$_6$): Δ=1.4 (s, 9H), 3.2 (m, 2H), 3.3 (s, 3H), 4.2 (t, 2H), 7.1 (br t, 1H) ppm.

Example 33A

4-{5-Isobutyryl-6-methyl-2-oxo-1-[3-(trifluoromethyl)phenyl]-1,2,3,4-tetra-hydropyrimidin-4-yl}-benzonitrile

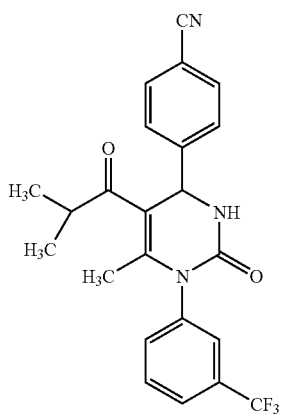 [SMILES: CC1=C(C(=O)C(C)C)C(c2ccc(C#N)cc2)NC(=O)N1c1cccc(C(F)(F)F)c1]

To a stirred solution of N-[3-(trifluoromethyl)phenyl]urea (6.37 g, 31.2 mmol), 4-cyanobenzaldehyde (4.09 g, 31.2 mmol) and 5-methylhexane-2,4-dione (4.0 g, 31.2 mmol) in tetrahydrofuran (150 ml) is added ethyl polyphosphate (12 g). The mixture is stirred at reflux for 18 hours. After cooling down to room temperature, the solvent is removed in vacuo and the residue is purified by column chromatography on silica with cyclohexane/ethyl acetate as eluent.

Yield: 1.91 g (14% of th.)

$^1$H-NMR (300 MHz, DMSO-d$_6$): Δ=8.37 (d, 1H), 7.92-7.52 (m, 8H), 5.47 (m, 1H), 2.95 (m, 1H), 1.86 (s, 3H), 0.95 (d, 3H), 0.81 (d, 3H) ppm.

Example 34A tert.-Butyl [6-(4-cyanophenyl)-5-isobutyryl-4-methyl-2-oxo-3-[3-(trifluoromethyl)phen-yl]-3,6-dihydropyrimidin-1(2H)-yl]acetate

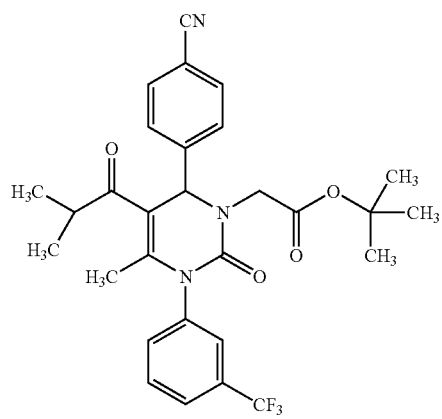 [SMILES: CC1=C(C(=O)C(C)C)C(c2ccc(C#N)cc2)N(CC(=O)OC(C)(C)C)C(=O)N1c1cccc(C(F)(F)F)c1]

The title compound is prepared from Example 33A according to the procedure described for Example 22A, with the exception that the reaction time is 16 hours (overnight) at room temperature (22° C.).

Yield: 44 mg (79% of th.)

$^1$H-NMR (300 MHz, DMSO-d$_6$): Δ=7.98-7.46 (m, 8H), 5.68 (s, 1H), 4.17-3.87 (m, 2H), 2.99 (m, 1H), 1.85 (s, 3H), 1.31 (s, 9H), 1.58-0.77 (m, 6H) ppm

Example 35A

[6-(4-Cyanophenyl)-5-isobutyryl-4-methyl-2-oxo-3-[3-(trifluoromethyl)pheny-l]-3,6-dihydropyrimidin-1(2H)-yl]acetic acid

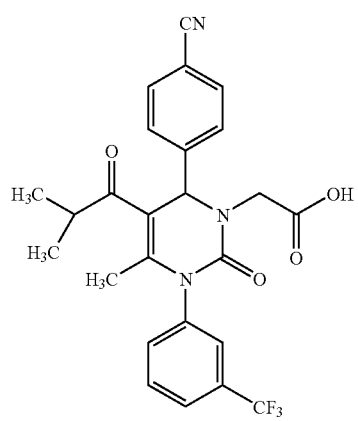 [SMILES: CC1=C(C(=O)C(C)C)C(c2ccc(C#N)cc2)N(CC(=O)O)C(=O)N1c1cccc(C(F)(F)F)c1]

The title compound is prepared from Example 34A according to the procedure described for Example 26A.

Yield: 500 mg (91% of th.)

¹H-NMR (300 MHz, DMSO-d₆): Δ=12.68 (s, 1H), 7.96-7.48 (m, 8H), 5.71 (s, 1H), 4.27-3.73 (m, 2H), 3.02 (m, 1H), 1.84 (s, 3H), 0.95 (d, 3H), 0.84 (d, 3H) ppm.

PREPARATION EXAMPLES

Example 1

Methyl 3-{[5-acetyl-6-(4-cyanophenyl)-4-methyl-2-oxo-3-[3-(trifluoromethyl-)phenyl]-3,6-dihydropyrimidin-1(2H)-yl]methyl}benzoate

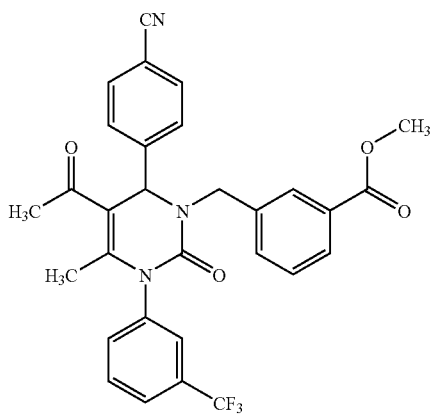 [SMILES: COC(=O)c1cccc(CN2C(=O)N(c3cccc(C(F)(F)F)c3)C(C)=C(C(C)=O)C2c2ccc(C#N)cc2)c1]

150 mg (0.38 mmol) of Example 7A are dissolved in 3 ml tetrahydrofuran, and 38 mg (0.94 mmol) sodium hydride (as 60% dispersion in mineral oil) are added. After stirring at room temperature for one hour, 129 mg (0.56 mmol) methyl 3-(bromomethyl)benzoate are added. After stirring at room temperature for 16 hours, the mixture is quenched with methanol, the solvent is removed in vacuo and the residue is purified by column chromatography on silica with cyclohexane/ethyl acetate mixtures as eluent.

Yield: 106 mg (52% of th.)
LC-MS (method 6): R$_t$=2.59 min
MS (ESIpos): m/z=548 (M+H)⁺.

Example 2 tert.-Butyl (6R)-3-{[5-acetyl-6-(4-cyanophenyl)-4-methyl-2-oxo-3-[3-(trifluoromethyl)-phenyl]-3,6-dihydropyrimidin-1(2H)-yl]methyl}benzoate

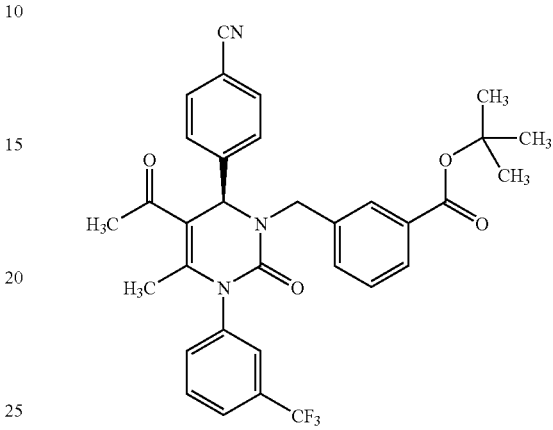

400 mg (1.0 mmol) of Example 8A are dissolved in 5 ml dimethylformamide, and 407 mg (1.5 mmol) tert.-butyl 3-(bromomethyl)benzoate and 277 mg (2.0 mmol) potassium carbonate are added. The mixture is stirred at 100° C. for 4 hours, then water is added and the aqueous solution is extracted three times with ethyl acetate. The combined organic phases are dried over sodium sulfate, the solvent is removed in vacuo and the residue is purified by column chromatography on silica with cyclohexane/ethyl acetate mixtures as eluent.

Yield: 181 mg (31% of th.)
LC-MS (method 6): R$_t$=2.92 min
MS (ESIpos): m/z=590 (M+H)⁺.

In analogy to the procedure for Example 1, the following compounds are prepared:

| Example No. | Structure | Starting materials | Yield [%] | R$_t$ [min] (method) | Mass [M + H]⁺ |
|---|---|---|---|---|---|
| 3 | (structure shown) | Example 7A; tert.-butyl [4-(bromomethyl)-phenyl](cyclopentyl)acetate | 20 | 3.23 (6) | 616 |

-continued

| Example No. | Structure | Starting materials | Yield [%] | $R_t$ [min] (method) | Mass $[M + H]^+$ |
|---|---|---|---|---|---|
| 4 | (structure) | Example 7A; methyl 4-[(bromoacetyl)-(methyl)-amino]benzoate | 40 | 2.60 (5) | 605 |
| 5 | (structure) | Example 7A; methyl 4-[(bromoacetyl)-amino]benzoate | 30 | 2.63 (3) | 591 |

In analogy to the procedure for Example 2, the following compounds are prepared:

| Example No. | Structure | Starting materials | Yield [%] | $R_t$ [min] (method) | Mass $[M + H]^+$ |
|---|---|---|---|---|---|
| 6 | (structure) | Example 7A; tert.-butyl 4-(bromomethyl)-benzoate | 47 | 3.13 (7) | 590 |

-continued

| Example No. | Structure | Starting materials | Yield [%] | R$_t$ [min] (method) | Mass [M + H]$^+$ |
|---|---|---|---|---|---|
| 7 | (structure) | Example 8A; tert.-butyl 4-(bromomethyl)-benzoate | 68 | 2.94 (6) | 590 |
| 8 | (structure) | Example 7A; methyl 2-(chloromethyl)-1,3-oxazole-4-carboxylate | 25 | 2.27 (6) | 539 |
| 9 | (structure) | Example 8A; methyl 2-(chloromethyl)-1,3-oxazole-4-carboxylate | 30 | 2.43 (5) | 539 |

-continued

| Example No. | Structure | Starting materials | Yield [%] | $R_t$ [min] (method) | Mass $[M + H]^+$ |
|---|---|---|---|---|---|
| 10 | 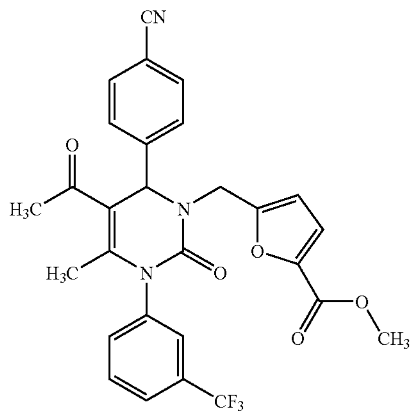 [SMILES: COC(=O)c1ccc(CN2C(=O)N(c3cccc(C(F)(F)F)c3)C(C)=C(C(C)=O)C2c2ccc(C#N)cc2)o1] | Example 7A; methyl 5-(chloromethyl)-2-furoate | 48 | 2.45 (6) | 538 |
| 11 | 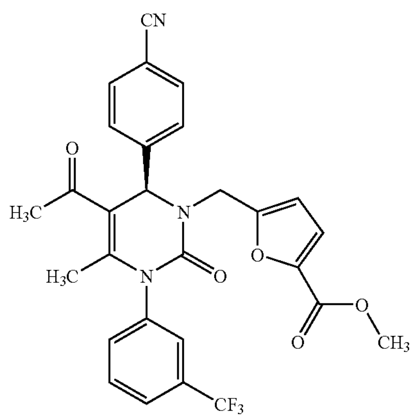 [SMILES: COC(=O)c1ccc(CN2C(=O)N(c3cccc(C(F)(F)F)c3)C(C)=C(C(C)=O)[C@H]2c2ccc(C#N)cc2)o1] | Example 8A; methyl 5-(chloromethyl)-2-furoate | 61 | 2.65 (3) | 538 |
| 12 | 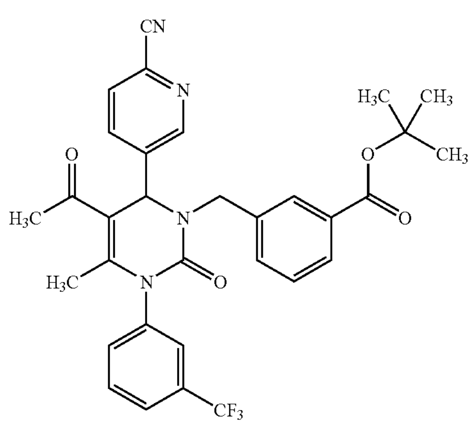 [SMILES: CC(=O)C1=C(C)N(c2cccc(C(F)(F)F)c2)C(=O)N(Cc2cccc(C(=O)OC(C)(C)C)c2)C1c1ccc(C#N)nc1] | Example 12A; tert.-butyl-3-(bromomethyl)-benzoate | 19 | 2.81 (6) | 591 |

-continued
| Example No. | Structure | Starting materials | Yield [%] | $R_t$ [min] (method) | Mass [M + H]$^+$ |
|---|---|---|---|---|---|
| 13 | 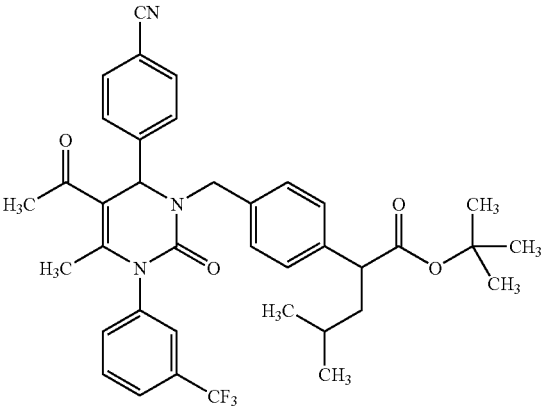 [SMILES: CC(=O)C1=C(C)N(c2cccc(C(F)(F)F)c2)C(=O)N(Cc2ccc(C(CC(C)C)C(=O)OC(C)(C)C)cc2)C1c1ccc(C#N)cc1] | Example 7A; tert.-butyl 2-[4-(bromomethyl)-phenyl]-4-methyl-pentanoate | 25 | 3.35 (5) | 660 |
| 14 | 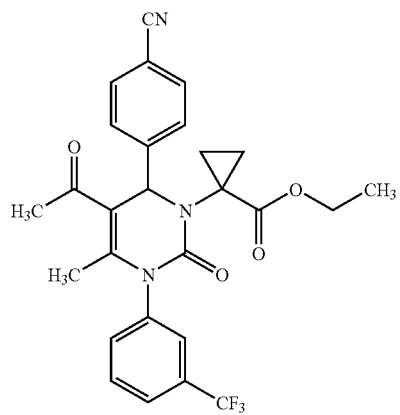 [SMILES: CCOC(=O)C1(N2C(=O)N(c3cccc(C(F)(F)F)c3)C(C)=C(C(C)=O)C2c2ccc(C#N)cc2)CC1] | Example 7A; ethyl 2-bromo-4-chloro-butanoate | 33 | 2.56 (5) | 512 |
| 15 | 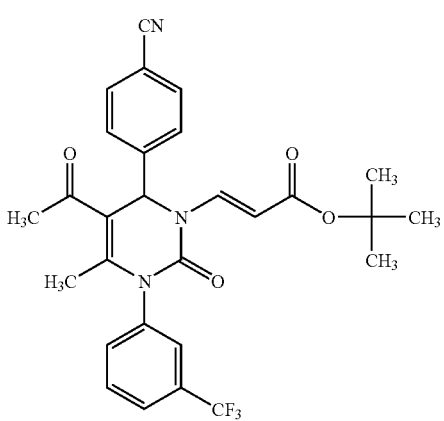 [SMILES: CC(=O)C1=C(C)N(c2cccc(C(F)(F)F)c2)C(=O)N(/C=C/C(=O)OC(C)(C)C)C1c1ccc(C#N)cc1] | Example 7A; tert.-butyl propiolate | 30 | 2.97 (3) | 526 |

| Example No. | Structure | Starting materials | Yield [%] | R$_t$ [min] (method) | Mass [M + H]$^+$ |
|---|---|---|---|---|---|
| 16 | 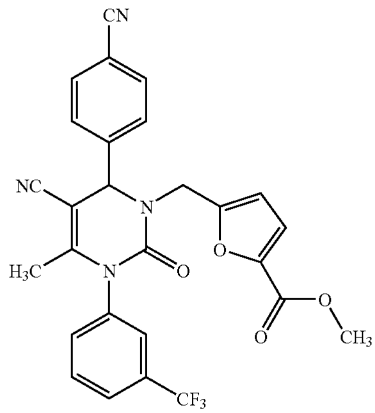 | Example 14A; methyl 5-(chloromethyl)-2-furoate | 44 | 2.61 (5) | 521 |
| 17 | 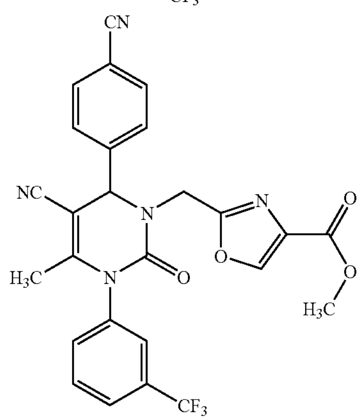 | Example 14A; methyl 2-(chloromethyl)-1,3-oxazole-4-carboxylate | 26 | 2.31 (6) | 522 |

Example 18

4-{[5-Acetyl-6-(4-cyanophenyl)-4-methyl-2-oxo-3-]3-(trifluoromethyl)phenyl-]-3,6-dihydro-pyrimidin-1(2H)-yl]methyl}benzoic acid

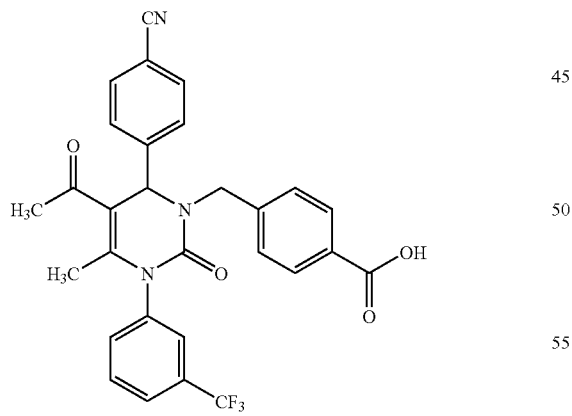

65 mg (0.11 mmol) of Example 6 are dissolved in 5 ml dichloromethane and 0.5 ml trifluoroacetic acid. The solution is stirred at room temperature for one hour, the solvent is removed in vacuo and the residue is purified by column chromatography on silica with dichloromethane/methanol mixtures as eluent.

Yield: 56 mg (94% of th.)

$^1$H-NMR (300 MHz, DMSO-d$_6$): Δ=2.0 (s, 3H), 2.2 (s, 3H), 4.2 (d, 1H), 4.9 (d, 1H), 5.6 (s, 1H), 7.4 (m, 2H), 7.6 (m, 3H), 7.7 (m, 2H), 7.9 (m, 5H), 12.9 (br. s, 1H) ppm.

In analogy to the procedure for Example 18, the following compounds are prepared:

| Example No. | Structure | Starting material | Yield [%] | $R_t$ [min] (method) | Mass $[M + H]^+$ |
|---|---|---|---|---|---|
| 19 | 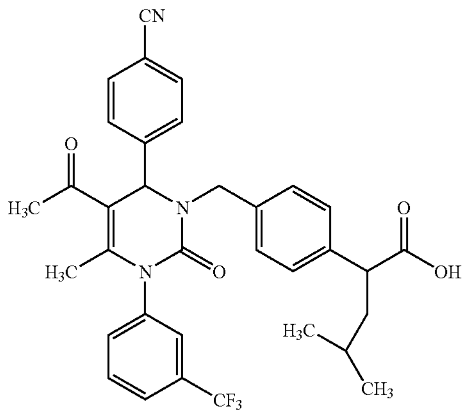 [SMILES: CC(=O)C1=C(C)N(c2cccc(C(F)(F)F)c2)C(=O)N(Cc2ccc(C(CC(C)C)C(=O)O)cc2)C1c1ccc(C#N)cc1] | Example 13 | 30 | 2.66 (6) | 604 |
| 20 | 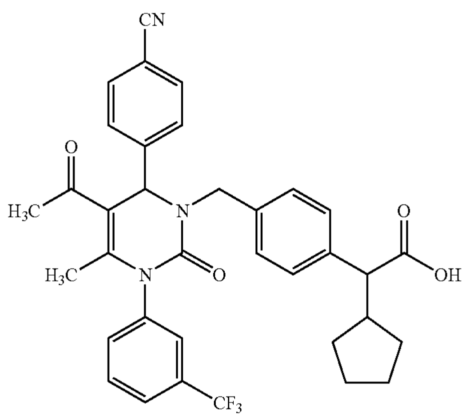 [SMILES: CC(=O)C1=C(C)N(c2cccc(C(F)(F)F)c2)C(=O)N(Cc2ccc(C(C(=O)O)C3CCCC3)cc2)C1c1ccc(C#N)cc1] | Example 3 | 7 | 2.69 (6) | 616 |
| 21 | 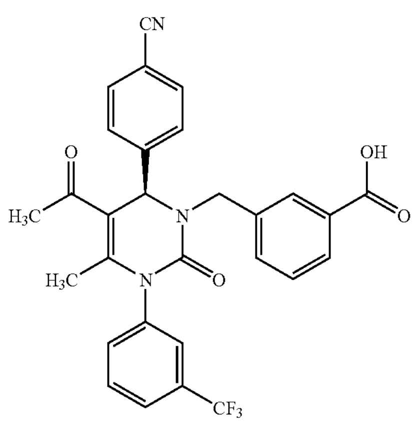 [SMILES: CC(=O)C1=C(C)N(c2cccc(C(F)(F)F)c2)C(=O)N(Cc2cccc(C(=O)O)c2)[C@@H]1c1ccc(C#N)cc1] | Example 2 | 49 | 2.45 (5) | 534 |

-continued

| Example No. | Structure | Starting material | Yield [%] | R_t [min] (method) | Mass [M + H]+ |
| --- | --- | --- | --- | --- | --- |
| 22 | 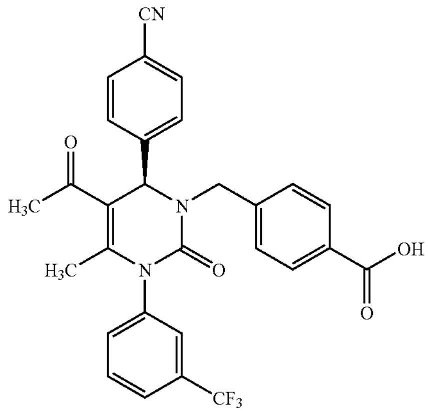 [SMILES: CC(=O)C1=C(C)N(c2cccc(C(F)(F)F)c2)C(=O)N(Cc2ccc(C(=O)O)cc2)[C@@H]1c1ccc(C#N)cc1] | Example 7 | 33 | 2.45 (5) | 534 |
| 23 | 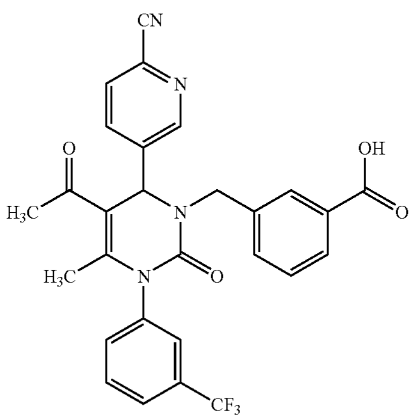 [SMILES: CC(=O)C1=C(C)N(c2cccc(C(F)(F)F)c2)C(=O)N(Cc2cccc(C(=O)O)c2)C1c1ccc(C#N)nc1] | Example 12 | 37 | 2.36 (5) | 535 |
| 24 | 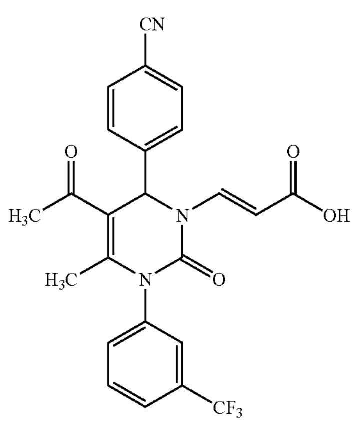 [SMILES: CC(=O)C1=C(C)N(c2cccc(C(F)(F)F)c2)C(=O)N(/C=C/C(=O)O)C1c1ccc(C#N)cc1] | Example 15 | 89 | 2.14 (6) | 470 |

Example 25

5-{[5-Acetyl-6-(4-cyanophenyl)-4-methyl-2-oxo-3-[3-(trifluoromethyl)phenyl-]-3,6-dihydropyrimidin-1(2H)-yl]methyl}-2-furanoic acid

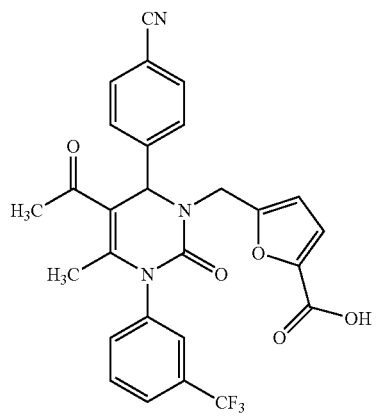 [SMILES: CC(=O)C1=C(C)N(c2cccc(C(F)(F)F)c2)C(=O)N(Cc2ccc(C(=O)O)o2)C1c1ccc(C#N)cc1]

60 mg (0.11 mmol) of Example 10 are dissolved in 5 ml tetrahydrofuran, and 4 mg (0.17 mmol) lithium hydroxide, dissolved in 2.5 ml water, are added. After five hours stirring at room temperature, another 4 mg (0.17 mmol) lithium hydroxide in 2.5 ml water are added and stirring is continued for two hours. The pH is adjusted to <7 with hydrochloric acid, the solvent is removed in vacuo and the residue is purified by preparative HPLC.

Yield: 45 mg (77% of th.)

$^1$H-NMR (300 MHz, DMSO-$d_6$): Δ=1.9 (s, 3H), 2.3 (s, 3H), 4.4 (d, 1H), 4.8 (d, 1H), 5.7 (s, 1H), 6.4 (d, 1H), 7.1 (d, 1H), 7.6 (m, 3H), 7.7 (m, 2H), 7.8 (m, 3H), 13.0 (br. s, 1H) ppm.

In analogy to the procedure for Example 25, the following compounds are prepared:

| Example No. | Structure | Starting material | Yield [%] | $R_t$ [min] (method) | Mass $[M + H]^+$ |
|---|---|---|---|---|---|
| 26 | 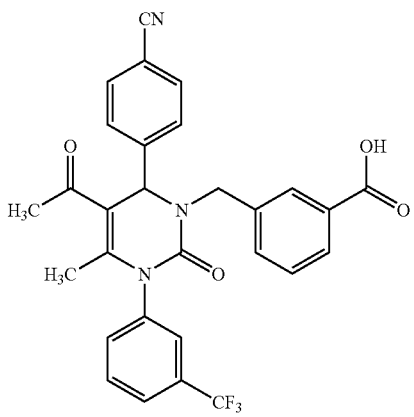 | Example 1 | 9 | 2.30 (6) | 534 |
| 27 | 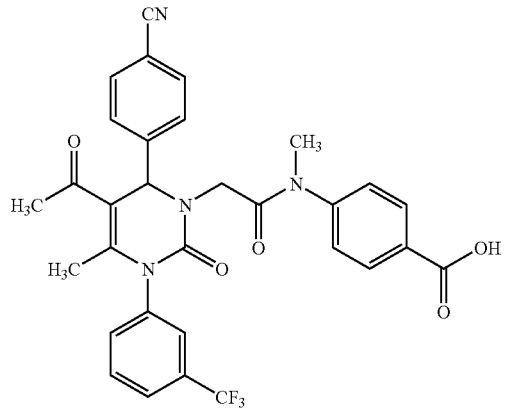 [SMILES: CC(=O)C1=C(C)N(c2cccc(C(F)(F)F)c2)C(=O)N(CC(=O)N(C)c2ccc(C(=O)O)cc2)C1c1ccc(C#N)cc1] | Example 4 | 41 | 2.27 (5) | 591 |

-continued

| Example No. | Structure | Starting material | Yield [%] | R$_t$ [min] (method) | Mass [M + H]$^+$ |
|---|---|---|---|---|---|
| 28 | 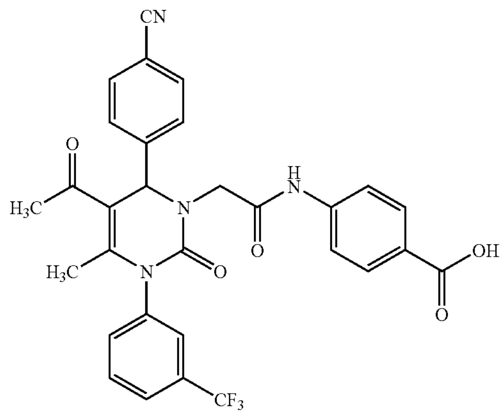 [SMILES: CC(=O)C1=C(C)N(c2cccc(C(F)(F)F)c2)C(=O)N(CC(=O)Nc2ccc(C(=O)O)cc2)C1c1ccc(C#N)cc1] | Example 5 | 53 | 2.38 (3) | 577 |
| 29 | 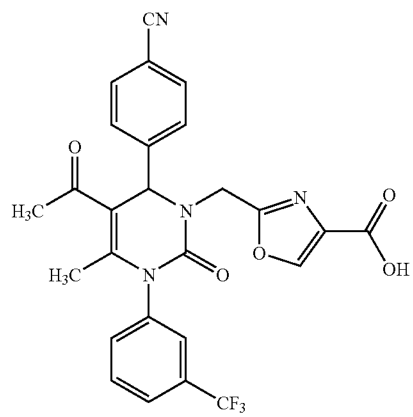 [SMILES: CC(=O)C1=C(C)N(c2cccc(C(F)(F)F)c2)C(=O)N(Cc2nc(C(=O)O)co2)C1c1ccc(C#N)cc1] | Example 8 | 75 | 2.24 (3) | 525 |
| 30 | 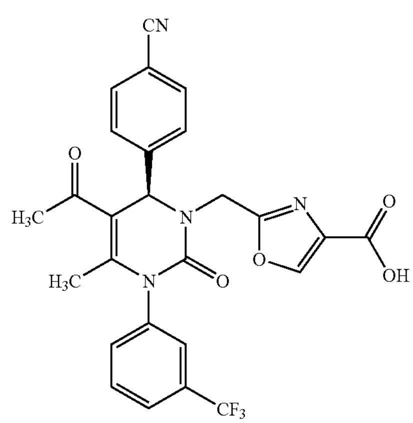 [SMILES: CC(=O)C1=C(C)N(c2cccc(C(F)(F)F)c2)C(=O)N(Cc2nc(C(=O)O)co2)[C@@H]1c1ccc(C#N)cc1] | Example 9 | 78 | 2.25 (5) | 525 |

-continued

| Example No. | Structure | Starting material | Yield [%] | $R_t$ [min] (method) | Mass $[M + H]^+$ |
|---|---|---|---|---|---|
| 31 | (structure) | Example 11 | 91 | 2.37 (3) | 524 |
| 32 | (structure) | Example 14 | 29 | 2.10 (6) | 484 |
| 33 | (structure) | Example 17 | 68 | 2.08 (6) | 508 |

| Example No. | Structure | Starting material | Yield [%] | $R_t$ [min] (method) | Mass $[M+H]^+$ |
|---|---|---|---|---|---|
| 34 | 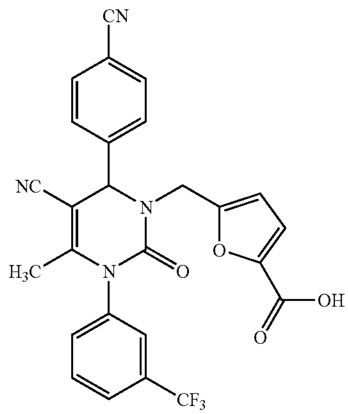 | Example 16 | 75 | 2.41 (5) | 507 |

Example 35

Ethyl 3-(3-bromobenzyl)-4-(4-cyanophenyl)-6-methyl-2-oxo-1-[3-(trifluoromethyl)phenyl]-1,2,3,4-tetrahydropyrimidine-5-carboxylate

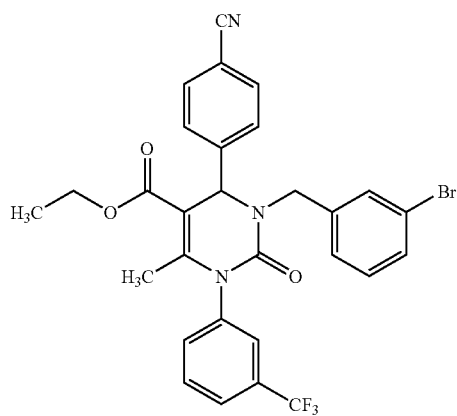 [SMILES: CCOC(=O)C1=C(C)N(c2cccc(C(F)(F)F)c2)C(=O)N(Cc2cccc(Br)c2)C1c1ccc(C#N)cc1]

Sodium hydride (55.9 mg 1.397 mmol; 60% dispersion in mineral oil) is washed with pentane (2×10 ml) and suspended in tetrahydrofuran (10 ml). A solution of ethyl 4-(4-cyanophenyl)-6-methyl-2-oxo-1-[3-(trifluoromethyl)phenyl]-1,2,3,4-tetrahydropyrimidine-5-carboxylate (Example 4A) (500 mg, 1.164 mmol) in tetrahydrofuran (5 ml) is added with stirring. After 5 minutes at room temperature, a solution of 1-bromo-3-(bromomethyl)benzene (320 mg, 1.23 mmol) in tetrahydrofuran (5 ml) is added, and the reaction is stirred at room temperature for 16 h. The solution is quenched with water (50 ml) and extracted with ethyl acetate (3×150 ml). The combined organic phases are washed with brine, dried over anhydrous magnesium sulfate, filtered and concentrated. The yellow residue (approximately 1.05 g) is purified by flash chromatography over silica gel 60 (50 g) with cyclohexane/ethyl acetate (5:1) as eluent.

The product is isolated as an amorphous foam.

Yield: 568 mg (81.5% of th.)

LC-MS (method 6): $R_t$=3.02 min

HPLC (method 1): $R_t$=5.62 min, $\lambda_{max}$=198 nm

MS (ESIpos): m/z=598 (M+H)$^+$ $^1$H-NMR (300 MHz, CDCl$_3$): Δ=7.74-7.56 (m, 4H), 7.55-7.34 (m, 6H), 7.23-7.13 (m, 2H), 5.44 (s, 1H), 5.07 (d, 1H, J=15.3 Hz), 4.16 (q, 2H), 3.91 (d, 1H, J=15.3 Hz), 2.07 (s, 3H), 1.22 (t, 3H) ppm.

Example 36

Ethyl 3-(4-bromobenzyl)-4-(4-cyanophenyl)-6-methyl-2-oxo-1-[3-(trifluoromethyl)phenyl]-1,2,3,4-tetrahydropyrimidine-5-carboxylate

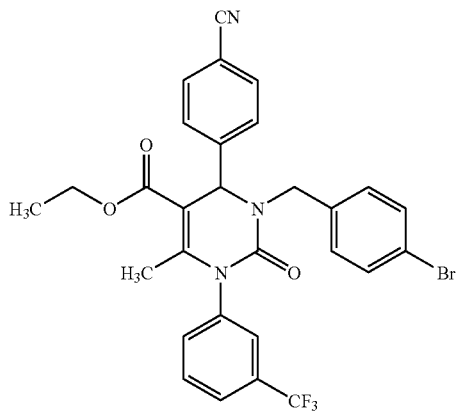 [SMILES: CCOC(=O)C1=C(C)N(c2cccc(C(F)(F)F)c2)C(=O)N(Cc2ccc(Br)cc2)C1c1ccc(C#N)cc1]

The title compound is prepared from Example 4A according to the procedure described for Example 35.

Yield: 565 mg (81.2% of th.) LC-MS (method 6): $R_t$=3.04 min

HPLC (method 1): R.=5.56 min, $\lambda_{max}$=198 nm

MS (ESIpos): m/z=598 (M+H)+

$^1$H-NMR (300 MHz, CDCl$_3$): Δ=7.74-7.56 (m, 4H), 7.55-7.36 (m, 6H), 7.19-7.11 (m, 2H), 5.42 (s, 1H), 5.11 (d, 1H, J=15.3 Hz), 4.15 (m, 2H), 3.82 (d, 1H, J=15.3 Hz), 2.06 (s, 3H), 1.21 (t, 3H) ppm.

Example 37

Ethyl 4-(4-cyanophenyl)-3-{3-[(1E)-3-ethoxy-3-oxoprop-1-en-1-yl]benzyl}-6-methyl-2-oxo-1-[3-(trifluoromethyl)phenyl]-1,2,3,4-tetrahydropyrimidine-5-carboxylate

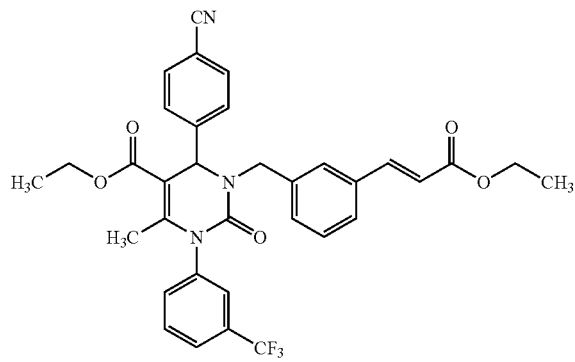 [SMILES: CCOC(=O)/C=C/c1cccc(CN2C(=O)N(c3cccc(C(F)(F)F)c3)C(C)=C(C(=O)OCC)C2c2ccc(C#N)cc2)c1]

To a stirred solution of ethyl 3-(3-bromobenzyl)-4-(4-cyanophenyl)-6-methyl-2-oxo-1-[3-(trifluoro-methyl-)phenyl]-1,2,3,4-tetrahydropyrimidine-5-carboxylate (Example 35) (500 mg, 0.84 mmol) in dimethylformamide (7.0 ml) is added bis(triphenylphosphine)palladium(II) chloride (117.3 mg, 0.17 mmol), ethyl acrylate (457.2 µl, 4.18 mmol) and triethylamine (232.9 µl, 1.67 mmol). The reaction is stirred overnight (16 h) at 120° C., then cooled to room temperature, diluted with dimethylformamide (8 ml) and purified directly by preparative HPLC(RP18 column; eluent: acetonitrile/0.1% aq. formic acid 10:90→10:10). The title compound, which is still slightly impure, is isolated (356 mg) and then chromatographed again over silica gel 60 with cyclo-hexane/ethyl acetate (5:1) as eluent.

Yield: 210 mg (40.7% of th.)
LC-MS (method 6): $R_t$=3.00 min
HPLC (method 2): $R_t$=5.57 min, $\lambda_{max}$=198 nm
MS (ESIpos): m/z=618 (M+H)$^+$
$^1$H-NMR (200 MHz, CDCl$_3$): Δ=7.75-7.56 (m, 5H), 7.55-7.20 (m, 8H), 6.42 (d, 1H, J=16.0 Hz), 5.45 (s, 1H), 5.14 (d, 1H, J=15.3 Hz), 4.28 (q, 2H), 4.15 (m, 2H), 3.93 (d, 1H, J=15.2 Hz), 2.08 (s, 3H), 1.35 (t, 31H), 1.20 (t, 3H) ppm.

Example 38

Ethyl 4-(4-cyanophenyl)-6-methyl-2-oxo-3-[3-(2-thienyl)benzyl]-1-[3-(trifluoromethyl) phenyl]-1,2,3,4-tetrahydropyrimidine-5-carboxylate

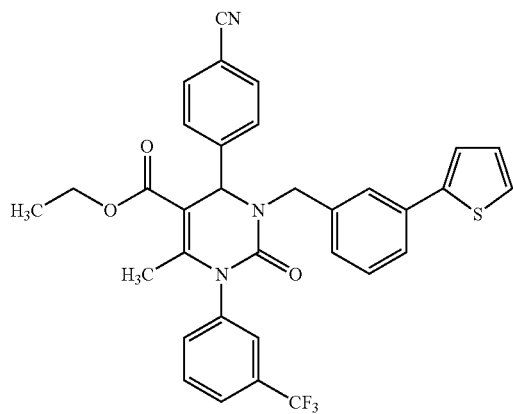 [SMILES: CCOC(=O)C1=C(C)N(c2cccc(C(F)(F)F)c2)C(=O)N(Cc2cccc(-c3cccs3)c2)C1c1ccc(C#N)cc1]

A solution of ethyl 3-(3-bromobenzyl)-4-(4-cyanophenyl)-6-methyl-2-oxo-1-[3-(trifluoromethyl)-phenyl]-1,2,3,4-tetrahydropyrimidin-5-carboxylate (Example 35) (40 mg, 0.07 mmol), 2-thiophen-boronic acid (10.69 mg, 0.08 mmol), 2 M aqueous sodium carbonate (100 µl, 0.2 mmol) and bis-(triphenylphosphine)palladium(II) chloride (4.7 mg, 0.01 mmol) in dimethylformamide (2.0 ml) is stirred at 90° C. overnight (16 h). Additional bis(triphenylphosphine)palladium(II) chloride (4.7 mg, 0.01 mmol) is added, and the reaction is stirred at 90° C. for another 24 h, after which time additional bis(triphenylphosphine)palladium(II) chloride (4.7 mg, 0.01 mmol) is added and the reaction stirred 3 h longer at 90° C. The reaction mixture is diluted with dimethylformamide (5 ml) and purified directly by preparative HPLC(RP18 column; eluent: acetonitrile/0.1% aq. formic acid 10:90→90:10). The product fractions are concentrated and pulled through a thin layer of silica gel 60 with dichloromethane as eluent. Concentration in vacuo gives the title compound.

Yield: 30.2 mg (61.4% of th.)
LC-MS (method 6): $R_t$=3.10 min HPLC (method 2): $R_t$=5.71 min, $\lambda_{max}$=198 nm
MS (ESIpos): m/z=602 (M+H)$^+$
$^1$H-NMR (200 MHz, CDCl$_3$): Δ=7.80-7.05 (m, 15H), 5.49 (s, 1H), 5.19 (d, 1H, J=15.4 Hz), 4.24-4.04 (m, 2H), 3.95 (d, 1H, J=15.2 Hz), 2.07 (s, 3H), 1.39-1.12 (m, 3H) ppm.

Example 39

3-{3-[(E)-2-Carboxyvinyl]benzyl}-4-(4-cyanophenyl)-6-methyl-2-oxo-1-[3-(trifluoromethyl)-phenyl]-1,2,3,4-tetrahydropyrimidine-5-carboxylic acid

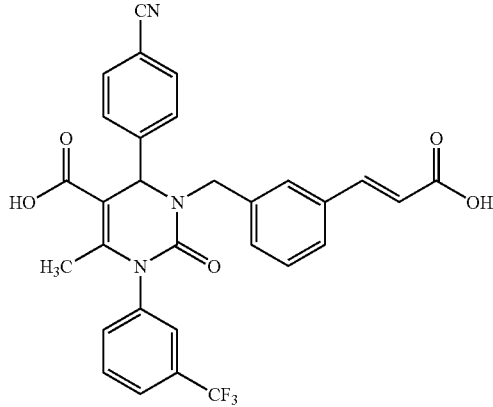 [SMILES: CC1=C(C(=O)O)C(c2ccc(C#N)cc2)N(Cc2cccc(/C=C/C(=O)O)c2)C(=O)N1c1cccc(C(F)(F)F)c1]

To a stirred solution of ethyl 4-(4-cyanophenyl)-3-{3-[(]E)-3-ethoxy-3-oxoprop-1-en-1-yl]benzyl}-6-methyl-1-2-oxo-1-[3-(trifluoromethyl)phenyl]-1,2,3,4-tetrahydropyrimidine-5-carboxylate (Example 37) (50 mg, 0.08 mmol) in tetrahydrofuran (2 ml) is added a solution of sodium hydroxide (32.4 mg, 0.8 mmol) in water (0.5 ml). After stirring at room temperature for 1 hour, ethanol (2 ml) is added. After 16 hours stirring, the pH of the solution is adjusted to 2 with 1 N hydrochloric acid, and the product is extracted with ethyl acetate (3×100 ml). The combined organic phases are washed with brine, dried over anhydrous magnesium sulfate, filtered and concentrated in vacuo. The crude product is purified by preparative HPLC(RP18 column; eluent: acetonitrile/0.1% aq. formic acid 10:90-90:10). The title compound is obtained as a colourless solid.

Yield: 23.6 mg (47.7% of th.)
LC-MS (method 3): $R_t$=2.37 min
HPLC (method 2): R.=4.57 min, $\Delta_{max}$=226 nm
MS (ESIpos): m/z=562 (M+H)$^+$
$^1$H-NMR (300 MHz, DMSO-d$_6$): Δ=12.0 (br. s, 2H), 7.89-7.25 (m, 13H), 6.48 (d, 1H, J=15.9 Hz), 5.45 (s, 1H), 4.9 (d, 1H, J=15.7 Hz), 4.07 (d, 1H, J=15.7 Hz), 2.02 (s, 3H) ppm.

Example 40

Ethyl 4-(4-cyanophenyl)-3-{4-[(1E)-3-ethoxy-3-oxoprop-1-en-1-yl]benzyl}-6-methyl-2-oxo-1-[3-(trifluoromethyl)phenyl]-1,2,3,4-tetrahydropyrimidine-5-carboxylate

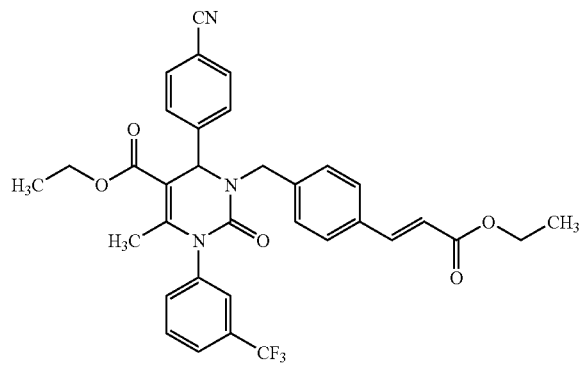 [SMILES: CCOC(=O)/C=C/c1ccc(CN2C(=O)N(c3cccc(C(F)(F)F)c3)C(C)=C(C(=O)OCC)C2c2ccc(C#N)cc2)cc1]

The title compound is prepared from Example 36 according to the procedure described for Example 37.

Yield: 366 mg (66% of th.)
LC-MS (method 6): $R_t$=3.01 min
HPLC (method 2): $R_t$=5.48 min, $\lambda_{max}$=284 nm
MS (ESIpos): m/z=618 (M+H)$^+$
$^1$H-NMR (200 MHz, CDCl$_3$): Δ=7.76-7.17 (m, 13H), 6.44 (d, 1H, J=16 Hz), 5.44 (s, 1H), 5.19 (d, 1H, J=15.4 Hz), 4.28 (q, 2H), 4.13 (m, 2H), 3.86 (d, 1H, J=15.5 Hz), 2.07 (s, 3H), 1.35 (t, 3H), 1.19 (t, 3H) ppm.

Example 41

3-{4-[(E)-2-Carboxyvinyl]benzyl}-4-(4-cyanophenyl)-6-methyl-2-oxo-1-[3-(trifluoromethyl)-phenyl]-1,2,3,4-tetrahydropyrimidine-5-carboxylic acid

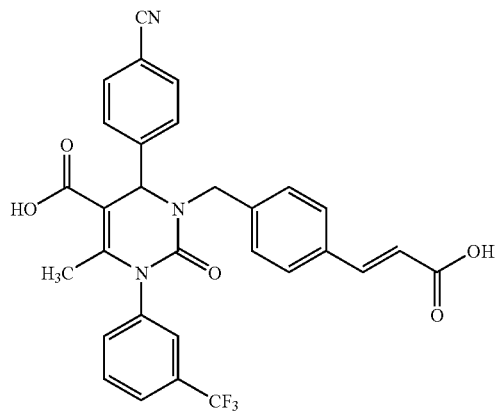 [SMILES: CC1=C(C(=O)O)C(c2ccc(C#N)cc2)N(Cc2ccc(/C=C/C(=O)O)cc2)C(=O)N1c1cccc(C(F)(F)F)c1]

A stirred solution of ethyl 4-(4-cyanophenyl)-3-{4-[(1E)-3-ethoxy-3-oxoprop-1-en-1-yl]benzyl}-6-methyl-1-2-oxo-1-[3-(trifluoromethyl)phenyl]-1,2,3,4-tetrahydropyrimidine-5-carboxylate (Example 40) (100 mg, 0.16 mmol) in ethanol (2 ml) is treated with 10% aq. sodium hydroxide solution (1 ml). After 16 hours, the pH of the reaction solution is adjusted to 2 with 1 N hydrochloric acid, and the crude product is extracted with ethyl acetate (3×150 ml). The combined organic phases are washed with brine, dried over anhydrous magnesium sulfate, filtered and concentrated in vacuo. The residue is purified by preparative HPLC(RP18 column; eluent: acetonitrile/0.1% aq. formic acid 10:90→90:10).

Yield: 16.2 mg (14.5% of th.)
LC-MS (method 3): $R_t$=2.37 min
HPLC (method 2): $R_t$=4.56 min, $\lambda_{max}$=282 nm
MS (ESIpos): m/z=578 (M+NH$_4$)$^+$
$^1$H-NMR (200 MHz, DMSO-d$_6$): Δ=12.5 (br. s, 2H), 8.00-7.23 (m, 13H), 6.52 (d, 1H, J=15.9 Hz), 5.43 (s, 1H), 4.96 (d, 1H, J=15.5 Hz), 4.00 (d, 1H, J=15.3 Hz), 2.02 (s, 3H) ppm.

Example 42

(2E)-3-(4-{[6-(4-Cyanophenyl)-5-(ethoxycarbonyl)-4-methyl-2-oxo-3-[3-(trifluoromethyl)phenyl]-3,6-dihydropyrimidin-1(2fl)-yl]methyl}phenyl)acrylic acid

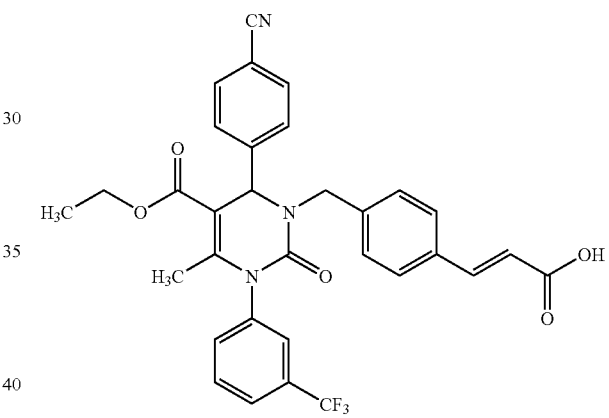

A stirred solution of ethyl 4-(4-cyanophenyl)-3-{4-[(1E)-3-ethoxy-3-oxoprop-1-en-1-yl]benzyl}-6-methyl-1-2-oxo-1-[3-(trifluoromethyl)phenyl]-1,2,3,4-tetrahydropyrimidine-5-carboxylate (Example 40) (100 mg, 0.16 mmol) in ethanol (2 ml) is treated with 10% aq. sodium hydroxide solution (3 ml). After 30 minutes at room temperature, the pH of the solution is adjusted to 2 with 1 N hydrochloric acid, and the crude product is extracted with ethyl acetate (3×150 ml). The combined organic phases are washed with brine, dried over anhydrous magnesium sulfate, filtered and concentrated in vacuo. The residue is purified by preparative HPLC (RP18 column; eluent: acetonitrile/0.1% aq. formic acid 10:90→90:10).

Yield: 9.9 mg (10% of th.)
LC-MS (method 5): $R_t$=2.76 min
MS (ESIpos): m/z=589 (M+H)$^+$
$^1$H-NMR (300 MHz, DMSO-d$_6$): Δ=12.0 (br. s, 1H), 7.90-7.50 (m, 12H), 7.32 (d, 2H), 6.50 (d, 1H, J=16.0 Hz), 5.44 (s, 1H), 4.91 (d, 1H, J=15.7 Hz), 4.08-3.96 (m, 2H), 2.03 (s, 3H), 1.07 (t, 3H) ppm.

Example 43 tert.-Butyl 3-{[6-(4-cyanophenyl)-5-(2-furoyl)-4-methyl-2-oxo-3-[3-(trifluoromethyl)phenyl]-3,6-dihydropyrimidin-1(2H)-yl]methyl}benzoate

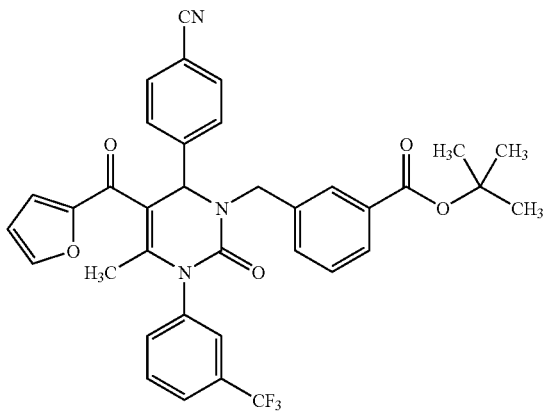 [SMILES: CC1=C(C(=O)c2ccco2)C(c2ccc(C#N)cc2)N(Cc2cccc(C(=O)OC(C)(C)C)c2)C(=O)N1c1cccc(C(F)(F)F)c1]

The title compound is prepared from Example 20A according to the procedure described for Example 35, with the exception that the title compound is purified by preparative HPLC under neutral conditions (RP18 column; eluent: acetonitrile/water 10:90 →90:10).

Yield: 68 mg (62% of th.)

LC-MS (method 3): $R_t$=3.13 min

MS (ESIneg): m/z=640 (M−H)$^-$

HPLC (method 1): $R_t$=5.43 min, $\lambda_{max}$=204 nm $^1$H-NMR (300 MHz, DMSO-d$_6$): Δ=7.99-7.65 (m, 9H), 7.62-7.38 (m, 4H), 7.29-7.23 (m, 1H), 6.67-6.61 (m, 1H), 5.58 (s, 1H), 4.90 (d, 1H, J=15.6 Hz), 4.30 (d, 1H, J=15.6 Hz), 1.54 (s, 12H) ppm.

Example 44

3-[6-(4-Cyanophenyl)-5-(2-furoyl)-4-methyl-2-oxo-3-[3-(trifluoromethyl)phenyl]-3,6-dihydropyrimidin-1(2H)-yl]methyl}benzoic acid

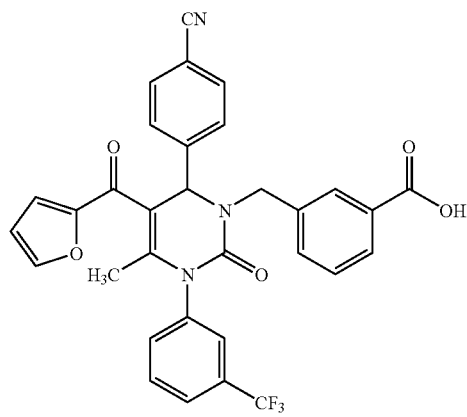 [SMILES: CC1=C(C(=O)c2ccco2)C(c2ccc(C#N)cc2)N(Cc2cccc(C(=O)O)c2)C(=O)N1c1cccc(C(F)(F)F)c1]

tert-Butyl 3-{[6-(4-cyanophenyl)-5-(2-furoyl)-4-methyl-2-oxo-3-[3-(trifluoromethyl)phenyl]-3,6-dihydropyrimidin-1(2H)-yl]methyl}benzoate (Example 43) (50 mg, 0.078 mmol) is dissolved in trifluoroacetic acid (2 ml). After 15 minutes stirring, the solution is concentrated in vacuo and the residue is purified by preparative HPLC(RP18 column; eluent: acetonitrile/water 10:90→90:10).

Yield: 27.8 mg (61% of th.) LC-MS (method 3): $R_t$=2.57 min

MS (ESIpos): m/z=586 (M+H)$^+$ $^1$H-NMR (300 MHz, DMSO-d$_6$): Δ=12.91 (br. s, 1H), 7.94-7.64 (m, 9H), 7.62-7.39 (m, 4H), 7.30-7.21 (m, 1H), 6.68-6.60 (m, 1H), 5.56 (s, 1H), 4.95 (d, 1H, J=15.3 Hz), 4.21 (d, 1H, J=15.3 Hz), 1.54 (s, 3H) ppm.

Example 45

2-[6-(4-Cyanophenyl)-5-(2-furoyl)-4-methyl-2-oxo-3-[3-(trifluoromethyl)phenyl]-3,6-dihydro-pyrimidin-1(2H)-yl]-N-[(4-cyanophenyl)sulfonyl]acetamide

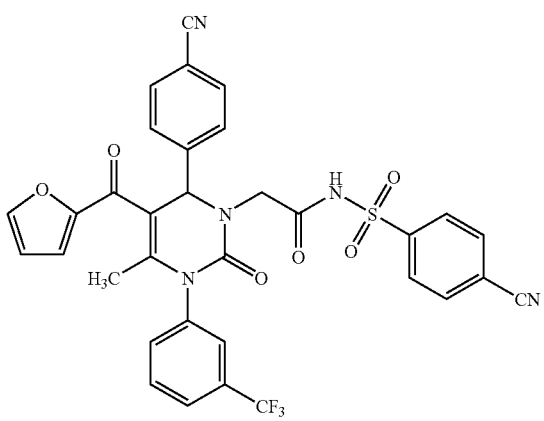 [SMILES: CC1=C(C(=O)c2ccco2)C(c2ccc(C#N)cc2)N(CC(=O)NS(=O)(=O)c2ccc(C#N)cc2)C(=O)N1c1cccc(C(F)(F)F)c1]

A mixture of [6-(4-cyanophenyl)-5-(2-furoyl)-4-methyl-2-oxo-3-[3-(trifluoromethyl)phen-yl]-3,6-dihydropyrimidin-1(2H)-yl]acetic acid (Example 29A) (75 mg, 0.14 mmol), 1,3-dicyclohexyl-carbodiimide (33 mg, 0.16 mmol), 4-cyanobenzene-1-sulfonamide (30 mg, 0.16 mmol) and 4-dimethylaminopyridine (20 mg, 0.16 mol) in dichloromethane (4 ml) is stirred for 48 hours. The product is extracted with dichloromethane, washed with 2 N hydrochloric acid and brine, dried over anhydrous magnesium sulfate, filtered and concentrated. The residue is purified by preparative HPLC (RP18 column; eluent: acetonitrile/water 10:90→90:10).

Yield: 35 mg (34% of th.)

LC-MS (method 5): $R_t$=2.68 min

MS (ESIpos): m/z=674 (M+H)$^+$ $^1$H-NMR (300 MHz, DMSO-d$_6$): Δ=8.15-7.98 (m, 5H), 7.94 (m, 1H), 7.85-7.46 (m, 8H), 7.35 (m, 1H), 6.65 (m, 1H), 5.58 (s, 1H), 4.14 (d, 1H), 3.72 (d, 1H), 1.51 (s, 3H) ppm.

Example 46

2-[6-(4-Cyanophenyl)-5-(2-furoyl)-4-methyl-2-oxo-3-[3-(trifluoromethyl)phenyl]-3,6-dihydropyrimidin-1(2H)-yl]-N-[(2,2,2-trifluoroethyl)sulfonyl]acetamide

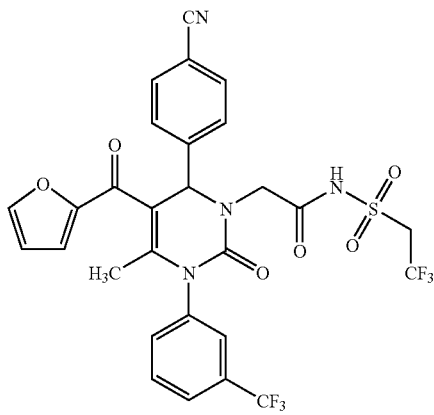 [SMILES: CC1=C(C(=O)c2ccco2)C(c2ccc(C#N)cc2)N(CC(=O)NS(=O)(=O)CC(F)(F)F)C(=O)N1c1cccc(C(F)(F)F)c1]

A solution of [6-(4-cyanophenyl)-5-(2-furoyl)-4-methyl-2-oxo-3-[3-(trifluoromethyl)phen-yl]-3,6-dihydropyrimidin-1(2H)-yl]acetic acid (Example 29A) (75 mg, 0.15 mmol), 2,2,2-trifluoroethane-sulfonamide (23 mg, 0.16 mmol), 1,3-dicyclohexylcarbodiimide (33 mg, 0.16 mmol) and 4-dimethylaminopyridine (20 mg, 0.16 mmol) in dichloromethane (4 ml) is stirred at room temperature for 4 days. The product is extracted with dichloromethane (100 ml), washed with 2 N hydrochloric acid and brine, dried over magnesium sulfate, filtered and concentrated in vacuo. The residue is purified by preparative HPLC(RP18 column; eluent: acetonitrile/0.1% aq. formic acid 30:70→90:10). The title compound is isolated as a colourless solid.

Yield: 32 mg (31% of th.)
LC-MS (method 5): R.=2.90 min
MS (ESIpos): m z=655 (M+H)$^+$
$^1$H-NMR (300 MHz, DMSO-d$_6$): Δ=7.95 (m, 1H), 7.90-7.51 (m, 9H), 7.41 (m, 1H), 6.67 (m, 1H), 5.69 (s, 1H), 4.70-4.47 (m, 2H), 4.29 (d, 1H), 3.68 (d, 1H), 1.58 (s, 3H) ppm.

Example 47 tert.-Butyl 3-{[6-(4-cyanophenyl)-4-methyl-2-oxo-5-(pyridin-3-ylcarbonyl)-3-[3-(trifluoromethyl)-phenyl]-3,6-dihydropyrimidin-1(2H)-yl]methyl}benzoate

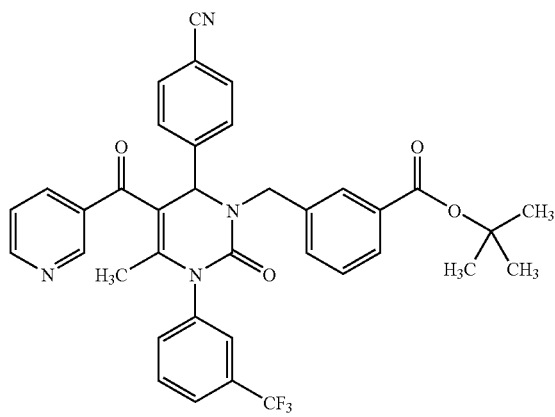 [SMILES: CC1=C(C(=O)c2cccnc2)C(c2ccc(C#N)cc2)N(Cc2cccc(C(=O)OC(C)(C)C)c2)C(=O)N1c1cccc(C(F)(F)F)c1]

The title compound is prepared from Example 21A according to the procedure described for Example 1, with the exception that the title compound is purified by preparative HPLC under neutral conditions (RP18 column; eluent: acetonitrile/water 10:90→90:10).

Yield: 49 mg (34% of th.)
LC-MS (method 5): R$_t$=3.00 min
MS (ESIpos): m/z=653 (M+H)$^+$
HPLC (method 1): R$_t$=5.06 min, λ$_{max}$=198 nm
$^1$H-NMR (300 MHz, DMSO-d$_6$): Δ=8.78 (d, 1H), 8.74-8.67 (m, 1H), 8.00-7.91 (m, 2H), 7.85-7.65 (m, 7H), 7.62-7.51 (m, 3H), 7.49-7.38 (m, 2H), 5.58 (s, 1H), 4.92 (d, 1H), 4.34 (d, 1H), 1.54 (s, 9H), 1.43 (s, 3H) ppm.

Example 48

Methyl 2-{[6-(4-cyanophenyl)-4-methyl-2-oxo-5-(pyridin-3-ylcarbonyl)-3-[3-(trifluoromethyl)-phenyl]-3,6-dihydropyrimidin-1(2H)-yl]methyl}-1,3-oxazol-e-4-carboxylate

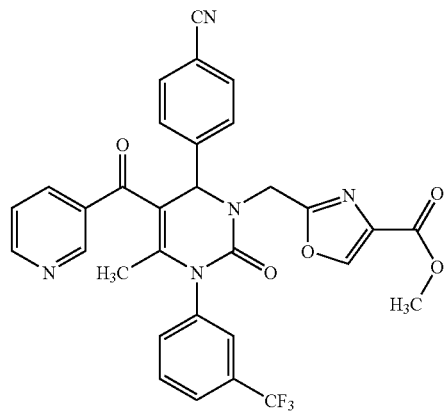 [SMILES: COC(=O)c1coc(CN2C(=O)N(c3cccc(C(F)(F)F)c3)C(C)=C(C(=O)c3cccnc3)C2c2ccc(C#N)cc2)n1]

To a stirred suspension of 4-{6-methyl-2-oxo-5-(pyridin-3-ylcarbonyl)-1-[3-(trifluoromethyl)-phenyl]-1,2,3,4-tetrahydropyrimidin-4-yl}benzonitrile (Example 21A) (100 mg, 0.22 mmol and potassium carbonate (60 mg, 0.43 mmol) in dimethylformamide (3 ml) is added methyl 2-(chloro-methyl)-1,3-oxazole-4-carboxylate (57 mg, 0.32 mmol). The reaction mixture is stirred for 72 hours at room temperature.

The crude product is quenched with water (20 ml) and extracted with ethyl acetate (3×50 ml). The combined organic phases are washed with brine, dried over anhydrous magnesium sulfate, filtered and concentrated. The residue is purified by preparative HPLC(RP18 column; eluent: acetonitrile/water 30:70→490:10).

Yield: 30 mg (23% of th.)
LC-MS (method 6): R$_t$=2.19 min
MS (ESIpos): m/z=602 (M+H)$^+$
HPLC (method 2): R$_t$=4.37 min, λ$_{max}$=200 nm
$^1$H-NMR (300 MHz, DMSO-d$_6$): Δ=8.82 (d, 1H), 8.75-8.69 (m, 2H), 8.09-8.02 (m, 1H), 7.93 (s, 1H), 7.86-7.77 (d, 3H), 7.76-7.67 (d, 2H), 7.60 (d, 2H), 7.52-7.45 (m, 1H), 5.77 (s, 1H), 4.91 (d, 1H), 4.54 (d, 1H), 3.27 (s, 3H), 1.43 (s, 3H) ppm.

Example 49

Methyl 2-{[6-(4-cyanophenyl)-5-(2-furoyl)-4-methyl-2-oxo-3-[3-(trifluoromethyl)phenyl]-3,6-dihydropyrimidin-1(2B)-yl]methyl-1,3-oxazole-4-carboxylate

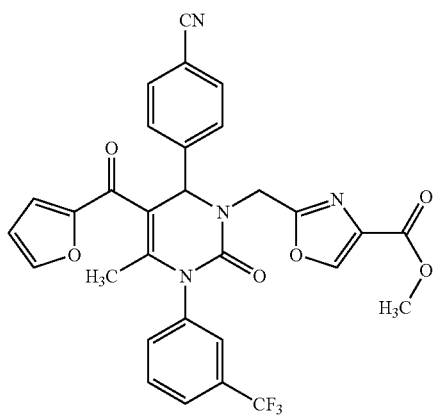 [SMILES: COC(=O)c1coc(CN2C(=O)N(c3cccc(C(F)(F)F)c3)C(C)=C(C(=O)c3ccco3)C2c2ccc(C#N)cc2)n1]

The title compound is prepared from Example 20A according to the procedure described for Example 48, with the exception that the reaction time is 48 hours. The title compound is obtained as a brownish solid.

Yield: 43 mg (32% of th.)
LC-MS (method 6): $R_t$=2.34 min
MS (ESIpos): m/z=591 (M+H)$^+$
$^1$H-NMR (300 MHz, DMSO-d$_6$): Δ=8.72 (s, 1H), 7.95 (m, 1-1), 7.88 (s, 1H), 7.84-7.77 (m, 3H), 7.76-7.68 (m, 2H), 7.53 (d, 2H), 7.43 (d, 1H), 6.69-6.65 (m, 1H), 5.77 (s, 1H), 4.89 (d, 1H), 4.49 (d, 1H), 3.23 (s, 3H), 1.54 (s, 3H) ppm.

Example 50

Methyl 5-{[6-(4-cyanophenyl)-4-methyl-2-oxo-5-(pyridin-3-ylcarbonyl)-3-[3-(trifluoromethyl)-phenyl]-3,6-dihydropyrimidin-1(2H)-yl]methyl}-2-furoate

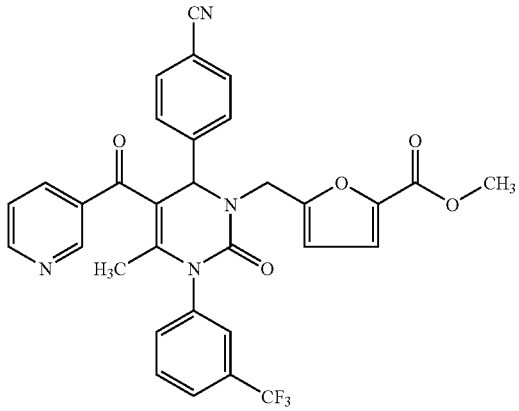 [SMILES: COC(=O)c1ccc(CN2C(=O)N(c3cccc(C(F)(F)F)c3)C(C)=C(C(=O)c3cccnc3)C2c2ccc(C#N)cc2)o1]

To a stirred suspension of (4-{6-methyl-2-oxo-5-(pyridin-3-ylcarbonyl)-1-[3-(trifluoromethyl)-phenyl]-1,2,3,4-tetrahydropyrimidin-4-yl}benzonitrile (Example 21A) (1.00 mg, 0.22 mmol) and potassium carbonate (60 mg, 0.43 mmol) in dimethylformamide (3 ml) is added methyl 5-(chloromethyl)-2-furoate (57 mg, 0.32 mmol). The suspension is stirred at room temperature for 72 hours. The mixture is diluted with methanol (5 ml) and purified directly by preparative HPLC(RP18 column; eluent: acetonitrile/water 10:90→90:10).

Yield: 20 mg (12% of th.)
HPLC (method 1): $R_t$=4.56 min, $\lambda_{max}$=194 nm
MS (ESIpos): m/z=601 (M+H)$^+$
$^1$H-NMR (300 MHz, DMSO-d$_6$): Δ=8.78 (d, 1H), 8.72 (m, 1H), 7.99 (m, 1H), 7.94 (s, 1H), 7.85-7.76 (m, 3H), 7.71 (d, 1H), 7.54 (d, 2H), 7.47 (m, 1H), 7.15 (d, 1H), 6.51 (s, 1H), 5.65 (s, 1H), 4.81 (d, 1H), 4.48 (d, 1H), 3.78 (s, 3H), 1.41 (s, 3H) ppm.

Example 51

Methyl 5-{([6-(4-cyanophenyl)-5-(2-furoyl)-4-methyl-2-oxo-3-[3-(trifluoromethyl)phenyl]-3,6-dihydropyrimidin-1(2H)-yl]methyl}-2-furoate

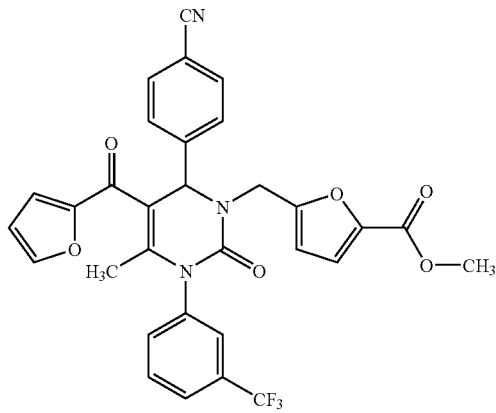 [SMILES: COC(=O)c1ccc(CN2C(=O)N(c3cccc(C(F)(F)F)c3)C(C)=C(C(=O)c3ccco3)C2c2ccc(C#N)cc2)o1]

The title compound is prepared from Example 20A according to the procedure described for Example 50, with the exception that the reaction time is 48 hours.

Yield: 40 mg (27% of th.)
LC-MS (method 6): $R_t$=2.50 min
MS (ESIpos): m/z=590 (M+H)+
$^1$H-NMR (300 MHz, DMSO-d$_6$): Δ=8.03-7.64 (m, 7H), 7.47 (d, 2H), 7.30 (d, 1H), 7.15 (d, 1H), 6.70-6.62 (m, 1H), 6.49 (d, 1H), 5.64 (s, 1H), 4.80 (d, 1H), 4.44 (d, 1H), 3.79 (s, 3H), 1.52 (s, 3H) ppm.

Example 52

5-{[6-(4-Cyanophenyl)-5-(2-furoyl)-4-methyl-2-oxo-3-[3-(trifluoromethyl)phenyl]-3,6-dihydro-pyrimidin-1(2H)-yl]methyl}-2-furoic acid

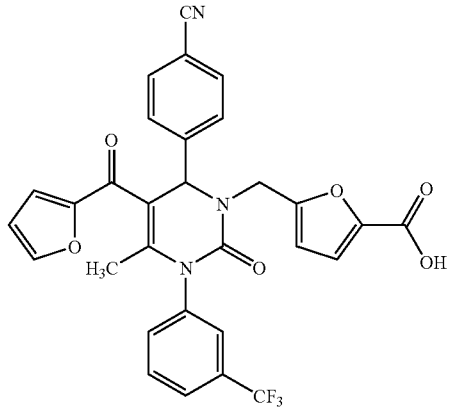 [SMILES: CC1=C(C(=O)c2ccco2)C(c2ccc(C#N)cc2)N(Cc2ccc(C(=O)O)o2)C(=O)N1c1cccc(C(F)(F)F)c1]

To a stirred solution of methyl 5-{[6-(4-cyanophenyl)-5-(2-furoyl)-4-methyl-2-oxo-3-[3-(trifluoro-methyl)-phenyl]-3,6-dihydropyrimidin-1(2H)-yl]methyl}-2-furoate (Example 51) (30 mg, 0.51 mmol) in tetrahydrofuran (1.5 ml) is added a solution of lithium hydroxide (2.4 mg, 0.10 mmol) in water (1.5 ml). The reaction is stirred at room temperature overnight (16 h), then acidified with 1 N hydrochloric acid. A precipitate is obtained. Methanol (7 ml) is added, and the crude product is purified by preparative HPLC (RP18 column; eluent: acetonitrile/0.1% aq. formic acid 30:70→90:10).

Yield: 19 mg (63% of th.)
LC-MS (method 5): R.=2.27 min
MS (ESIpos): m/z=576 (M+H)$^+$
$^1$H-NMR (300 MHz, DMSO-d$_6$): Δ=13.0 (br. s, 1H), 7.93 (d, 1H), 7.87 (s, 1H), 7.79-7.76 (m, 3H), 7.76-7.65 (m, 2H), 7.48 (d, 2H), 7.30 (d, 1H), 7.06 (d, 1H), 6.70-6.62 (m, 1H), 6.46 (d, 1H), 5.63 (s, 1H), 4.86 (d, 1H), 1.52 (s, 3H) ppm.

Example 53

2{[-furoyl)-4-methyl-2-oxo-3-[3-(trifluoromethyl)phenyl]-3,6-dihydro-pyrimidin-[(2R)-yl]methyl}-1,3-oxazole-4-carboxylic acid

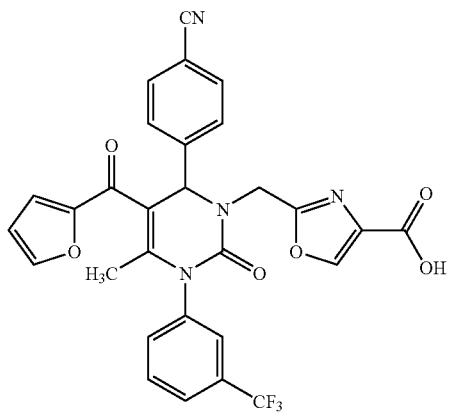 [SMILES: CC1=C(C(=O)c2ccco2)C(c2ccc(C#N)cc2)N(Cc2nc(C(=O)O)co2)C(=O)N1c1cccc(C(F)(F)F)c1]

The title compound is prepared from Example 49 according to the procedure described for Example 52. The title compound is isolated as a brownish amorphous solid.
Yield: 24 mg (80% of th.)
LC-MS (method 5): R$_t$=2.34 min
MS (ESIpos): m/z=577(M+H)$^+$
$^1$H-NMR (300 MHz, DMSO-d$_6$): Δ=13.0 (br. S, 1H), 8.59 (s, 1H), 7.75 (d, 1H), 7.90-7.66 (m, 6H), 7.54 (d, 2H), 7.45 (d, 1H), 6.69-6.63 (m, 1H), 5.77 (s, 1H), 4.91 (d, 1H), 4.41 (d, 1H), 1.54 (s, 3H) ppm.

Example 54

3-{[6-(4-Cyanophenyl)-4-methyl-2-oxo-5-(pyridin-3-ylcarbonyl)-3-[3-(trifluoromethyl)phenyl]-3,6-dihydropyrimidin-1(2H)-yl]methyl}benzoic acid

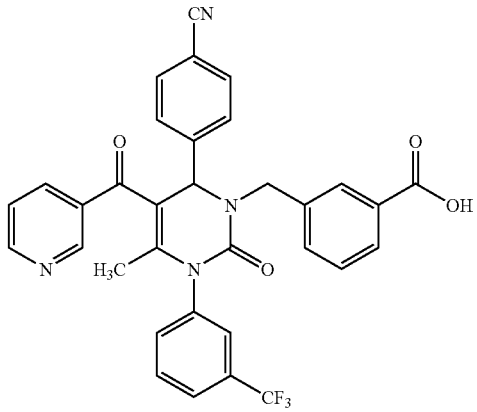 [SMILES: CC1=C(C(=O)c2cccnc2)C(c2ccc(C#N)cc2)N(Cc2cccc(C(=O)O)c2)C(=O)N1c1cccc(C(F)(F)F)c1]

The title compound is prepared from Example 47 according to the procedure described for Example 44, with the exception that the reaction time is 30 minutes.
Yield: 30 mg (78% of th.)
HPLC (method 1): R$_t$=4.36 min, λ$_{max}$=196 nm
LC-MS (method 3): R$_t$=2.46 min
MS (ESIpos): m/z=597 (M+H)+
$^1$H-NMR (300 MHz, DMSO-d$_6$): Δ=13.0 (br. s, 1H), 8.78 (d, 1H), 8.70 (m, 1H), 8.00-7.89 (m, 2H), 7.88-7.77 (m, 5H), 7.76-7.64 (m, 2H), 7.61-7.52 (m, 3H), 7.49-7.39 (m, 2H), 5.55 (s, 1H), 4.98 (d, 1H), 4.23 (d, 1H), 1.42 (s, 3H) ppm.

Example 55

2-[6-(4-Cyanophenyl)-4-methyl-2-oxo-5-(pyridin-3-ylcarbonyl)-3-[3-(trifluoromethyl)phenyl]-3,6-dihydropyrimidin-1(2H)-yl]-N-[(2,2,2-trifluoroethyl)sulfonyl]acetamide

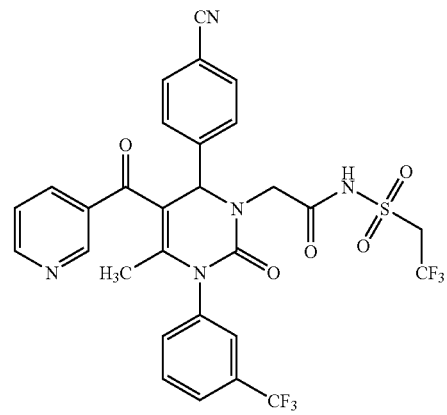 [SMILES: CC1=C(C(=O)c2cccnc2)C(c2ccc(C#N)cc2)N(CC(=O)NS(=O)(=O)CC(F)(F)F)C(=O)N1c1cccc(C(F)(F)F)c1]

The title compound is prepared from Example 31A according to the procedure described for Example 46, with the exception that the title compound is purified by preparative HPLC under neutral conditions (RP18 column; eluent: acetonitrile/water 30:7→90:10).
Yield: 37 mg (55% of th.)
HPLC (method 1): R$_t$=4.38 min, λ$_{max}$=234 nm
LC-MS (method 5): R.=2.68 min
MS (ESIpos): m/z=666 (M+H)$^+$, $^1$H-NMR (300 MHz, DMSO-d$_6$): Δ=8.86 (d, 1H), 8.73 (m, 1H), 8.06 (m, 1H), 7.92-7.61 (m, 8H), 7.54-7.46 (m, 1H), 5.70 (s, 1H), 4.62 (m, 2H), 4.31 (d, 1H), 3.80 (d, 1H), 1.45 (s, 3H) ppm.

Example 56

2-[6-(4-Cyanophenyl)-4-methyl-2-oxo-5-(pyridin-3-ylcarbonyl)-3-[3-(trifluoromethyl)phenyl]-3,6-dihydropyrimidin-1(2H)-yl]-N-[(4-cyanophenyl)sulfonyl-]acetamide

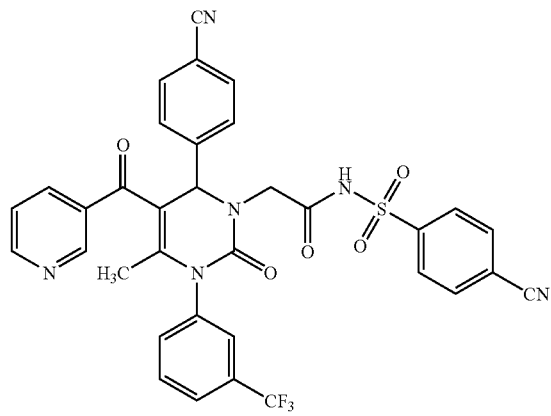 [SMILES: CC1=C(C(=O)c2cccnc2)C(c2ccc(C#N)cc2)N(CC(=O)NS(=O)(=O)c2ccc(C#N)cc2)C(=O)N1c1cccc(C(F)(F)F)c1]

The title compound is prepared from Example 31A according to the procedure described for Example 45, with the exception that the title compound is purified by preparative HPLC(RP18 column; eluent: acetonitrile/water 30:70-90:10).

Yield: 18 mg (47% of th.)
LC-MS (method 5): R$_t$=2.58 min
MS (ESIpos): m/z=685 (M+H)$^+$
HPLC (method 1): R$_t$=4.39 min, λ$_{max}$=234 nm
$^1$H-NMR (300 MHz, DMSO-d$_6$): Δ=8.81 (d, 1H), 8.72 (m, 1H), 8.11-7.97 (m, 5H), 7.87-7.75 (m, 3H), 7.74-7.53 (m, 5H), 7.52-7.42 (m, 1H), 5.59 (s, 1H), 5.55 (d, 2H), 4.17 (d, 1H), 3.80 (d, 1H), 1.41 (s, 3H) ppm.

Example 57

Allyl(4R)-3-[(benzyloxy)methyl]-4-(4-cyanophenyl)-6-methyl-2-oxo-1-[3-(trifluoromethyl)-phenyl]-1,2,3,4-tetrahydropyrimidine-5-carboxylate

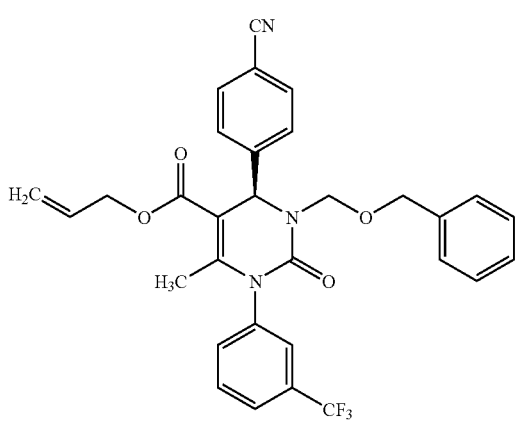 [SMILES: C=CCOC(=O)C1=C(C)N(c2cccc(C(F)(F)F)c2)C(=O)N(COCc2ccccc2)[C@@H]1c1ccc(C#N)cc1]

50 mg (0.11 mmol) of Example 6A are dissolved in 2 ml dry tetrahydrofuran, 9.5 mg (0.24 mmol) sodium hydride are added, and the mixture is stirred at room temperature for 15 min. 23.1 mg (0.15 mmol) chloromethyl benzyl ether are added, and the reaction mixture is stirred at room temperature overnight. The mixture is partitioned between ethyl acetate and aqueous ammonium chloride solution, the organic extract is washed with water, dried over magnesium sulfate and evaporated in vacuo. The crude product is enriched by column chromatography over silica gel (eluent cyclohexane/ethyl acetate 3:1) and is used as such for further reactions.

Yield: 37 mg (54% of th.)
$^1$H-NMR (400 MHz, DMSO-d$_6$): Δ=1.98 (s, 3H), 4.40-4.50 (m, 2H), 4.60 (d, 2H), 4.68 (d, 1H), 5.12-5.23 (m, 3H), 5.68 (s, 1H), 5.90 (ddt, 1H), 7.10-7.90 (m, 13H) ppm.

Example 58

(4R)-3-[(Benzyloxy)methyl]-4-(4-cyanophenyl)-6-methyl-2-oxo-1-[3-(trifluoromethyl)phenyl]-1,2,3,4-tetrahydropyrimidine-5-carboxylic acid

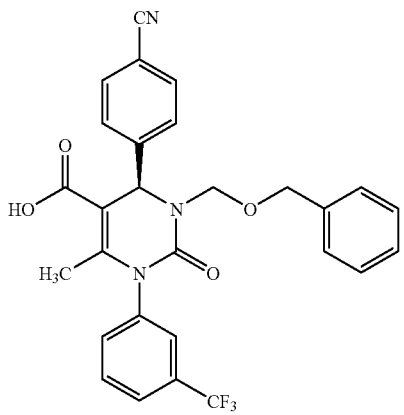 [SMILES: CC1=C(C(=O)O)[C@@H](c2ccc(C#N)cc2)N(COCc2ccccc2)C(=O)N1c1cccc(C(F)(F)F)c1]

485 mg (0.86 mmol) of Example 57 and 112 mg (1.30 mmol) morpholine are dissolved under argon in 5 ml tetrahydrofuran at room temperature. 50 mg (0.04 mmol) tetrakis(triphenyl-phosphine)palladium(0) are added, and the mixture is reacted for 30 min at room temperature. The solvent is evaporated in vacuo, the remainder is dissolved in ethyl acetate and washed with aqueous ammonium chloride solution. The organic phase is dried over magnesium sulfate and evaporated to dryness. The crude product is purified by preparative RP-HPLC with a water/acetonitrile gradient.

Yield: 97 mg (21% of th.)
$^1$H-NMR (300 MHz, DMSO-d$_6$): Δ=1.98 (s, 3H), 4.40 (d, 1H), 4.46 (d, 1H), 4.71 (d, 1H), 5.12 (d, 1H), 5.17 (s, 1H), 7.10-7.20 (m, 2H), 7.22-7.32 (m, 3H), 7.53-7.65 (m, 3H), 7.55-7.65 (m, 3H), 7.68-7.75 (m, 2H), 7.78-7.89 (m, 3H), 12.62 (br. s, 1H) ppm.

In analogy to the procedure for Example 23A, the following compounds are prepared:

| Example No. | Structure | Starting materials | Yield [%] | $R_t$ [min] (method) | Mass [M + H]$^+$ |
|---|---|---|---|---|---|
| 59 | 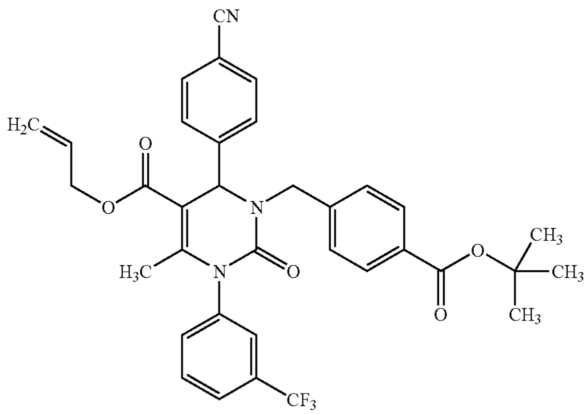 [SMILES: C=CCOC(=O)C1=C(C)N(c2cccc(C(F)(F)F)c2)C(=O)N(Cc2ccc(C(=O)OC(C)(C)C)cc2)C1c1ccc(C#N)cc1] | Example 5A; tert.-butyl 4-bromomethyl-benzoate | 69 | 5.90 (1) | 632 |
| 60 | 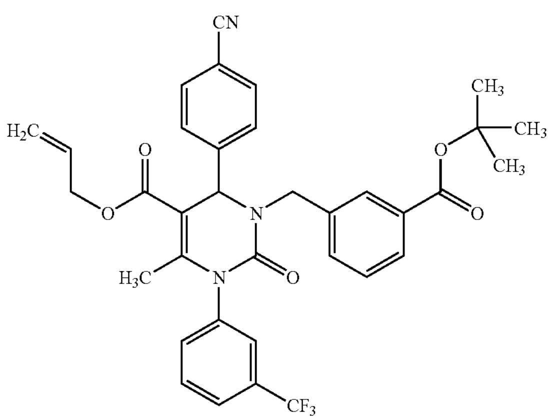 [SMILES: C=CCOC(=O)C1=C(C)N(c2cccc(C(F)(F)F)c2)C(=O)N(Cc2cccc(C(=O)OC(C)(C)C)c2)C1c1ccc(C#N)cc1] | Example 5A; tert.-butyl 3-chloromethyl-benzoate | 59 | 5.73 (2) | 632 |
| 61 | 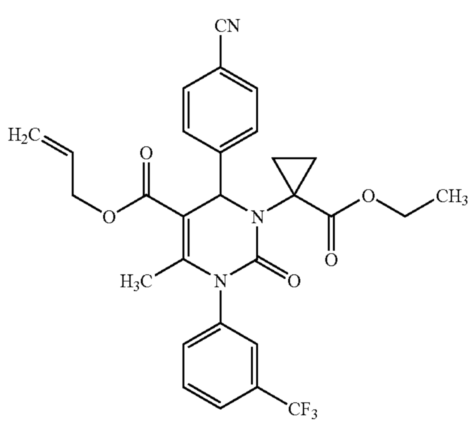 [SMILES: C=CCOC(=O)C1=C(C)N(c2cccc(C(F)(F)F)c2)C(=O)N(C2(C(=O)OCC)CC2)C1c1ccc(C#N)cc1] | Example 5A; ethyl 2-bromo-4-chloro-butyrate | 36 | 5.19 (2) | 554 |

In analogy to the procedure for Example 26A, the following compounds are prepared:

| Example No. | Structure | Starting material | Yield [%] | $R_t$ [min] (method) | Mass $[M + H]^+$ |
|---|---|---|---|---|---|
| 62 | 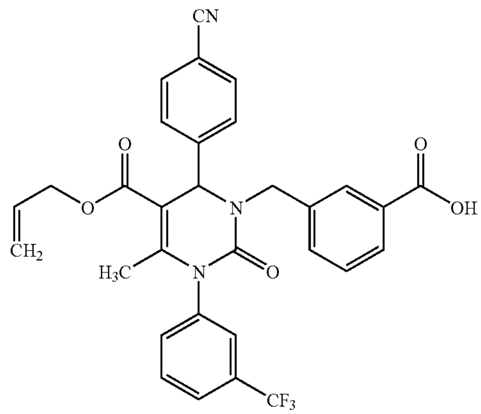 [SMILES: C=CCOC(=O)C1=C(C)N(c2cccc(C(F)(F)F)c2)C(=O)N(Cc2cccc(C(=O)O)c2)C1c1ccc(C#N)cc1] | Example 60 | 84 | 5.02 (2) | 576 |
| 63 | 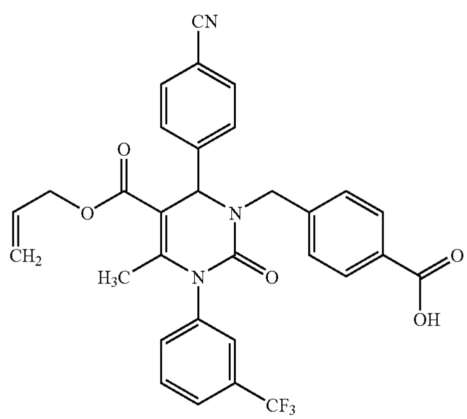 [SMILES: C=CCOC(=O)C1=C(C)N(c2cccc(C(F)(F)F)c2)C(=O)N(Cc2ccc(C(=O)O)cc2)C1c1ccc(C#N)cc1] | Example 59 | 84 | 5.04 (2) | 576 |

Example 64

1-[6-(4-Cyanophenyl)-5-(ethoxycarbonyl)-4-methyl-2-oxo-3-[3-(trifluoromethyl)phenyl]-3,6-dihydropyrimidin-)-yl]cyclopropanecarboxylic acid

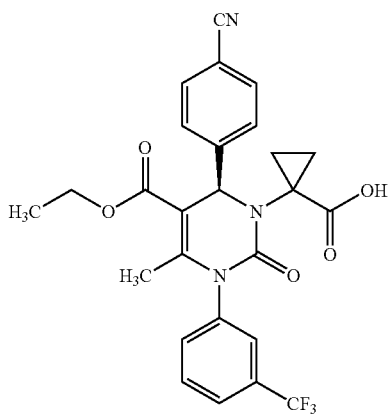 [SMILES: CCOC(=O)C1=C(C)N(c2cccc(C(F)(F)F)c2)C(=O)N(C2(C(=O)O)CC2)[C@@H]1c1ccc(C#N)cc1]

100 mg (0.18 mmol) of Example 61 are suspended in 1 ml tetrahydrofuran, and 1 ml methanol and 0.36 ml 2 N aqueous sodium hydroxide solution are added. The reaction mixture is stirred for 30 min at room temperature, and is then partitioned between 2 N hydrochloric acid and ethyl acetate. The organic extract is dried over magnesium sulfate and evaporated to dryness in vacuo. The crude product consists of a mixture of partially hydrolyzed and transesterified material. The crude product is redissolved in 2 ml ethanol, 102 mg (0.32 mmol) sodium ethanolate are added, and the mixture is stirred at room temperature overnight and then worked up as before. The crude product is purified by RP-HPLC with a water/acetonitrile gradient.

Yield: 10 mg (12% of th.)

$^1$H-NMR (300 MHz, DMSO-d$_6$): Δ=1.00-1.55 (m, 7H), 2.02 (s, 3H), 3.98-4.10 (m, 2H), 5.45 (s, 1H), 7.56-7.87 (m, 8H), 12.1 (br. s, 1H) ppm.

Example 65

3-(1-Carboxycyclopropyl)-4-(4-cyanophenyl)-6-methyl-2-oxo-1-[3-(trifluoromethyl)phenyl]-1,2,3,4-tetrahydropyrimidine-5-carboxylic acid

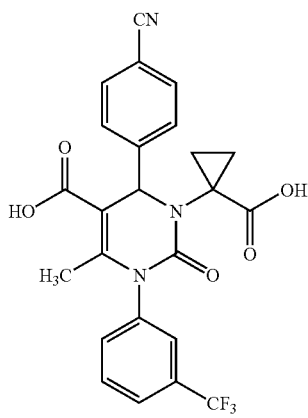 [SMILES: CC1=C(C(=O)O)C(c2ccc(C#N)cc2)N(C2(C(=O)O)CC2)C(=O)N1c1cccc(C(F)(F)F)c1]

This compound is isolated in 22% yield as side product of the preparation of Example 64.

$^1$H-NMR (300 MHz, DMSO-$d_6$): Δ=1.00-1.20 (m, 1H), 1.32-1.56 (m, 3H), 2.00 (s, 3H), 5.47 (s, 1H), 7.55-7.90 (m, 8H), 12.30 (br. s, 2H) ppm.

Example 66

Allyl 4-(4-cyanophenyl)-6-methyl-2-oxo-3-(2-oxo-2-{[(2,2,2-trifluoroethyl)-sulfonyl]amino}ethyl)-1-[3-(trifluoromethyl)phenyl]-1,2,3,4-tetrahydropyrimidine-5-carboxylate

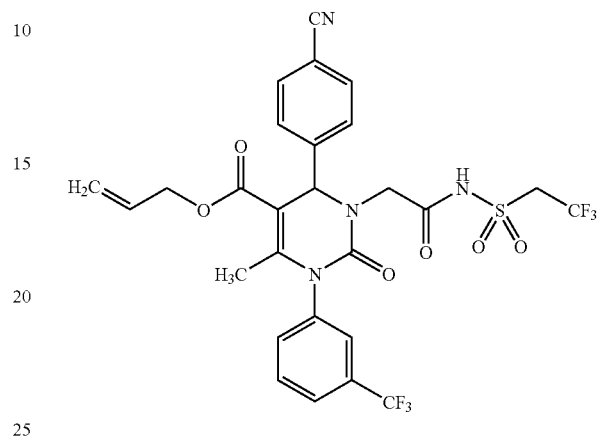

75 mg (0.15 mmol) of Example 26A, 26.9 mg (0.17 mmol) 2,2,2-trifluoroethansulfonamide, 34.1 mg (0.17 mmol) 1,3-dicyclohexylcarbodiimide and 20.2 mg (0.17 mmol) 4-N,N-dimethyl-aminopyridine are dissolved in 4 ml dichloromethane and reacted at room temperature for 60 hours. The reaction mixture is washed with 2 N hydrochloric acid, dried over magnesium sulfate and evaporated to dryness in vacuo. The crude product is purified by preparative HPLC with a water/acetonitrile gradient.

Yield: 90 mg (93% of th.)

$^1$H-NMR (300 MHz, DMSO-$d_6$): Δ=2.0 (s, 3H), 3.80 (d, 1H), 4.21 (d, 1H), 4.46-4.67 (m, 4H), 5.08-5.20 (m, 2H), 5.58 (s, 1H), 5.75-6.90 (m, 1H), 7.60-7.93 (m, 8H) ppm.

In analogy to the procedure for Example 66, the following compounds are prepared:

| Example No. | Structure | Starting materials | Yield [%] | $R_t$ [min] (method) | Mass $[M + H]^+$ |
|---|---|---|---|---|---|
| 67 | (structure shown) | Example 26A; 4-trifluoromethylbenzene-sulfonamide | 32 | 5.30 (2) | 707 |

-continued

| Example No. | Structure | Starting materials | Yield [%] | R$_t$ [min] (method) | Mass [M + H]$^+$ |
|---|---|---|---|---|---|
| 68 | 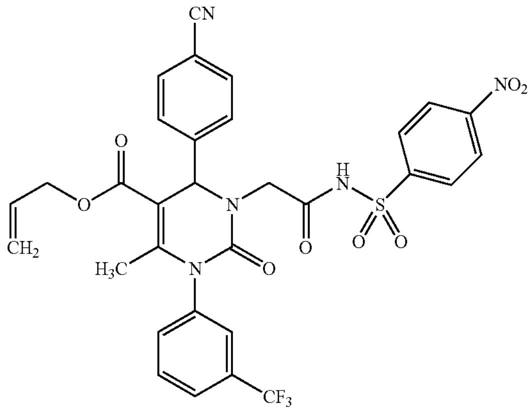 [SMILES: C=CCOC(=O)C1=C(C)N(c2cccc(C(F)(F)F)c2)C(=O)N(CC(=O)NS(=O)(=O)c2ccc([N+](=O)[O-])cc2)C1c1ccc(C#N)cc1] | Example 26A; 4-nitrobenzene-sulfonamide | 91 | 5.15 (2) | 684 |
| 69 | 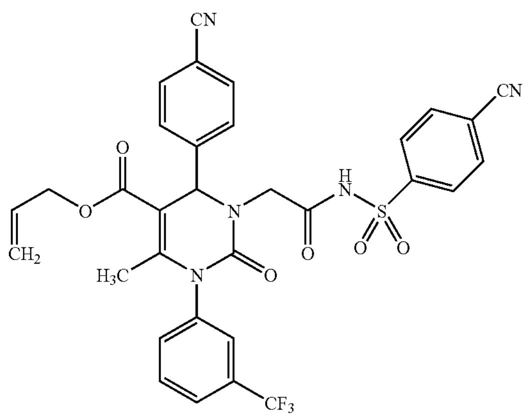 [SMILES: C=CCOC(=O)C1=C(C)N(c2cccc(C(F)(F)F)c2)C(=O)N(CC(=O)NS(=O)(=O)c2ccc(C#N)cc2)C1c1ccc(C#N)cc1] | Example 26A; 4-cyano-benzene-sulfonamide | 32 | 5.04 (2) | 664 |
| 70 | 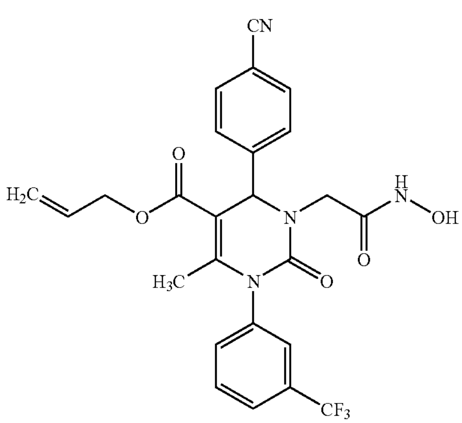 [SMILES: C=CCOC(=O)C1=C(C)N(c2cccc(C(F)(F)F)c2)C(=O)N(CC(=O)NO)C1c1ccc(C#N)cc1] | Example 26A; N-hydroxyl-amine hydrochloride | 54 | 4.78 (2) | 515 |

-continued
| Example No. | Structure | Starting materials | Yield [%] | $R_t$ [min] (method) | Mass $[M + H]^+$ |
|---|---|---|---|---|---|
| 71 | 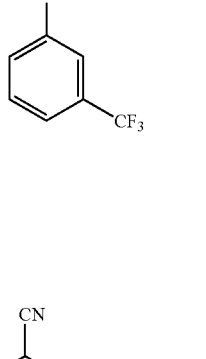 | Example 25A; 2,2,2-trifluoro-ethansulfonamide | 51 | 4.68 (1) | 603 |
| 72 | 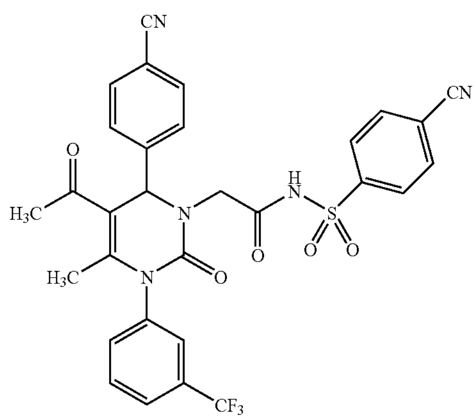 [SMILES: CC(=O)C1=C(C)N(c2cccc(C(F)(F)F)c2)C(=O)N(CC(=O)NS(=O)(=O)c2ccc(C#N)cc2)C1c1ccc(C#N)cc1] | Example 25A; 4-cyano-benzene-sulfonamide | 70 | 4.67 (1) | 622 |
| 73 | 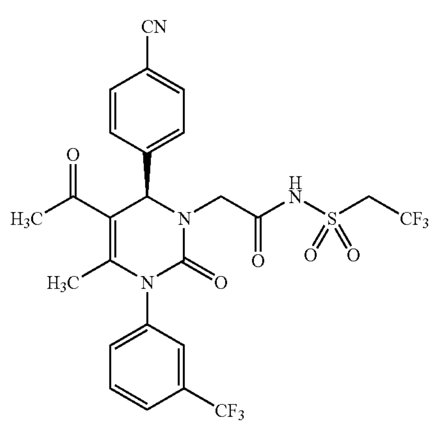 [SMILES: CC(=O)C1=C(C)N(c2cccc(C(F)(F)F)c2)C(=O)N(CC(=O)NS(=O)(=O)CC(F)(F)F)[C@@H]1c1ccc(C#N)cc1] | Example 27A; 2,2,2-trifluoro-ethansulfonamide | 57 | 4.72 (1) | 603 |

-continued

| Example No. | Structure | Starting materials | Yield [%] | $R_t$ [min] (method) | Mass $[M + H]^+$ |
|---|---|---|---|---|---|
| 74 | 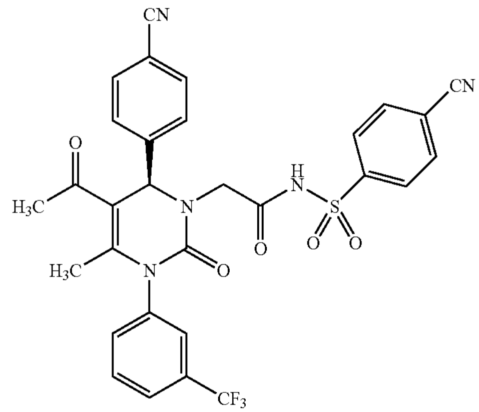 [SMILES: CC(=O)C1=C(C)N(c2cccc(C(F)(F)F)c2)C(=O)N(CC(=O)NS(=O)(=O)c2ccc(C#N)cc2)[C@@H]1c1ccc(C#N)cc1] | Example 27A; 4-cyano-benzene-sulfonamide | 82 | 4.72 (1) | 622 |

Example 75

4-(4-Cyanophenyl)-6-methyl-2-oxo-3-(2-oxo-2-{[(2,2,2-trifluoroethyl)sulfonyl]amino) ethyl)-1-[3-(trifluoromethyl)phenyl]-1,2,3,4-tetrahydropyrimidin-e-5-carboxylic acid

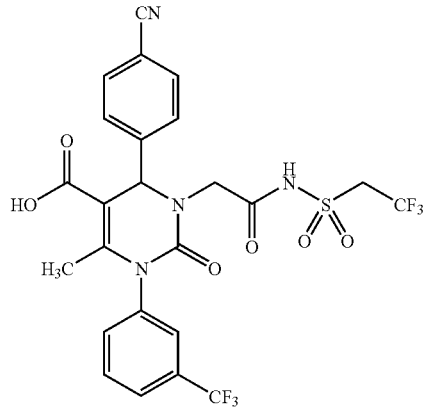 [SMILES: CC1=C(C(=O)O)C(c2ccc(C#N)cc2)N(CC(=O)NS(=O)(=O)CC(F)(F)F)C(=O)N1c1cccc(C(F)(F)F)c1]

140 mg (0.22 mmol) of Example 66 and 28.4 mg (0.33 mmol) morpholine are dissolved under argon in 2 ml tetrahydrofuran at room temperature. 12.5 mg (0.01 mmol) tetrakis(triphenyl-phosphine)palladium(0) are added, and the mixture is reacted for 30 min at room temperature. The solvent is evaporated in vacuo, the remainder is dissolved in ethyl acetate and washed with 2 N hydrochloric acid. The organic phase is dried over magnesium sulfate and evaporated to dryness. The crude product is purified by preparative RP-HPLC with a water/acetonitrile gradient.

Yield: 73 mg (55% of th.)

$^1$H-NMR (400 MHz, DMSO-$d_6$): Δ=2.04 (s, 3H), 3.75 (br. d, 1H), 4.23 (d, 1H), 4.52-4.70 (m, 2H), 5.55 (s, 1H), 7.60-7.68 (m, 3H), 7.70-7.75 (m, 2H), 7.81 (d, 1H), 7.89 (d, 2H), 12.12 (br. s, 1H) ppm.

Example 76

2-Hydroxyethyl 4-(4-cyanophenyl)-6-methyl-2-oxo-3-(2-oxo-2-{[(2,2,2-trifluoroethyl)sulfonyl]-amino}ethyl)-1-[3-(trifluoromethyl)phenyl]-1,2,3,4-tetrahydropyrimidine-5-carboxylate

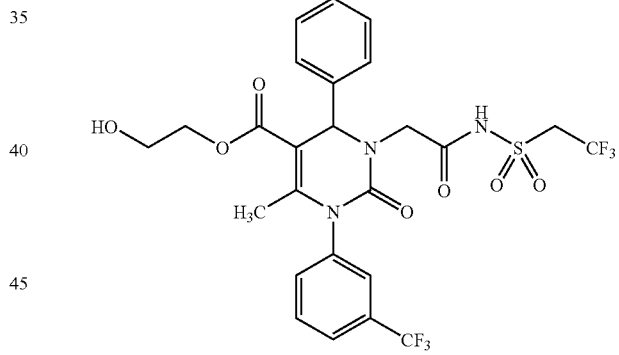

50 mg (0.08 mmol) of Example 75, 11.4 mg (0.09 mmol) 2-bromoethanol and 16.0 mg (0.12 mmol) N,N-diisopropylethyl amine are dissolved in 2 ml dimethylformamide and stirred at 70° C. overnight. Additional 11.4 mg (0.09 mmol) 2-bromoethanol and 16.0 mg (0.12 mmol) N,N-diisopropylethylamine are added and stirring at 70° C. is continued overnight. The mixture is partitioned between ethyl acetate and 2N hydrochloric acid, the organic layer is dried over magnesium sulfate and evaporated to dryness in vacuo. The crude product is purified by column chromatography over silica gel (eluent: dichloromethane/methanol 100:3).

Yield: 5.5 mg (9% of th.)

$^1$H-NMR (300 MHz, DMSO-$d_6$): Δ=2.04 (s, 3H), 3.15-3.40 (m, 2H), 3.52 (t, 2H), 4.01 (dt, 2H), 4.15-4.35 (m, 3H), 5.57 (s, 1H), 7.58-7.68 (m, 3H), 7.72 (t, 2H), 7.77-7.90 (m, 3H) ppm.

Example 77

4-{[5-[(Allyloxy)carbonyl]-6-(4-cyanophenyl)-4-methyl-2-oxo-3-[3-(trifluoromethyl)phenyl]-3,6-dihydropyrimidin-1 (2R)-yl]sulfonyl}benzoic acid

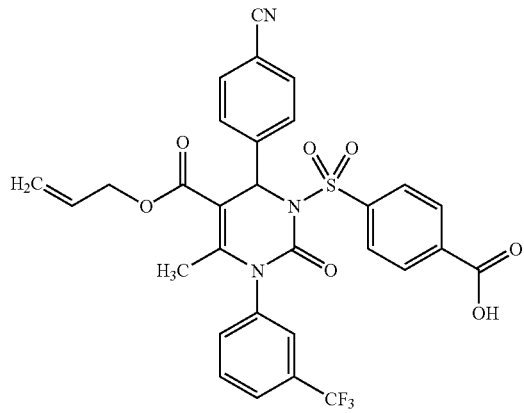 [SMILES: C=CCOC(=O)C1=C(C)N(c2cccc(C(F)(F)F)c2)C(=O)N(S(=O)(=O)c2ccc(C(=O)O)cc2)C1c1ccc(C#N)cc1]

100 mg (0.23 mmol) of Example 5A are dissolved in 4 ml dioxane and cooled to 0° C. 19.9 mg (0.50 mmol) sodium hydride are added, and the mixture is warmed to room temperature and reacted for 30 min. 60.0 mg (0.27 mmol) 4-(chlorosulfonyl)benzoic acid are added as solution in dioxane, and stirring is continued for 1 hour. The mixture is partitioned between ethyl acetate and aqueous ammonium chloride solution, the organic phase is washed with water, dried over magnesium sulfate and evaporated to dryness in vacuo. The crude product is purified by preparative RP-HPLC with a water/acetonitrile gradient.

Yield: 28 mg (19% of th.)

$^1$H-NMR (300 MHz, DMSO-$d_6$): Δ=2.02 (s, 3H), 4.70 (d, 2H), 5.25 (d, 1H), 5.27 (d, 1H), 5.95 (ddt, 1H), 6.59 (s, 1H), 7.47-7.61 (m, 3H), 7.63-7.91 (m, 7H), 7.95 (d, 2H) ppm.

Example 78

Allyl 3-[N-(tert.-butoxycarbonyl)glycyl]-4-(4-cyanophenyl)-6-methyl-2-oxo-1-[3-(trifluoromethyl)-phenyl]-1,2,3,4-tetrahydropyrimidine-5-carboxylate

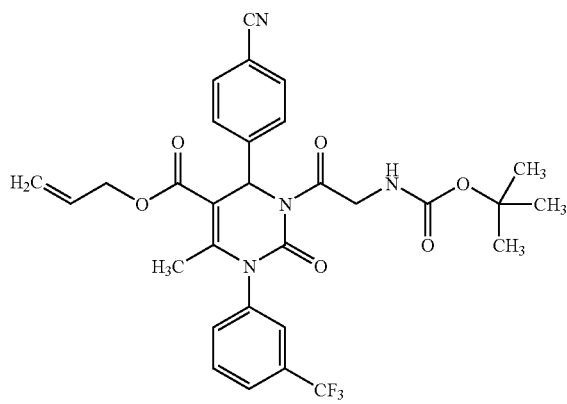 [SMILES: C=CCOC(=O)C1=C(C)N(c2cccc(C(F)(F)F)c2)C(=O)N(C(=O)CNC(=O)OC(C)(C)C)C1c1ccc(C#N)cc1]

Reagent A: 71.4 mg (0.41 mmol) N-tert.-butoxycarbonylglycine and 41.2 mg (0.41 mmol) N-methylmorpholine are dissolved in 1 ml dry 1,2-dimethoxyethane. 55.9 mg (0.41 mmol) isobutyl chloroformate are added, the reaction mixture is stirred for 5 min, then filtered and the residue washed once with 1,2-dimethoxyethane. The combined filtrates are used as Reagent A in the following reaction.

150 mg (0.34 mmol) of Example 5A are dissolved in 2 ml dry tetrahydrofuran and cooled to 0° C. 14.2 mg (0.36 mmol) sodium hydride are added, the mixture is warmed to room temperature, and stirring is continued for 30 min. Reagent A (vide supra) is added, and reaction is continued at room temperature overnight. The reaction mixture is partitioned between ethyl acetate and water, the organic extract is dried over magnesium sulfate and evaporated to dryness in vacuo. The crude product is purified by sequential column chromatography over silica gel (eluent: cyclohexane/ethyl acetate 3:1) and preparative RP-HPLC with a water/acetonitrile gradient.

Yield: 120 mg (19% of th.)

$^1$H-NMR (300 MHz, DMSO-$d_6$): Δ=1.40 (s, 9H), 2.11 (s, 3H), 4.20 (dd, 1H), 4.32 (dd, 1H), 4.70 (d, 2H), 5.18-5.28 (m, 2H), 5.92 (ddt, 1H), 6.69 (s, 1H), 7.09 (t, 1H), 7.48 (br. s, 1H), 7.55 (d, 2H), 7.65-7.80 (m, 2H), 7.83 (d, 1H), 7.90 (d, 2H) ppm.

Example 79

5-Allyl 1-[2-(benzyloxy)-2-oxoethyl]6-(4-cyanophenyl)-4-methyl-2-oxo-3-[3-(trifluoromethyl)-phenyl]-3,6-dihydropyrimidine-1,5(2R)-dicarboxylate

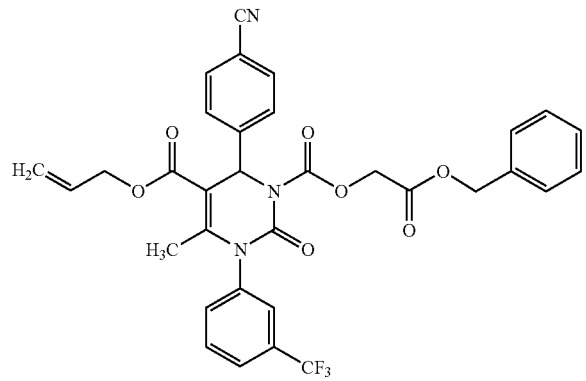 [SMILES: C=CCOC(=O)C1=C(C)N(c2cccc(C(F)(F)F)c2)C(=O)N(C(=O)OCC(=O)OCc2ccccc2)C1c1ccc(C#N)cc1]

Reagent B: 150 mg (0.90 mmol) benzyl 2-hydroxyacetate and 142 mg (1.81 mmol) pyridine are dissolved in 1 ml dichloromethane at 0° C. 191 mg (0.95 mmol) 4-nitrophenyl chloroformate is added, the reaction solution is warmed to room temperature, and stirring is continued for 1 hour. The reaction mixture is partitioned between dichloromethane and 2 N hydrochloric acid, the organic layer is washed sequentially with water and saturated aq. sodium chloride solution, dried over magnesium sulfate and evaporated to dryness in vacuo. The residue is used as Reagent B in the following reaction.

200 mg (0.45 mmol) of Example 5A are dissolved in 2 ml dry tetrahydrofuran. 19 mg (0.48 mmol) sodium hydride are added at 0° C., the reaction mixture is warmed to room temperature, and stirring is continued for 30 min. Reagent B (vide supra) is added as a solution in 1 ml tetrahydrofuran, and reaction is continued at room temperature overnight. The reaction mixture is partitioned between ethyl acetate and 2 N hydrochloric acid, the organic layer is washed with water, dried over magnesium sulfate, and evaporated to dryness in vacuo. The crude product is purified by sequential column chromatography over silica gel (eluent: cyclohexane/ethyl acetate 3:1) and preparative RP-HPLC with a water/acetonitrile gradient.

Yield: 139 mg (48% of th.)

$^1$H-NMR (400 MHz, DMSO-$d_6$): Δ=2.10 (s, 3H), 4.65-4.78 (m, 2H), 4.98 (s, 2H), 5.16-5.28 (m, 4H), 5.93 (ddt, 1H), 6.45 (s, 1H), 7.31-7.42 (m, 6H), 7.56-7.65 (m, 3H), 7.70 (t, 1H), 7.82 (d, 1H), 7.90 (d, 2H) ppm.

In analogy to the procedure for Example 79, the following compound is prepared:

| Example No. | Structure | Starting material | Yield [%] | $R_t$ [min] (method) | Mass $[M + H]^+$ |
|---|---|---|---|---|---|
| 80 | 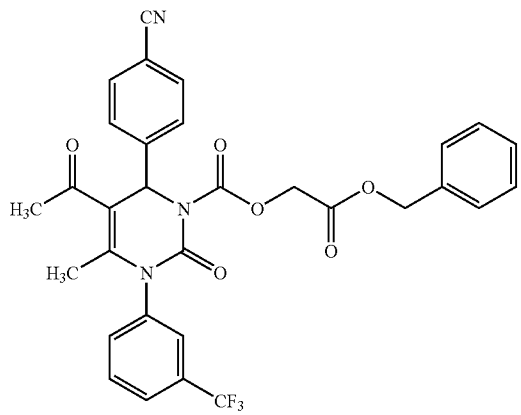 [SMILES: CC(=O)C1=C(C)N(c2cccc(C(F)(F)F)c2)C(=O)N(C(=O)OCC(=O)OCc2ccccc2)C1c1ccc(C#N)cc1] | Example 7A | 56 | 5.22 (2) | 592 |

Example 81

4-{5-Acetyl-3-allyl-6-methyl-2-oxo-1-[3-(trifluoromethyl)phenyl]-1,2,3,4-tetrahydropyrimidin-4-yl}benzonitrile

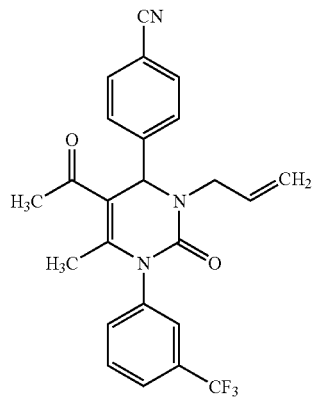 [SMILES: C=CCN1C(=O)N(c2cccc(C(F)(F)F)c2)C(C)=C(C(C)=O)C1c1ccc(C#N)cc1]

100 mg (0.25 mmol) of Example 7A are dissolved in 2 ml dimethylformamide, and 45 mg (0.38 mmol) allylbromide and 115 mg (0.50 mmol) potassium carbonate are added. The reaction mixture is stirred at room temperature overnight, and then the product is purified by preparative RP-HPLC with a water/acetonitrile gradient.

Yield: 67 mg (61% of th.)

$^1$H-NMR (300 MHz, DMSO-$d_6$): Δ=1.9 (s, 3H), 2.3 (s, 3H), 3.5 (m, 1H), 4.3 (m, 1H), 5.1 (dd, 1H), 5.2 (dd, 1H), 5.6 (s, 1H), 5.6 (m, 1H), 7.6 (m, 3H), 7.7 (m, 2H), 7.8 (m, 1H), 7.9 (m, 2H) ppm.

Example 82 tert.-Butyl {2-[5-acetyl-6-(4-cyanophenyl)-4-methyl-2-oxo-3-[3-(trifluoromethyl)phenyl-]3,6-di-hydropyrimidin-1(2H)-yl]ethyl} carbamate

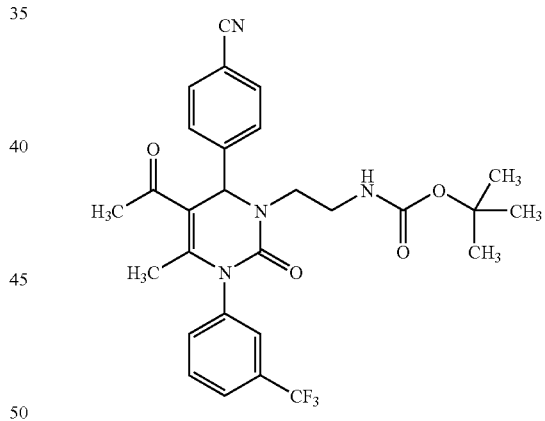

1.82 g (4.57 mmol) of Example 7A are dissolved in 40 ml tetrahydrofuran and 274 mg (6.85 mmol) sodium hydride (60% dispersion in mineral oil) are added. The reaction mixture is stirred at room temperature for 30 minutes, then 1.64 g (6.85 mmol) of Example 32A are added. After stirring at room temperature overnight, water is added, the mixture is evaporated to dryness in vacuo and the product is purified by column chromatography (silica, eluent: dichloromethane/methanol Yield: 137 mg (6% of th.)

$^1$H-NMR (400 MHz, DMSO-$d_6$): Δ=1.4 (s, 9H), 1.9 (s, 3H), 2.3 (s, 3H), 2.9 (m, 1H), 3.1 (m, 1H), 3.2 (m, 1H), 3.6 (m, 1H), 5.6 (s, 1H), 6.9 (br t, 1H), 7.6 (m, 3H), 7.6 (m, 1H), 7.7 (m, 1H), 7.8 (m, 1H), 7.9 (m, 2H) ppm.

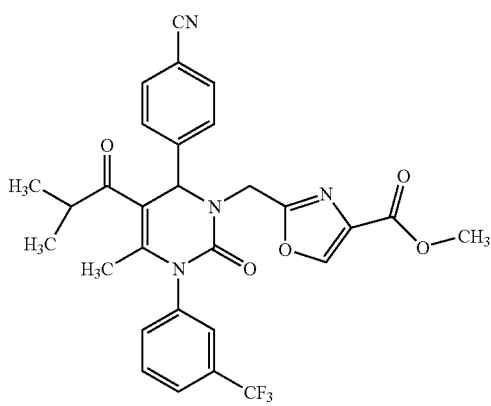 [SMILES: COC(=O)c1coc(CN2C(=O)N(c3cccc(C(F)(F)F)c3)C(C)=C(C(=O)C(C)C)C2c2ccc(C#N)cc2)n1]

Example 83

Methyl 2-{[6-(4-cyanophenyl)-5-isobutyryl-4-methyl-2-oxo-3-[3-(trifluoromethyl)phenyl]-3,6-di-hydropyrimidin-1(2H)-yl]methyl}-1,3-oxazole-4-carboxylate The title compound is prepared from Example 33A according to the procedure described for Example 48.

Yield: 34 mg (28% of th.)

$^1$H-NMR (400 MHz, DMSO-d$_6$): Δ=8.72 (s, 1H), 7.95-7.54 (m, 8H), 5.78 (s, 1H), 4.89 (d, 1H), 4.57 (d, 1H), 3.79 (s, 3H), 3.03 (m, 1H), 1.83 (s, 3H), 0.98-0.78 (m, 6H) ppm.

Example 84

2-[6-(4-Cyanophenyl)-5-isobutyryl-4-methyl-2-oxo-3-[3-(trifluoromethyl)phenyl]-3,6-dihydro-pyrimidin-1(2H)-yl]-N-[(2,2,2-trifluoroethyl)sulfonyl]acetamide

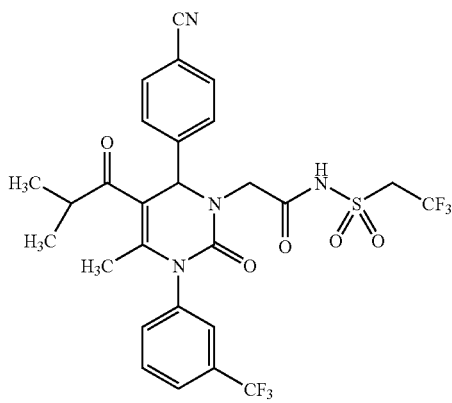 [SMILES: CC1=C(C(=O)C(C)C)C(c2ccc(C#N)cc2)N(CC(=O)NS(=O)(=O)CC(F)(F)F)C(=O)N1c1cccc(C(F)(F)F)c1]

The title compound is prepared from Example 35A according to the procedure described for Example 46.

Yield: 43 mg (36% of th.)

$^1$H-NMR (400 MHz, DMSO-d$_6$): Δ=7.95-7.54 (m, 9H), 5.68 (s, 1H), 4.69-4.48 (m, 2H), 4.34-3.77 (m, 2H), 3.00 (m, 1H), 1.84 (s, 3H), 0.94 (d, 3H), 0.84 (d, 3H) ppm.

Example 85

2-{[6-(4-Cyanophenyl)-5-isobutyryl-4-methyl-2-oxo-3-[3-(trifluoromethyl)phenyl]-3,6-dihydro-pyrimidin-1(2H)-yl]methyl}-1,3-oxazole-4-carboxylic acid

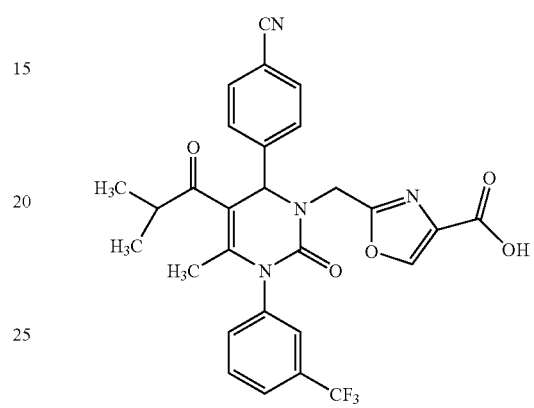

The title compound is prepared from Example 83 according to the procedure described for Example 52.

Yield: 23 mg (86% of th.)

$^1$H-NMR (300 MHz, DMSO-d$_6$): Δ=12.8 (s, 1H), 8.54 (s, 1H), 7.91-7.52 (m, 8H), 5.76 (s, 1H), 4.91 (d, 1H), 4.48 (d, 1H), 3.03 (m, 1H), 1.83 (s, 3H), 0.92-0.78 (m, 6H) ppm.

C. Operative Examples Relating to Pharmaceutical Compositions

The compounds according to the invention can be converted into pharmaceutical preparations as follows:

Tablet
Composition:

100 mg of the compound of Example 1, 50 mg of lactose (monohydrate), 50 mg of maize starch (native), 10 mg of polyvinylpyrrolidone (PVP 25) (from BASF, Ludwigshafen, Germany) and 2 mg of magnesium stearate.

Tablet weight 212 mg, diameter 8 mm, curvature radius 12 mm.

Preparation:

The mixture of active component, lactose and starch is granulated with a 5% solution (m/m) of the PVP in water. After drying, the granules are mixed with magnesium stearate for 5 min. This mixture is moulded using a customary tablet press (tablet format, see above). The moulding force applied is typically 15 kN.

Orally Administrable Suspension
Composition:

1000 mg of the compound of Example 1, 1000 mg of ethanol (96%), 400 mg of Rhodigel (xanthan gum from FMC, Pennsylvania, USA) and 99 g of water.

A single dose of 100 mg of the compound according to the invention is provided by 10 ml of oral suspension.

Preparation:

The Rhodigel is suspended in ethanol and the active component is added to the suspension. The water is added with stirring. Stirring is continued for about 6 h until the swelling of the Rhodigel is complete.

We claim:

1. A compound of formula (I)

$$\text{(I)}$$

[chemical structure showing ring A with substituents R$^1$, R$^2$, bonded to a 6-membered ring with R$^4$, R$^5$, R$^6$ substituents, N, carbonyl, and a second ring with Y$^1$, Y$^2$, Y$^3$, Y$^4$, Y$^5$, R$^3$, R$^7$]

wherein

A represents heteroaryl ring,

R$^1$, R$^2$ and R$^3$ independently from each other represent hydrogen, halogen, nitro, cyano, C$_1$-C$_6$-alkyl, hydroxy or C$_1$-C$_6$-alkoxy, wherein C$_1$-C$_6$-alkyl and C$_1$-C$_6$-alkoxy can be further substituted with one to three identical or different radicals selected from the group consisting of halogen, hydroxy and C$_1$-C$_4$-alkoxy, R$^4$ represents trifluoromethylcarbonyl, C$_1$-C$_6$-alkylcarbonyl, C$_1$-C$_6$-alkoxycarbonyl, C$_2$-C$_6$-alkenoxycarbonyl, hydroxycarbonyl, aminocarbonyl, mono- or di-C$_1$-C$_4$-alkylamino-carbonyl, C$_6$-C$_{10}$-arylaminocarbonyl, arylcarbonyl, heteroarylcarbonyl, heterocyclylcarbonyl, heteroaryl, heterocyclyl or cyano, wherein C$_1$-C$_6$-alkylcarbonyl, C$_1$-C$_6$-alkoxy-carbonyl, mono- and di-C$_1$-C$_4$-alkylaminocarbonyl can be further substituted with one to three identical or different radicals selected from the group consisting of C$_3$-C$_8$-cycloalkyl, hydroxy, C$_1$-C$_4$-alkoxy, C$_1$-C$_4$-alkoxycarbonyl, hydroxycarbonyl, aminocarbonyl, mono- and di-C$_1$-C$_4$-alkylaminocarbonyl, C$_1$-C$_4$-alkylcarbonylamino, N—(C$_1$-C$_4$-alkylcarbonyl)-N—(C$_1$-C$_4$-alkyl)amino, cyano, amino, mono- and di-C$_1$-C$_4$-alkylamino, heteroaryl, heterocyclyl and tri-(C$_1$-C$_6$-alkyl)-silyl, and wherein heteroarylcarbonyl, heterocyclylcarbonyl, heteroaryl and heterocyclyl can be further substituted with C$_1$-C$_4$-alkyl, R$^5$ represents C$_1$-C$_4$-alkyl, which can be substituted with one to three identical or different radicals selected from the group consisting of halogen, hydroxy, C$_1$-C$_6$-alkoxy, C$_2$-C$_6$-alkenoxy, C$_1$-C$_6$-alkylthio, amino, mono- and di-C$_1$-C$_6$-alkylamino, arylamino, hydroxycarbonyl, C$_1$-C$_6$-alkoxycarbonyl and the radical —O—C$_1$-C$_4$-alkyl-O—C$_1$-C$_4$-alkyl, or R$^5$ represents amino, R$^6$ represents a group of the formula -T-U wherein T represents a C$_1$-C$_6$-alkanediyl or C$_2$-C$_6$-alkenediyl group and U represents C$_6$-C$_{10}$-aryl or 5- or 6-membered heteroaryl each of which is substituted by one, two or three radicals independently selected from the group consisting of halogen, C$_1$-C$_6$-alkyl, 5- or 6-membered heteroaryl and a group of the formula —V—W wherein V represents a bond or a C$_1$-C$_6$-alkanediyl or C$_2$-C$_6$-alkenediyl group both of which can be further substituted by C$_3$-C$_8$-cycloalkyl, and W represents C$_1$-C$_6$-alkoxycarbonyl or hydroxycarbonyl, a group of the formula —C(=O)—NR$^a$—SO$_2$—R$^b$ wherein R$^a$ represents hydrogen or C$_1$-C$_6$-alkyl, and R$^b$ represents C$_1$-C$_6$-alkyl which can be substituted by trifluoromethyl, or R$^b$ represents C$_6$-C$_{10}$-aryl which can be substituted by C$_1$-C$_6$-alkyl, halogen, cyano, nitro or trifluoromethyl, a group of the formula —C(=O)—NR$^c$R$^d$ wherein R$^c$ represents hydrogen or C$_1$-C$_6$-alkyl, and R$^d$ represents C$_6$-C$_{10}$-aryl which can be substituted by C$_1$-C$_6$-alkoxycarbonyl or hydroxycarbonyl, a group of the formula —C(=O)—NR$^e$—OR$^f$ wherein R$^e$ and R$^f$ independently from each other represent hydrogen or C$_1$-C$_6$-alkyl, or C$_6$-C$_{10}$-arylalkoxy which, in the aryl part, can be substituted by halogen, C$_1$-C$_6$-alkyl, C$_1$-C$_6$-alkoxycarbonyl or hydroxycarbonyl, or R$^6$ represents C$_3$-C$_8$-cycloalkyl which can be substituted by up to three radicals independently selected from the group consisting of C$_1$-C$_6$-alkyl, hydroxy, oxo, C$_1$-C$_6$-alkoxycarbonyl and hydroxycarbonyl, C$_2$-C$_6$-alkenyl which can be substituted by C$_1$-C$_6$-alkoxycarbonyl or hydroxycarbonyl, C$_1$-C$_6$-alkyl or C$_1$-C$_6$-alkylcarbonyl which are substituted by C$_1$-C$_6$-alkoxycarbonylamino, C$_1$-C$_6$-alkoxycarbonyl which is substituted by phenyl-C$_1$-C$_6$-alkoxycarbonyl which for its part, in the phenyl moiety, can be further substituted by halogen, C$_1$-C$_6$-alkyl, C$_1$-C$_6$-alkoxycarbonyl or hydroxycarbonyl, or a group of the formula —SO$_2$—R$^g$ wherein R$^g$ represents C$_1$-C$_6$-alkyl which can be substituted by trifluoromethyl, or R$^g$ represents C$_6$-C$_{10}$-aryl which can be substituted by C$_1$-C$_6$-alkyl, halogen, cyano, nitro, trifluoromethyl, C$_1$-C$_6$-alkoxycarbonyl or hydroxycarbonyl, R$^7$ represents halogen, nitro, cyano, C$_1$-C$_6$-alkyl, hydroxy or C$_1$-C$_6$-alkoxy, wherein C$_1$-C$_6$-alkyl and C$_1$-C$_6$-alkoxy can be further substituted with one to three identical or different radicals selected from the group consisting of halogen, hydroxy and C$_1$-C$_4$-alkoxy, and Y$^1$, Y$^2$, Y$^3$, Y$^4$ and Y$^5$ independently from each other represent CH or N, wherein the ring contains either 0, 1 or 2 nitrogen atoms, and salts thereof.

2. The compound of formula (I) according to claim 1, wherein

A represents heteroaryl ring,

R$^1$, R$^2$ and R$^3$ independently from each other represent hydrogen, halogen, nitro, cyano, C$_1$-C$_6$-alkyl, hydroxy or C$_1$-C$_6$-alkoxy, wherein C$_1$-C$_6$-alkyl and C$_1$-C$_6$-alkoxy can be further substituted with one to three identical or different radicals selected from the group consisting of halogen, hydroxy and C$_1$-C$_4$-alkoxy, R$^4$ represents C$_1$-C$_6$-alkylcarbonyl, C$_1$-C$_6$-alkoxycarbonyl, C$_2$-C$_6$-alkenoxycarbonyl, hydroxy-carbonyl, aminocarbonyl, mono- or di-C$_1$-C$_4$-alkylaminocarbonyl, $C_6$-$C_{10}$-arylaminocarbonyl, heteroarylcarbonyl, heterocyclylcarbonyl, heteroaryl, heterocyclyl or cyano, wherein $C_1$-$C_6$-alkylcarbonyl, $C_1$-$C_6$-alkoxycarbonyl, mono- and di-$C_1$-$C_4$-alkylaminocarbonyl can be further substituted with one to three identical or different radicals selected from the group consisting of $C_3$-$C_8$-cycloalkyl, hydroxy, $C_1$-$C_4$-alkoxy, $C_1$-$C_4$-alkoxycarbonyl, hydroxycarbonyl, aminocarbonyl, mono- and di-$C_1$-$C_4$-alkylaminocarbonyl, $C_1$-$C_4$-alkylcarbonylamino, amino, mono- and di-$C_1$-$C_4$-alkylamino, heteroaryl, heterocyclyl and tri-($C_1$-$C_6$-alkyl)-silyl, $R^5$ represents $C_1$-$C_4$-alkyl, which can be substituted with one to three identical or different radicals selected from the group consisting of halogen, hydroxy, $C_1$-$C_6$-alkoxy, $C_2$-$C_6$-alkenoxy, $C_1$-$C_6$-alkylthio, amino, mono- and di-$C_1$-$C_6$-alkylamino, arylamino, hydroxycarbonyl, $C_1$-$C_6$-alkoxycarbonyl and the radical —O—$C_1$-$C_4$-alkyl-O—$C_1$-$C_4$-alkyl, $R^6$ represents
  a group of the formula -T-U wherein
    T represents a $C_1$-$C_4$-alkanediyl or $C_2$-$C_4$-alkenediyl group
    and
    U represents
      $C_6$-$C_{10}$-aryl or 5- or 6-membered heteroaryl each of which is substituted by one, two or three radicals independently selected from the group consisting of halogen, $C_1$-$C_6$-alkyl, 5- or 6-membered heteroaryl and a group of the formula —V—W wherein V represents a bond, a $C_2$-$C_6$-alkenediyl group or a $C_1$-$C_6$-alkanediyl group the latter of which can be further substituted by $C_3$-$C_8$-cycloalkyl, and W represents $C_1$-$C_6$-alkoxy-carbonyl or hydroxycarbonyl,
      a group of the formula —C(=O)—NH—SO$_2$—$R^b$ wherein $R^b$ represents $C_1$-$C_6$-alkyl which can be substituted by trifluoromethyl, or $R^b$ represents $C_6$-$C_{10}$-aryl which can be substituted by $C_1$-$C_6$-alkyl, halogen, cyano, nitro or trifluoromethyl,
      or
      a group of the formula —C(=O)NHR$^d$ wherein R$^d$ represents $C_6$-$C_{10}$-aryl which can be substituted by $C_1$-$C_6$-alkoxycarbonyl or hydroxycarbonyl,
  or
$R^6$ represents
  $C_3$-$C_8$-cycloalkyl which can be substituted by up to three radicals independently selected from the group consisting of $C_1$-$C_6$-alkyl, hydroxy, oxo, $C_1$-$C_6$-alkoxycarbonyl and hydroxycarbonyl,
  or
  $C_2$-$C_6$-alkenyl which can be substituted by $C_1$-$C_6$-alkoxycarbonyl or hydroxyl-carbonyl, $R^7$ represents halogen, nitro, cyano, $C_1$-$C_6$-alkyl, hydroxy or $C_1$-$C_6$-alkoxy, wherein $C_1$-$C_6$-alkyl and $C_1$-$C_6$-alkoxy can be further substituted with one to three identical or different radicals selected from the group consisting of halogen, hydroxy and $C_1$-$C_4$-alkoxy,
and
$Y^1, Y^2, Y^3, Y^4$ and $Y^5$ independently from each other represent CH or N, wherein the ring contains either 0, 1 or 2 nitrogen atoms.

3. The compound of formula (I) according to claim 1, wherein
A represents a pyridyl ring,
$R^1$, $R^2$ and $R^3$ independently from each other represent hydrogen, fluoro, chloro, bromo, nitro, cyano, methyl, ethyl, trifluoromethyl or trifluoromethoxy, $R^4$ represents $C_1$-$C_6$-alkylcarbonyl, $C_1$-$C_6$-alkoxycarbonyl, allyloxycarbonyl, hydroxycarbonyl, aminocarbonyl, mono-$C_1$-$C_4$-alkylaminocarbonyl, furylcarbonyl, pyridylcarbonyl or cyano, wherein $C_1$-$C_6$-alkylcarbonyl, $C_1$-$C_6$-alkoxycarbonyl and mono-$C_1$-$C_4$-alkylaminocarbonyl can be substituted with one to three identical or different radicals selected from the group consisting of $C_3$-$C_6$-cycloalkyl, hydroxy, $C_1$-$C_4$-alkoxy, $C_1$-$C_4$-alkoxycarbonyl, hydroxy-carbonyl, amino, mono- and di-$C_1$-$C_4$-alkylamino, $R^5$ represents methyl or ethyl,
$R^6$ represents
  a group of the formula -T-U wherein
    T represents a $C_1$-$C_4$-alkanediyl group
    and
    U represents
      phenyl, furyl, thienyl, oxazolyl, thiazolyl or pyridyl each of which is substituted by one or two radicals independently selected from the group consisting of fluoro, chloro, bromo, $C_1$-$C_4$-alkyl, thienyl, pyridyl and a group of the formula —V—W wherein V represents a bond or a $C_1$-$C_4$-alkanediyl or $C_2$-$C_4$-alkenediyl group, and W represents $C_1$-$C_4$-alkoxy-carbonyl or hydroxycarbonyl,
      a group of the formula —C(=O)—NH—SO$_2$—$R^b$ wherein $R^b$ represents $C_1$-$C_4$-alkyl which can be substituted by trifluoromethyl, or $R^b$ represents phenyl which can be substituted by $C_1$-$C_4$-alkyl, fluoro, chloro, bromo, cyano, nitro or trifluoromethyl,
      or
      a group of the formula —C(=O)—NHR$^d$ wherein R$^d$ represents phenyl which can be substituted by $C_1$-$C_4$-alkoxycarbonyl or hydroxycarbonyl,
  or
$R^6$ represents
  $C_3$-$C_6$-cycloalkyl which can be substituted by up to two radicals independently selected from the group consisting of $C_1$-$C_4$-alkyl; hydroxy, oxo, $C_1$-$C_4$-alkoxycarbonyl and hydroxycarbonyl,
  or
  $C_2$-$C_4$-alkenyl which is substituted by $C_1$-$C_4$-alkoxycarbonyl or hydroxycarbonyl, $R^7$ represents halogen, nitro, cyano, trifluoromethyl, trifluoromethoxy, methyl or ethyl,
and
$Y^1, Y^2, Y^3, Y^4$ and $Y^1$ each represent CH.

4. The compound of formula (I) according to claim 1, wherein
A represents a pyridyl ring,
$R^1$ and $R^3$ each represent hydrogen,
$R^2$ represents fluoro, chloro, bromo, nitro or cyano,
$R^4$ represents cyano, hydroxycarbonyl, furylcarbonyl, pyridylcarbonyl, $C_1$-$C_4$-alkylcarbonyl or $C_1$-$C_4$-alkoxycarbonyl, wherein $C_1$-$C_4$-alkylcarbonyl and $C_1$-$C_4$-alkoxycarbonyl can be substituted with a radical selected from the group consisting of hydroxy, $C_1$-$C_4$-alkoxy, $C_1$-$C_4$-alkoxycarbonyl, hydroxycarbonyl, mono- and di-$C_1$-$C_4$-alkylamino,
$R^5$ represents methyl,
$R^6$ represents
  a group of the formula -T-U wherein
    T represents a —CH$_2$— group
    and
    U represents
      phenyl, furyl or oxazolyl each of which is substituted by one or two radicals independently selected from the group consisting of fluoro, chloro, bromo, $C_1$-$C_4$-alkyl and a group of the formula —V—W wherein V represents a bond, a —$CH_2$— group or a —CH=CH— group, and W represents $C_1$-$C_4$-alkoxycarbonyl or hydroxy-carbonyl, a group of the formula —C(=O)—NH—$SO_2$—$R^b$ wherein $R^b$ represents $C_1$-$C_4$-alkyl which can be substituted by trifluoromethyl, or $R^b$ represents phenyl which can be substituted by $C_1$-$C_4$-alkyl, fluoro, chloro, bromo, cyano, nitro or trifluoromethyl, or a group of the formula —C(=O)—$NHR^d$ wherein $R^d$ represents phenyl which can be substituted by $C_1$-$C_4$-alkoxycarbonyl or hydroxycarbonyl, or $R^6$ represents $C_3$-$C_6$-cycloalkyl which can be substituted by up to two radicals independently selected from the group consisting of $C_1$-$C_4$-alkyl, hydroxy, oxo, $C_1$-$C_4$-alkoxycarbonyl and hydroxycarbonyl, or a —CH=CH— group which is substituted by $C_1$-$C_4$-alkoxycarbonyl or hydroxycarbonyl, $R^7$ represents trifluoromethyl or nitro, and $Y^1, Y^2, Y^3, Y^4$ and $Y^1$ each represent CH.

5. The compound of formula (I) according to claim 1, wherein A is pyridyl.

6. The compound of formula (I) according to claim 1, wherein $R^1$ is hydrogen.

7. The compound of formula (I) according to claim 1, wherein $R^2$ is cyano.

8. The compound of formula (I) according to claim 1, wherein $R^3$ is hydrogen.

9. The compound of formula (I) according to claim 1, wherein $R^4$ is $C_1$-$C_4$-alkoxycarbonyl optionally substituted by hydroxy, or wherein $R^4$ is $C_1$-$C_4$-alkylcarbonyl, hydroxycarbonyl or cyano.

10. The compound of formula (I) according to claim 1, wherein $R^5$ is methyl.

11. The compound of formula (I) according to claim 1, wherein $R^7$ is trifluoromethyl or nitro.

12. A compound of formula (IA)

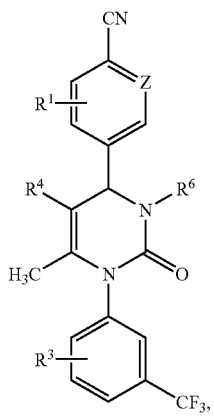

(IA)

wherein

Z represents N, and $R^1$ and $R^3$ independently from each other represent hydrogen, halogen, nitro, cyano, $C_1$-$C_6$-alkyl, hydroxy or $C_1$-$C_6$-alkoxy, wherein $C_1$-$C_6$-alkyl and $C_1$-$C_6$-alkoxy can be further substituted with one to three identical or different radicals selected from the group consisting of halogen hydroxy and $C_1$-$C_4$-alkoxy, $R^4$ represents trifluoromethylcarbonyl, $C_1$-$C_6$-alkoxycarbonyl, $C_1$-$C_6$-alkoxycarbonyl, $C_2$-$C_6$-alkenoxycarbonyl, hydroxycaxbonyl aminocarbonyl, mono- or di-$C_1$-$C_4$-alkylaminocarbonyl $C_6$-$C_{10}$-arylaminocaxbonyl, arylcarbonyl, heteroarylcarbonyl, heterocyclylcarbonyl, heteroaryl, heterocyclyl or cyano, wherein $C_1$-$C_6$-alkylcarbonyl, $C_1$-$C_6$-alkoxy-carbonyl, mono- and di-$C_1$-$C_4$-alkylaminocarbonyl can be further substituted with one to three identical or different radicals selected from the group consisting of $C_3$-$C_8$-cycloalkyl, hydroxy, $C_1$-$C_4$-alkoxy, $C_1$-$C_4$-alkoxycarbonyl, hydroxycarbonyl, aminocarbonyl, mono- and di-$C_1$-$C_4$-alkylaminocarbonyl, $C_1$-$C_4$-alkylcarbonylamino, N—($C_1$-$C_4$-alkylcarbonyl)-N—($C_1$-$C_4$-alkyl)amino, cyano amino, mono- and di-$C_1$-$C_4$-alkylamino heteroaryl, heterocyclyl and tri-($C_1$-$C_6$-alkyl)-silyl, and wherein heteroarylcarbonyl, heterocyclylcarbonyl, heteroaryl and heterocyclyl can be further substituted with $C_1$-$C_4$-alkyl, $R^6$ represents a group of the formula -T-U wherein T represents a $C_1$-$C_6$-alkanediyl or $C_2$-$C_6$-alkenediyl group and U represents $C_6$-$C_{10}$-aryl or 5- or 6-membered heteroaryl each of which is substituted by one, two or three radicals independently selected from the group consisting of halogen $C_1$-$C_6$-alkyl, 5- or 6-membered heteroaryl and a group of the formula —V—W wherein V represents a bond or a $C_1$-$C_6$-alkanediyl or $C_2$-$C_6$-alkenediyl group both of which can be further substituted by $C_3$-$C_8$-cycloalkyl, and W represents $C_1$-$C_6$-alkoxycarbonyl or hydroxycarbonyl, a group of the formula —C(=O)—$NR^a$—$SO_2$—$R^b$ wherein $R^a$ represents hydrogen or $C_1$-$C_6$-alkyl, and $R^b$ represents $C_1$-$C_6$-alkyl which can be substituted b trifluoromethyl, or $R^b$ represents $C_6$-$C_{10}$-aryl which can be substituted b $C_1$-$C_6$-alkyl, halogen, cyano, nitro or trifluoromethyl, a group of the formula —C(=O)—$NR^cR^d$ wherein $R^c$ represents hydrogen or $C_1$-$C_6$-alkyl, and $R^d$ represents $C_6$-$C_{10}$-aryl which can be substituted by $C_1$-$C_6$-alkoxycarbonyl or hydroxycarbonyl, a group of the formula —C(=O)—$NR^e$—$OR^f$ wherein $R^e$ and $R^f$ independently from each other represent hydrogen or $C_1$-$C_6$-alkyl, or $C_6$-$C_{10}$-arylalkoxy which, in the aryl part can be substituted by halogen, $C_1$-$C_6$-alkyl, $C_1$-$C_6$-alkoxycarbonyl or hydroxycarbonyl, or $R^6$ represents $C_3$-$C_8$-cycloalkyl which can be substituted by up to three radicals independently selected from the group consisting of $C_1$-$C_6$-alkyl, hydroxy, oxo, $C_1$-$C_6$-alkoxycarbonyl and hydroxycarbonyl, $C_2$-$C_6$-alkenyl which can be substituted b $C_1$-$C_6$-alkoxycarbonyl or hydroxycarbonyl, $C_1$-$C_6$-alkyl or $C_1$-$C_6$-alkylcarbonyl which are substituted by $C_1$-$C_6$alkoxycarbonylamino, $C_1$-$C_6$-alkoxycarbonyl which is substituted by phenyl-$C_1$-$C_6$-alkoxycarbonyl which for its part in the phenyl moiety, can be further substituted by halogen, $C_1$-$C_6$-alkyl, $C_1$-$C_6$-alkoxycarbonyl or hydroxycarbonyl, or a group of the formula —$SO_2$—$R^g$ wherein $R^g$ represents $C_1$-$C_6$-alkyl which can be substituted b trifluoromethyl or $R^g$ represents $C_6$-$C_{10}$-aryl which can be substituted by $C_1$-$C_6$-alkyl, halogen, cyano, nitro, trifluoromethyl, $C_1$-$C_6$-alkoxycarbonyl or hydroxycarbonyl.

13. A process for synthesizing a compound of formula (I)

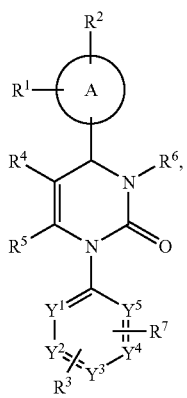

(I)

wherein

A represents an aryl or heteroaryl ring, $R^1$, $R^2$ and $R^3$ independently from each other represent hydrogen, halogen, nitro, cyano, $C_1$-$C_6$-alkyl, hydroxy or $C_1$-$C_6$-alkoxy, wherein $C_1$-$C_6$-alkyl and $C_1$-$C_6$-alkoxy can be further substituted with one to three identical or different radicals selected from the group consisting of halogen, hydroxy and $C_1$-$C_4$-alkoxy, $R^4$ represents trifluoromethylcarbonyl, $C_1$-$C_6$-alkylcarbonyl, $C_1$-$C_6$-aralkoxycarbonyl, $C_2$-$C_6$-alkenoxycarbonyl, hydroxycaxbonyl, aminocarbonyl, mono- or di-$C_1$-$C_4$-alkylaminocarbonyl, $C_6$-$C_{10}$-arylaminocaxbonyl, arylcarbonyl, heteroarylcarbonyl, heterocyclylcarbonyl, heteroaryl, heterocyclyl or cyano, wherein $C_1$-$C_6$-alkylcarbonyl, $C_1$-$C_6$-alkoxycarbon mono- and di-$C_1$-$C_4$-alkylaminocarbonyl can be further substituted with one to three identical or different radicals selected from the group consisting of $C_3$-$C_8$-cycloalkyl, hydroxy, $C_1$-$C_4$-alkoxy, $C_1$-$C_4$-alkoxycarbonyl, hydroxycarbonyl, aminocarbonyl, mono- and di-$C_1$-$C_4$-alkylaminocarbonyl, $C_1$-$C_4$-alkylcarbonylamino, N—($C_1$-$C_4$-alkylcarbonyl)-N—($C_1$-$C_4$-alkyl)amino cyano, amino, mono- and di-$C_1$-$C_4$-alkylamino heteroaryl, heterocyclyl and tri-($C_1$-$C_6$-alkyl)-silyl and wherein heteroarylcarbonyl, heterocyclylcarbonyl, heteroaryl and heterocyclyl can be further substituted with $C_1$-$C_4$-alkyl, $R^5$ represents $C_1$-$C_4$-alkyl, which can be substituted with one to three identical or different radicals selected from the group consisting of halogen, hydroxy, $C_1$-$C_6$-alkoxy, $C_2$-$C_6$-alkenoxy, $C_1$-$C_6$-alkylthio, amino, mono- and di-$C_1$-$C_6$-alkylamino, arylamino hydroxycarbonyl, $C_1$-$C_6$-alkoxycarbonyl and the radical —O—$C_1$-$C_4$-alkyl-O—$C_1$-$C_4$-alkyl, or $R^5$ represents amino, $R^6$ represents a group of the formula -T-U wherein T represents a $C_1$-$C_6$-alkanediyl or $C_2$-$C_6$-alkenediyl group and U represents $C_6$-$C_{10}$-aryl or 5- or 6-membered heteroaryl each of which is substituted by one, two or three radicals independently selected from the group consisting of halogen $C_1$-$C_6$-alkyl, 5- or 6-membered heteroaryl and a group of the formula —V—W wherein V represents a bond or a $C_1$-$C_6$-alkanediyl or $C_2$-$C_6$-alkenediyl group both of which can be further substituted b $C_3$-$C_8$-cycloalkyl, and W represents $C_1$-$C_6$-alkoxycarbonyl or hydroxycarbonyl, a group of the formula —C(=O)—$NR^a$—$SO_2$—$R^b$ wherein $R^a$ represents hydrogen or $C_1$-$C_6$-alkyl, and $R^b$ represents $C_1$-$C_6$-alkyl which can be substituted by trifluoromethyl or $R^b$ represents $C_6$-$C_{10}$-aryl which can be substituted b $C_1$-$C_6$-alkyl, halogen, cyano, nitro or trifluoromethyl, a group of the formula —C(=O)—$NR^cR^d$ wherein $R^c$ represents hydrogen or $C_1$-$C_6$-alkyl, and $R^d$ represents $C_6$-$C_{10}$-aryl which can be substituted by $C_1$-$C_6$-alkoxycarbonyl or hydroxycarbonyl, a group of the formula —C(=O)—$NR^e$—$OR^f$ wherein $R^e$ and $R^f$ independently from each other represent hydrogen or $C_1$-$C_6$-alkyl, or $C_6$-$C_{10}$-arylalkoxy which, in the aryl part, can be substituted by halogen, $C_1$-$C_6$-alkyl, $C_1$-$C_6$-alkoxycarbonyl or hydroxycarbonyl, or $R^6$ represents $C_3$-$C_8$-cycloalkyl which can be substituted by up to three radicals independently selected from the group consisting of $C_1$-$C_6$-alkyl, hydroxy, oxo, $C_1$-$C_6$-alkoxycarbonyl and hydroxycarbonyl, $C_2$-$C_6$-alkenyl which can be substituted by $C_1$-$C_6$-alkoxycarbonyl or hydroxycarbonyl, $C_1$-$C_6$-alkyl or $C_1$-$C_6$-alkylcarbonyl which are substituted by $C_1$-$C_6$-alkoxycarbonylamino, $C_1$-$C_6$-alkoxycarbonyl which is substituted by phenyl-$C_1$-$C_6$-alkoxycarbonyl which for its part, in the phenyl moiety, can be further substituted by halogen $C_1$-$C_6$-alkyl, $C_1$-$C_6$-alkoxycarbonyl or hydroxycarbonyl, or a group of the formula —$SO_2$—$R^g$ wherein $R^g$ represents $C_1$-$C_6$-alkyl which can be substituted b trifluoromethyl, or $R^g$ represents $C_6$-$C_{10}$-aryl which can be substituted by $C_1$-$C_6$-alkyl, halogen, cyano, nitro, trifluoromethyl, $C_1$-$C_6$-alkoxycarbonyl or hydroxycarbonyl, $R^7$ represent halogen, nitro, cyano, $C_1$-$C_6$-alkyl, hydroxy or $C_1$-$C_6$-alkoxy, wherein $C_1$-$C_6$-alkyl and $C_1$-$C_6$-alkoxy can be further substituted with one to three identical or different radicals selected from the group consisting of halogen hydroxy and $C_1$-$C_4$-alkoxy, and $Y^1, Y^2, Y^3, Y^4$ and $Y^5$ independently from each other represent CH or N, wherein the ring contains either 0, 1 or 2 nitrogen atoms, the process comprising the step of condensing a compound of formula (II)

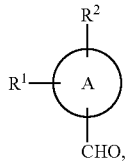
(II)

wherein A, R$^1$ and R$^2$ have the meaning indicated in this claim,
with a compound of formula (III)

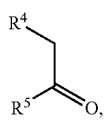
(III)

wherein R$^4$ and R$^5$ have the meaning indicated in this claim,
and a compound of formula (IV)

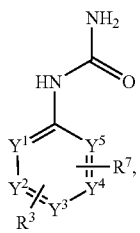
(IV)

wherein R$^3$, R$^7$, and Y$^1$ to Y$^5$ have the meaning indicated in this claim, to give a compound of formula (IB)

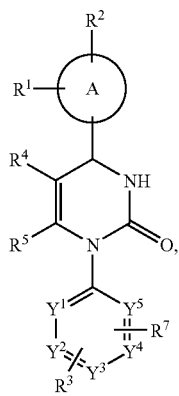
(IB)

wherein A, R$^1$ to R$^5$, R$^7$, and Y$^1$ to Y$^5$ have the meaning indicated in this claim, and reactomg the compound of general (IB) with a compound of formula (V)

$$R^6—X \qquad (V),$$

wherein
R$^6$ has the meaning indicated in this claim, and
X represents a leaving group,
in the presence of a base.

14. The composition containing at least one compound of general formula (I) according to claim 1 and a pharmacologically acceptable diluent.

15. A method for treating chronic obstructive pulmonary disease, acute myocardial syndrome, or acute myocardial infarction by administering to a human in need thereof a neutrophil elastase inhibitory amount of a compound of formula (I) according to claim 1.

* * * * *